(12) United States Patent
Kabanov et al.

(10) Patent No.: US 11,484,574 B2
(45) Date of Patent: Nov. 1, 2022

(54) POLYELECTROLYTE COMPLEXES FOR DELIVERY OF AGENTS TO THE CNS

(71) Applicant: The University of North Carolina at Chapel Hill, Chapel Hill, NC (US)

(72) Inventors: Alexander V. Kabanov, Chapel Hill, NC (US); Yuhang Jiang, Chapel Hill, NC (US); Xing Yi, Foster City, CA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/073,584

(22) PCT Filed: Feb. 1, 2017

(86) PCT No.: PCT/US2017/015930
§ 371 (c)(1),
(2) Date: Jul. 27, 2018

(87) PCT Pub. No.: WO2017/136376
PCT Pub. Date: Aug. 10, 2017

(65) Prior Publication Data
US 2019/0111109 A1 Apr. 18, 2019

Related U.S. Application Data

(60) Provisional application No. 62/289,548, filed on Feb. 1, 2016.

(51) Int. Cl.
| | | |
|---|---|---|
| *A61K 38/18* | (2006.01) | |
| *A61K 9/00* | (2006.01) | |
| *A61K 47/34* | (2017.01) | |
| *A61K 47/54* | (2017.01) | |
| *A61K 47/60* | (2017.01) | |
| *A61K 47/30* | (2006.01) | |
| *A61K 9/14* | (2006.01) | |
| *A61K 47/64* | (2017.01) | |
| *A61P 25/00* | (2006.01) | |
| *A61K 47/10* | (2017.01) | |
| *A61K 47/18* | (2017.01) | |
| *A61K 47/69* | (2017.01) | |
| *B82Y 5/00* | (2011.01) | |

(52) U.S. Cl.
CPC .......... *A61K 38/185* (2013.01); *A61K 9/0043* (2013.01); *A61K 9/146* (2013.01); *A61K 47/10* (2013.01); *A61K 47/183* (2013.01); *A61K 47/30* (2013.01); *A61K 47/34* (2013.01); *A61K 47/541* (2017.08); *A61K 47/60* (2017.08); *A61K 47/645* (2017.08); *A61P 25/00* (2018.01); *A61K 9/0019* (2013.01); *A61K 9/0085* (2013.01); *A61K 47/6929* (2017.08); *B82Y 5/00* (2013.01)

(58) Field of Classification Search
CPC .......................... A61K 38/185; A61K 47/645
See application file for complete search history.

(56) References Cited

U.S. PATENT DOCUMENTS

| | | | |
|---|---|---|---|
| 2014/0039068 A1* | 2/2014 | Bronich | ................ A61K 47/34 514/772.1 |
| 2015/0010557 A1 | 1/2015 | Bentz et al. | |

FOREIGN PATENT DOCUMENTS

WO    2008/141155 A1    11/2008

OTHER PUBLICATIONS

International Preliminary Report on Patentability corresponding to International Application No. PCT/US2017/015930 dated Aug. 16, 2018.
Kadam et al. "A review of nanotechnology with an emphasis on Nanoptex", Brazilian Journal of Pharmaceutical Sciences 51(2):255-263 (2015).
Notification of Transmittal of the International Search Report and the Written Opinion of the International Searching Authority, or the Declaration corresponding to International Application No. PCT/US2017/015930 dated Jun. 29, 2017.

* cited by examiner

*Primary Examiner* — Adam Weidner
(74) *Attorney, Agent, or Firm* — Myers Bigel, P.A.

(57) ABSTRACT

The present invention relates to compositions and methods for the delivery of agents to a subject, particularly to the central nervous system (CNS).

27 Claims, 28 Drawing Sheets

BDNF
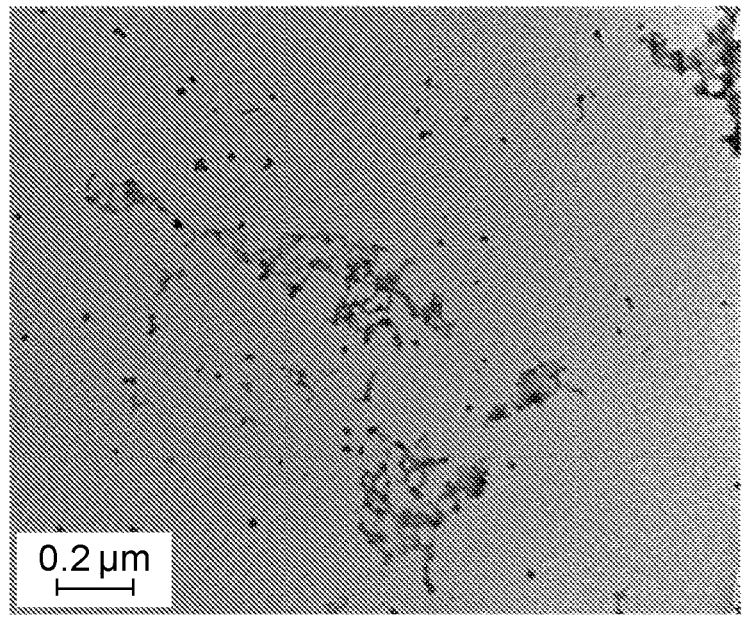
NANO-BDNF
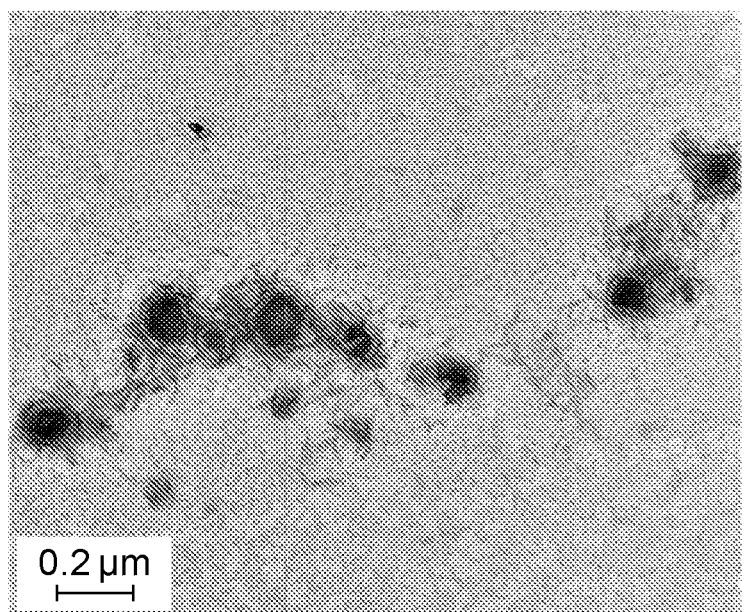
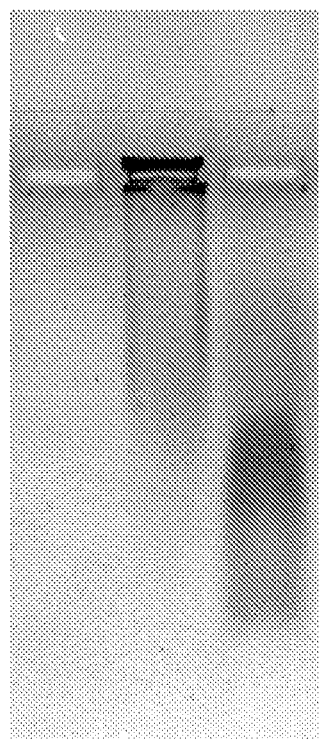
(+)
FIG. 2
FIG. 3

POLYELECTROLYTE COMPLEXES FOR DELIVERY OF AGENTS TO THE CNS

STATEMENT OF PRIORITY

This application is a 35 U.S.C. § 371 national phase application of PCT Application PCT/US2017/015930 filed Feb. 1, 2017, which claims the benefit of U.S. Provisional Application Ser. No. 62/289,548, filed Feb. 1, 2016, the entire contents of each of which are incorporated by reference herein in its entirety.

FIELD OF THE INVENTION

The present invention relates to compositions and methods for the delivery of agents to a subject, particularly to the central nervous system (CNS).

BACKGROUND OF THE INVENTION

Delivery of polypeptides to the central nervous system, e.g., the brain, is hindered by several factors, including the instability of administered polypeptides in vivo, sequestration by tissues, the presence of the blood brain barrier, and brain-to-blood efflux systems. One solution disclosed in WO 2008/141155 is the use of a complex comprising a therapeutic polypeptide and a synthetic polymer comprising at least one charge opposite to the charge of the therapeutic polypeptide.

There is a need in the art for new compositions and methods for the delivery of agents to the CNS.

SUMMARY OF THE INVENTION

The present invention is based on the development of compositions useful for delivering agents, e.g., therapeutic or protective agents such as polypeptides, to the CNS of a subject. The compositions provide improved delivery and/or retention of the agents. Thus, one aspect of the invention relates to a composition for delivery of an agent to the central nervous system of a subject, the composition comprising a polyelectrolyte complex comprising an agent and a synthetic polymer, wherein the charge ratio Z of the agent to the polymer is at least about 2.

Another aspect of the invention relates to a method of delivering an agent to the central nervous system of a subject, comprising delivering the composition of the invention to the subject, thereby delivering the agent to the central nervous system of the subject.

A further aspect of the invention relates to a method of treating a central nervous system disorder in a subject in need thereof, comprising delivering a therapeutically effective amount of the composition of the invention to the subject, thereby treating the central nervous system disorder in the subject.

An additional aspect of the invention relates to a method of stabilizing an agent for delivery to the central nervous system, comprising incorporating the agent into the polyelectrolyte complex of the composition of the invention.

Another aspect of the invention relates to a method of decreasing the efflux of an agent from the central nervous system after administration, comprising incorporating the agent into a polyelectrolyte complex comprising the agent and a polymer.

A further aspect of the invention relates to a method of delivering an agent to the central nervous system of a subject, comprising delivering a composition comprising a polyelectrolyte complex comprising the agent and a polymer to the subject by intranasal-to-brain delivery, thereby delivering the agent to the central nervous system of the subject.

An additional aspect of the invention relates to a method of treating a central nervous system disorder in a subject in need thereof, comprising delivering to the subject a therapeutically effective amount of a composition comprising a polyelectrolyte complex comprising an agent and a polymer by intranasal-to-brain delivery, thereby treating the central nervous system disorder in the subject.

These and other aspects of the invention are set forth in more detail in the description of the invention below.

BRIEF DESCRIPTION OF THE DRAWINGS

FIG. 2 shows transmission electron microscopy of native vs. nano-BDNF.

FIG. 3 shows horizontal agarose electrophoresis of native vs. nano-BDNF.

DETAILED DESCRIPTION OF THE INVENTION

Figure 1:
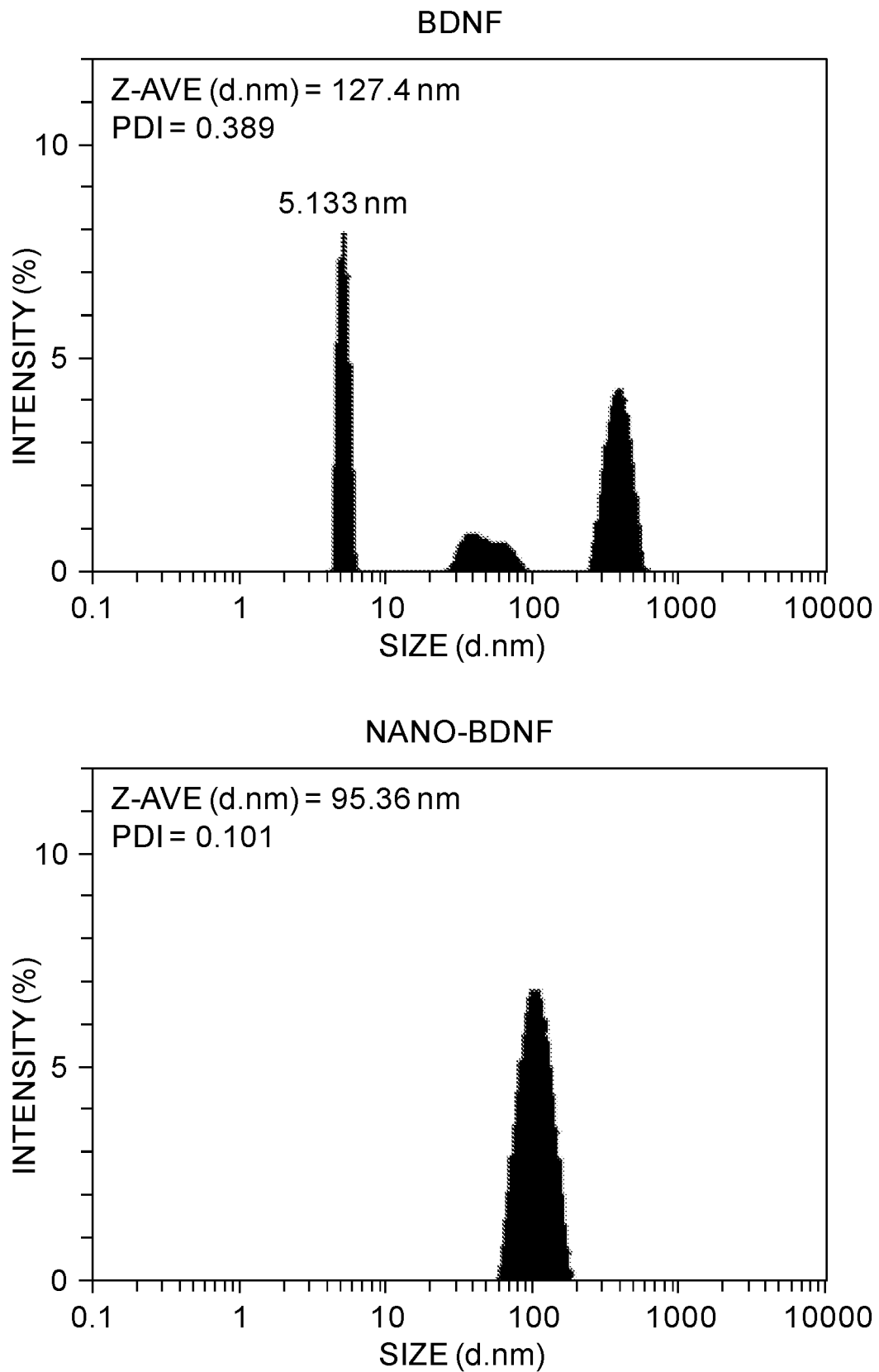
FIG. 1 shows dynamic light scattering analysis of native vs. nano-BDNF.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods known to those skilled in the art may be used for production of recombinant and synthetic polypeptides, antibodies or antigen-binding fragments thereof, manipulation of nucleic acid sequences, and production of transformed cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

I. Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

The transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz,* 537 F.2d 549, 551-52, 190 USPQ 461, 463 (CCPA 1976) (emphasis in the original); see also MPEP § 2111.03.

As used herein, the term "polypeptide" encompasses both peptides and proteins, unless indicated otherwise. The term also includes post-expression modifications of the polypeptide, for example, glycosylations, acetylations, phosphorylations and the like. In addition, protein fragments, analogs, mutated or variant proteins, fusion proteins and the like are included within the meaning of polypeptide.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

By the terms "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the terms "prevent," "prevents," or "prevention" and "inhibit," "inhibits," or "inhibition" (and grammatical equivalents thereof) are not meant to imply complete abolition of disease and encompasses any type of prophylactic treatment that reduces the incidence of the condition, delays the onset of the condition, and/or reduces the symptoms associated with the condition after onset.

An "effective," "prophylactically effective," or "therapeutically effective" amount as used herein is an amount that is sufficient to provide some improvement or benefit to the subject. Alternatively stated, an "effective," "prophylactically effective," or "therapeutically effective" amount is an amount that will provide some delay, alleviation, mitigation, or decrease in at least one clinical symptom in the subject. Those skilled in the art will appreciate that the effects need not be complete or curative, as long as some benefit is provided to the subject.

The terms "polymer," "polymer chain," or "polymeric chain,", as used herein interchangeably, denote molecules formed by covalent linking of two or more repeating units or monomers. The term "block copolymer" refers to conjugates of at least two different polymer segments, wherein each polymer segment comprises two or more adjacent units of the same kind. Such distinct polymer segments of block copolymers are termed "blocks."

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "charge ratio Z" as used herein refers to the ratio where the number of charged sites on the polymer is divided by the number of oppositely charged sites on the polypeptide in a polyelectrolyte complex.

The term "polyelectrolyte complex" as used herein refers to a complex resulting from the interaction between two oppositely charged agents, e.g., a polypeptide and a polyelectrolyte polymer forming multiple electrostatic bonds with each other. The complexes may or may not be cross-linked after formation to stabilize the complex. These complexes may be also additionally stabilized by hydrogen bonds and/or hydrophobic interactions between the species. In some embodiments it is preferred that the polypeptide and a polyelectrolyte polymer form multiple hydrogen bonds with each other. The term "multiple" as referred to herein with respect to electrostatic bonds or hydrogen bonds independently from each other means at least 2, e.g., at least 5, e.g., at least 7, e.g., at least 50. In some embodiments, both electrostatic and hydrogen bonds are formed.

The term "charge cluster" as used herein refers to a set of two or more charged amino acids in a polypeptide that are located within a defined distance of each other due to the primary, secondary, and/or tertiary structure of the polypeptide.

II. Complexes Based on Charge Ratios

The present invention is based on the development of compositions useful for delivering agents, e.g., therapeutic or protective agents such as polypeptides, to the CNS of a subject. The compositions provide improved delivery and/or retention of the agents. The complexes provide several advantages, including: (1) increased stability of the agent during storage; (2) increased stability of the agent in the blood (after intravenous administration) or within nasal mucosa (after intranasal administration); (3) minimized serum exposure and peripheral distribution of the agent; (4) increased delivery of the agent to the brain regions affected by a CNS disorder; and (5) release of active agent in these regions allowing its interaction with target receptors.

In contrast to the teachings in WO 2008/141155, the present inventors have discovered that effective polyelectrolyte complexes can be prepared when the net charges on the polypeptide and the polymer are not opposite to each other. By analyzing the charge ratio Z between the polypeptide and the polymer, the present inventors have found that complex formation is effective with same-net-charge polyelectrolyte pairs as long as the net charges involved in the binding reaction are opposite at the relevant pH.

Thus, one aspect of the present invention relates to a composition for delivery of a polypeptide to the central nervous system of a subject, the composition comprising a polyelectrolyte complex comprising a polypeptide and a polymer, e.g., a synthetic polymer, wherein the charge ratio Z of the polypeptide to the polymer is at least about 2. In certain embodiments, the charge ratio Z is at least about 4, at least about 10, or at least about 100, e.g., at least about 2, 3, 4, 5, 6, 7, 8, 9, 10, 20, 30, 40, 50, 60, 70, 80, 90, or 100 or any range therein. In some embodiments, the Z ratio is from about 2 to about 20, e.g., from about 4 to about 10. In one embodiment, the charge ratio Z is about 6 to about 7.

In certain embodiments of the invention, the polypeptide and the synthetic polymer have opposite net charges. In other embodiments, the polypeptide and the synthetic polymer have the same net charge. More important than the overall net charge of each component is the net charge of the portions of each component involved in the binding reaction.

In certain embodiments of the invention, the polypeptide comprises at least one charge cluster that is involved in the binding reaction, wherein charges within the cluster are separated by less than about 20 Å, e.g., less than about 15 Å or 7 Å, e.g., less than about 20, 19, 18, 17, 16, 15, 14, 13, 12, 11, 10, 9, 8, 7, 6, or 5 Å. In some embodiments, the at least one charge cluster has an opposite net charge to the net charge of the synthetic polymer, e.g., the at least one charge cluster has a net positive charge due to the presence of positively charged amino acids and the synthetic polymer has a net negative charge or the at least one charge cluster has a net negative charge due to the presence of negatively charged amino acids and the synthetic polymer has a net positive charge.

Charge clusters in a polypeptide may be readily identified by one of skill in the art by analyzing the primary amino acid sequence and the predicted or measured three-dimensional structure (e.g., crystal structure) of the polypeptide. Exemplary charge clusters and charge distances for several polypeptides are disclosed below. Each of the polypeptides below is a homopolymer, meaning that each residue mentioned in the tables below has a counterpart on the other monomer. Most of the charge clusters described in the tables exist on both monomers of the polypeptides. Where the residues are labeled specifically (A) or (B), the residues are on different monomers and the charge cluster is a cross-monomer charge cluster.

Neurotrophins

| Brain Derived Neurotrophic Factor (BDNF) | | |
|---|---|---|
| Charge clusters | | |
| Lys57-Arg7-His1-Lys65 | | |
| Arg6-Arg81 | | |
| Lys25-Arg104 | | |
| Lys41-Lys50 | | |
| Lys95-Arg97 | | |
| Arg69-Lys73-Arg119-Arg74 | | |
| Residue 1 | Residue 2 | Distance (Å) |
| His1 | Lys65 | 7.7 |
| Arg7 | His1 | 6.5 |
| Arg7 | Lys57 | 6.4 |
| Arg6 | Arg81 | 5.3 |
| Lys25 | Arg104 | 6.7 |
| Lys41 | Lys50 | 6.0 |
| Lys95 | Arg97 | 4.5~5.0 |
| Arg69 | Lys73 | 5.9 |
| Lys73 | Arg119 | 4.5~5.9 |
| Arg119 | Arg74 | 3.6~4.8 |

| Nerve Growth Factor (NGF) | | |
|---|---|---|
| Charge clusters | | |
| Lys25-Lys57-Arg103-His84 | | |
| His75(A)-Lys74(A)-Lys74(B)-His75(B)-Arg114(B) | | |
| Lys25-Arg103-His84 | | |
| Lys95-Lys34-Arg100-Lys32 | | |
| Arg59-Arg69 | | |
| Residue 1 | Residue 2 | Distance (Å) |
| His1 | Lys65 | 7.7 |
| Arg7 | His1 | 6.5 |
| Arg7 | Lys57 | 6.4 |
| Arg6 | Arg81 | 5.3 |
| Lys25 | Arg104 | 6.7 |
| Lys41 | Lys50 | 6.0 |
| Lys95 | Arg97 | 4.5~5.0 |
| Arg69 | Lys73 | 5.9 |
| Lys73 | Arg119 | 4.5~5.9 |
| Arg119 | Arg74 | 3.6~4.8 |

| Neurotrophin 4 (NT4) | | |
|---|---|---|
| Charge clusters | | |
| Arg28-Arg53 | | |
| Arg26-Arg27-Arg60 | | |
| Arg111-Arg34-Arg36 | | |
| Lys62-Arg79 | | |
| His85(A)-Arg84(A)-Arg84(B)-His85(B) | | |
| Residue 1 | Residue 2 | Distance (Å) |
| Arg28 | Arg53 | 5.8 |
| Arg27 | Arg60 | 2.8-4.2 |
| Arg34 | Arg36 | 4.1-5.4 |
| Arg26 | Arg27 | 6.1 |

Neurotrophin 4 (NT4)

| | | |
|---|---|---|
| Arg34 | Arg111 | 4.8 |
| Lys62 | Arg79 | 4.1 |
| His85 | Arg84 | 3.0-3.4 |
| Arg84(A) | Arg84(B) | 2.7-5.1 |

Neurotrophin 3 (NT3)

Charge clusters

Lys32-Arg100-Lys34-Lys95
Lys25-Lys57
His84-Arg103
Arg59-Arg69
His75-Lys74

| Residue 1 | Residue 2 | Distance (Å) |
|---|---|---|
| Lys32 | Arg100 | 6.5-7.0 |
| His84 | Arg103 | 4.2 |
| Arg59 | Arg69 | 3.4-5.3 |
| Lys25 | Lys57 | 6.6 |
| Lys32 | Lys34 | 6.6 |
| Arg100 | Lys34 | 4.1 |
| Lys34 | Lys95 | 5.5 |
| Lys95 | Arg100 | 6.4 |
| His75 | Lys74 | 5.6 |

GDNF Family of Ligands

Glial cell neurotrophic factor (GDNF)

Charge clusters

Arg130-Lys129-Arg66

| Residue 1 | Residue 2 | Distance (Å) |
|---|---|---|
| Lys129 | Arg130 | 5.3-6.1 |
| Lys129 | Arg66 | 7.1 |
| Arg66 | His126 | 8.0 |

Artemin

Charge clusters

Arg22-His21-Arg88
Arg15-Arg22
Arg28-Arg30
Arg38-Arg37-Arg40(A)-Arg40(B)-His43(A)-Arg71(B)
Arg3-Arg5
Arg57-Arg63

| Residue 1 | Residue 2 | Distance (Å) |
|---|---|---|
| His21 | Arg88 | 4.9-5.2 |
| Arg15 | Arg22 | 3.2-6.7 |
| Arg28 | Arg30 | 5.0-6.2 |
| His43(A) | Arg71(B) | 5.7 |
| Arg3 | Arg5 | 4.0-4.3 |
| Arg37 | Arg38 | 8.1-8.2 |
| Arg37 | Arg40 | 8.6 |
| Arg40(A) | Arg40(B) | 7.7 |
| Arg40(B) | His43(A) | 5.9 |
| Arg57 | Arg63 | 7.2 |
| His21 | Arg22 | 8.4 |

Ciliary neurotrophic factor

Charge clusters

Arg3-His1-Arg2-His180-Arg72-Arg171
Arg177-Arg25-Arg28
Lys39-His40
Lys140-His106-His110(A)-Arg19(B)
His84(A)-His8(B)
His106-His41
His97-Lys154-Arg89
Arg177-His174
Arg89(A)-Arg136(B)

| Residue 1 | Residue 2 | Distance (Å) |
|---|---|---|
| His1 | Arg3 | 5.0 |
| His1 | Arg2 | 8.8 |
| Arg3 | Arg2 | 5.7-7.3 |
| Arg2 | His180 | 7.0-7.3 |
| His180 | Arg72 | 6.5-7.8 |
| Arg72 | Arg171 | 4.9-6.8 |
| Arg25 | Arg177 | 3.7-6.9 |
| Arg25 | Arg28 | 6.4-8.1 |
| Lys39 | His40 | 3.7 |
| Lys140 | His106 | 7.8 |
| His106 | His110 | 5.7-6.9 |
| His110(A) | Arg19(B) | 7.5 |
| His84(A) | His84(B) | 6.4 |
| His41 | His106 | 8.5 |
| His97 | Lys154 | 4.8 |
| Lys154 | Arg89 | 3.6 |
| Arg177 | His174 | 4.4 |
| Arg89(A) | Arg136(B) | 7.5 |

The polymer in the polyelectrolyte complex may be any type of polymer that is suitable for the complex. The polymer may be a homopolymer, a random copolymer, or a block or graft copolymer. The homopolymer or random copolymer may have a net negative or positive charge, e.g., homopolymers of glutamic acid or aspartic acid.

In some embodiment of the instant invention, the polymer, e.g., synthetic polymer, is a block or graft copolymer. More specifically, the synthetic polymer is a block or graft copolymer, which comprises at least one polyion segment and at least one nonionic water soluble polymer segment. Block copolymers are conjugates of at least two different polymer segments. The simplest block copolymer architecture contains two segments joined at their termini to give an A-B type diblock. Consequent conjugation of more than two segments by their termini yields A-B-A type triblock, A-B-A-B-type multiblock, or even multisegment A-B-C-architectures. If a main chain in the block copolymer can be defined in which one or several repeating units are linked to different polymer segments, then the copolymer has a graft architecture of, e.g., an $A(B)_n$ type. More complex architectures include for example $(AB)_n$ or $A_nB_m$, starblocks which have more than two polymer segments linked to a single center. An exemplary block copolymer of the instant invention would have the formula A-B or B-A, wherein A is a polyion segment and B is a nonionic water soluble polymer segment. The segments of the block copolymer may have from about 2 to about 1000 repeating units or monomers.

The polyion segment may be a polycation (i.e., a polymer that has a net positive charge at a specific pH) or a polyanion (i.e., a polymer that has a net negative charge at a specific pH). Examples of polycation segments include, but are not limited to, polymers and copolymers and their salts comprising units deriving from one or more monomers including, without limitation, primary, secondary and/or tertiary amines, each of which can be partially or completely quaternized, thereby forming quaternary ammonium salts.

Examples of these monomers include, without limitation, cationic amino acids (e.g., lysine, arginine, histidine, ornithine and the like), alkyleneimines (e.g., ethyleneimine, propyleneimine, butileneimine, pentyleneimine, hexyleneimine, spermine, and the like), vinyl monomers (e.g., vinylcaprolactam, vinylpyridine, and the like), acrylates and methacrylates (e.g., N,N-dimethylaminoethyl acrylate, N,N-dimethylaminoethyl methacrylate, N,N-diethylaminoethyl acrylate, N,N-diethylaminoethyl methacrylate, t-butylaminoethyl methacrylate, acryloxyethyltrimethyl ammonium halide, acryloxyethyldimethylbenzyl ammonium halide, methacrylamidopropyltrimethyl ammonium halide and the like), allyl monomers (e.g., dimethyl diallyl ammonium chloride), aliphatic, heterocyclic or aromatic ionenes. Suitable polycations include, without limitation, polyamines (e.g., spermine, polyspermine, polyethyleneimine, polypropyleneimine, polybutileneimine, polypentyleneimine, polyhexyleneimine and copolymers thereof), copolymers of tertiary amines and secondary amines, partially or completely quaternized amines, the quaternary ammonium salts of the polycation fragments, polypeptides such as poly-L-lysine, poly-D-lysine, poly-L-arginine, poly-D-arginine and their copolymers, N-substituted polyaspartamides such as poly [N-(2-aminoethyl)aspartamide] [PAsp(EDA)], poly {N—[N'-(2-aminoethyl)-2-aminoethyl]aspartamide [PAsp(DET)], poly(N—{N'—[N"-(2-aminoethyl)-2-aminoethyl]-2-aminoethyl}aspartamide) [PAsp(TET)], poly-[N—(N'—{N"—[N'''-(2-aminoethyl)-2-aminoethyl]-2-aminoethyl}-2-aminoethyl)aspartamide] [PAsp(TEP)], poly(amidoamine)s and the like.

In some embodiments, the polyion block is negatively charged, e.g., due to the presence of negatively charged amino acids. Examples of suitable polyanion blocks include, without limitation, poly(glutamic acid), poly(aspartic acid), or a copolymer of poly(glutamic acid) and/or poly(aspartic acid) with other amino acids that contain a majority of negatively charged amino groups. In these blocks the amino acids may have any stereochemical orientation, e.g., L isomers, D isomers, or a mixture of L and D isomers. Other examples of polyion blocks include, without limitation, polymers and their salts comprising units deriving from one or more monomers including: unsaturated ethylenic monocarboxylic acids, unsaturated ethylenic dicarboxylic acids, ethylenic monomers comprising a sulfonic acid group, their alkali metal, and their ammonium salts. Examples of these monomers include acrylic acid, methacrylic acid, aspartic acid, alpha-acrylamidomethylpropanesulphonic acid, 2-acrylamido-2-methylpropanesulphonic acid, citrazinic acid, citraconic acid, trans-cinnamic acid, 4-hydroxy cinnamic acid, trans-glutaconic acid, glutamic acid, itaconic acid, fumaric acid, linoleic acid, linolenic acid, maleic acid, nucleic acids, trans-beta-hydromuconic acid, trans-trans-muconic acid, oleic acid, 1,4-phenylenediacrylic acid, phosphate 2-propene-1-sulfonic acid, ricinoleic acid, 4-styrene sulfonic acid, styrenesulphonic acid, 2-sulphoethyl methacrylate, trans-traumatic acid, vinylsulfonic acid, vinylbenzenesulphonic acid, vinyl phosphoric acid, vinylbenzoic acid and vinylglycolic acid and the like as well as carboxylated dextran, sulphonated dextran, heparin and the like. Examples of polyanions include, but are not limited to, polymaleic acid, polyamino acids (e.g., polyaspartic acid, polyglutamic acid, and their copolymers) polyacrylic acid, polymethacrylic acid, heparin and the like.

The polycations and polycation segments can be produced by polymerization of monomers that themselves may not be cationic, such as for example, 4-vinylpyridine, and then converted into a polycation form by various chemical reactions of the monomeric units, for example alkylation, resulting in appearance of ionizable groups. The conversion of the monomeric units can be incomplete resulting in a copolymer having a portion of the units that do not have ionizable groups, such as for example, a copolymer of vinylpyridine and N-alkylvinylpyridinuim halide.

Polycation segments can be a copolymer containing more than one type of monomeric units including a combination of cationic units with at least one other type of unit including, for example, cationic units, anionic units, zwitterionic units, hydrophilic nonionic units and/or hydrophobic units. Such polycation segments can be obtained by copolymerization of more than one type of chemically different monomers. When such a copolymer is employed, the charged groups should be spaced close enough together so that, when reacted with the other components, a complex is formed. In a preferred embodiment, the portion of non-cationic units is relatively low so that the polymer or polymer block remains largely cationic in nature. The polycation-containing polymer may be a blend of two or more polymers of different structures, such as polymers containing different degrees of polymerization, backbone structures, and/or functional groups.

Examples of polyanion segments include, but are not limited to, polymers and their salts comprising units deriving from one or more monomers including: unsaturated ethylenic monocarboxylic acids, unsaturated ethylenic dicarboxylic acids, ethylenic monomers comprising a sulfonic acid group, their alkali metal, and their ammonium salts. Examples of these monomers include, but are not limited to, acrylic acid, methacrylic acid, aspartic acid, alpha-acrylamidomethylpropanesulphonic acid, 2-acrylamido-2-methylpropanesulphonic acid, citrazinic acid, citraconic acid, trans-cinnamic acid, 4-hydroxy cinnamic acid, trans-glutaconic acid, glutamic acid, itaconic acid, fumaric acid, linoleic acid, linolenic acid, maleic acid, nucleic acids, trans-beta-hydromuconic acid, trans-trans-muconic acid, oleic acid, 1,4-phenylenediacrylic acid, phosphate 2-propene-1-sulfonic acid, ricinoleic acid, 4-styrene sulfonic acid, styrenesulphonic acid, 2-sulphoethyl methacrylate, trans-traumatic acid, vinylsulfonic acid, vinylbenzenesulphonic acid, vinyl phosphoric acid, vinylbenzoic acid and vinylglycolic acid and the like as well as carboxylated dextran, sulphonated dextran, heparin and the like. The examples of polyanions include, but are not limited to, polymaleic acid, polyamino acids (e.g., polyaspartic acid, polyglutamic acid, and their copolymers) polyacrylic acid, polymethacrylic acid, and the like.

The polyanions and polyanion segments can be produced by polymerization of monomers that themselves may not be anionic or hydrophilic, such as for example, tert-butyl methacrylate or citraconic anhydride, and then converted into a polyanion form by various chemical reactions of the monomeric units, for example hydrolysis, resulting in ionizable groups. The conversion of the monomeric units can be incomplete resulting in a copolymer having a portion of the units that do not have ionizable groups, such as for example, a copolymer of tert-butyl methacrylate and methacrylic acid.

The polyanion segment can be a copolymer containing more than one type of monomeric unit including a combination of anionic units with at least one other type of unit including anionic units, cationic units, zwitterionic units, hydrophilic nonionic units and/or hydrophobic units. Such polyanions and polyanion segments can be obtained by copolymerization of more than one type of chemically different monomer. When such a copolymer is employed, the charged groups should be spaced close enough together so that, when reacted with the other components, a complex is formed. In some embodiments, the portion of non-anionic units is relatively low so that the polymer or polymer block remains largely anionic and hydrophilic in nature. The polyanion-containing polymer may be a blend of two or more polymers of different structures, such as polymers containing different degrees of polymerization, backbone structures, and/or functional groups.

In one embodiment, the polyion segment is a polypeptide selected from the group consisting of polymers or copolymers of lysine, histidine, arginine, ornithine, aspartic acid and/or glutamic acid, and their salts. Examples of such synthetic polyions include polylysine, polyhistidine, polyarginine, polyornithine, polyaspartic acid, polyglutamic acid, and their salts. In another embodiment, the polyion segment is selected from the group consisting of polyacrylic acid, polyalkylene acrylic acid, polyalkyleneimine, polyethylenimine, polyphosphates, and their salts.

The nonionic water soluble polymer segment may be selected from, without limitation, the group consisting of polyethers (e.g., poly(ethylene oxide) (PEO) (or poly(oxyethylene) that is used interchangeably with poly(ethylene glycol) (PEG)), polysaccharides (e.g., dextran), polyglycerols, homopolymers and copolymers of vinyl monomers (e.g., polyacrylamide, polyacrylic esters (e.g., polyacryloyl morpholine), polymethacrylamide, poly(N-(2-hydroxypropyl)methacrylamide, polyvinyl alcohol, polyvinylpyrrolidone, polyvinyltriazole, N-oxide of polyvinylpyridine, copolymer of vinylpyridine and vinylpyridine N-oxide), polyortho esters, polyaminoacids, polyglycerols, poly(2-oxazolines) (e.g., poly(2-methyl-2-oxazoline), poly(2-ethyl-2-oxazoline) and copolymers), polysarcosine and derivatives thereof. Preferably, nonionic polymer segments are nontoxic and nonimmunogenic. Examples of suitable nonionic blocks include, without limitation, PEG, poly(2-methyl-2-oxazoline), poly(2-ethyl-2-oxazoline), poly-sarcosine, and/or elastin-like polypeptides. In a particular embodiment, the water soluble polymers are PEG), a copolymer of ethylene oxide and propylene oxide, poly(2-methyl-2-oxazoline), poly(2-ethyl-2-oxazoline) or polysarcosine. If the nonionic water soluble polymer segment is PEO, the preferred molecular mass of such polymer is between about 300 and about 20,000, e.g., between about 1,500 and about 15,000, e.g., between about 2,000 and about 10,000, e.g., about 4,000 and about 10,000.

The degree of polymerization of the polyion segments is typically between about 10 and about 100,000. In certain embodiments, the degree of polymerization is between about 20 and about 10,000, e.g., between about 10 and about 1,000, and e.g., between about 10 and about 200. Independently from the polyion segment, the degree of polymerization of the nonionic water soluble polymer segment is about 10 and about 100,000, e.g., between about 20 and about 10,000, e.g., between about 10 and about 1,000, e.g., between about 10 and about 200.

In some embodiments of the invention, the synthetic polymer is a block copolymer comprising poly(glutamic acid) or poly(aspartic acid) and poly(ethylene glycol). In certain embodiments, the block copolymer comprises poly(ethylene glycop$_{10-1000}$, poly(ethylene glycol)$_{20-500}$, e.g., poly(ethylene glycol)$_{40-250}$, e.g., poly(ethylene glycol)$_{100-130}$. In certain embodiments of the invention, the synthetic polymer is a block copolymer comprising poly(glutamic acid) or poly(aspartic acid) and polysarcosine. In certain embodiments of the invention, the synthetic polymer is a block copolymer comprising poly(glutamic acid) or poly(aspartic acid) and poly(2-methyl-2-oxazoline), poly(2-ethyl-2-oxazoline) or their copolymers. In some embodiments of the invention, the synthetic polymer is a block copolymer comprising poly(glutamic acid)$_{8-150}$, e.g., poly(glutamic acid)$_{20-100}$, e.g., poly(glutamic acid)$_{40-60}$.

One of skill in the art can readily select suitable agents having a positive or negative charge (e.g., cluster charge or net overall charge) and match them with suitable polymers comprising the appropriate ionic block of the opposite charge.

The polyelectrolyte complexes of the present invention may contain any suitable agent, e.g., a polypeptide. In some embodiments, the agent is a therapeutic or protective agent, e.g., a therapeutic or protective polypeptide. While some embodiments of the instant invention involve polypeptides contained within the polyelectrolyte complex, it is also within the scope of the instant invention to encapsulate other therapeutic agents or compounds of interest into the polyelectrolyte complex. Such agents or compounds include, without limitation, polypeptides, proteins, peptides, nucleic acids, and compounds such as synthetic and natural drugs.

In some embodiments of the instant invention, the polypeptide of interest in the polyelectrolyte complex is a therapeutic polypeptide, e.g., it effects amelioration and/or cure of a disease, disorder, pathology, and/or the symptoms associated therewith. The proteins may have therapeutic value against neurological disorders (particularly of the CNS) including, without limitation, neurological degenerative disorders and neurodevelopmental disorders, such as Alzheimer's disease, Parkinson's disease, Huntington's disease (HD), Rett syndrome, stroke, trauma, infections, meningitis, encephalitis, gliomas, cancers (including brain metastasis), HIV-1 associated dementia (HAD), HIV associated neurocognitive disorders (HAND), paralysis, amyotrophic lateral sclerosis (ALS or Lou Gehrig's disease), multiple sclerosis (MS), CNS-associated cardiovascular disease, prion disease, obesity, metabolic disorders, inflammatory disease, and lysosomal storage diseases (LSDs; such as, without limitation, Gaucher's disease, Pompe disease, Niemann-Pick, Hunter syndrome (MPS II), Mucopolysaccharidosis I (MPS I), GM2-gangliosidoses, Gaucher disease, Sanfilippo syndrome (MPS IIIA), Tay-Sachs disease, Sandhoffs disease, Krabbe's disease, metachromatic leukodystrophy, and Fabry disease). Therapeutically active polypeptides include, but are not limited to, enzymes, antibodies, hormones, growth factors, other polypeptides, which administration to the brain can effect amelioration and/or cure of a disease, disorder, pathology, and/or the symptoms associated therewith. Neuroactive polypeptides useful in this invention include but are not limited to endocrine factors, growth factors, hypothalamic releasing factors, neurotrophic factors, paracrine factors, neurotransmitter polypeptides, antibodies and antibody fragments which bind to any of the above polypeptides (such neurotrophic factors, growth factors, and others), antibodies and antibody fragments which bind to the receptors of these polypeptides (such as neurotrophic factor receptors), cytokines, endorphins, polypeptide antagonists, agonists for a receptor expressed by a CNS cell, polypeptides involved in lysosomal storage diseases, and the like. In a particular embodiment, the therapeutic protein exerts its effect on the CNS. In another particular embodiment, the therapeutic protein does not cross the BBB by itself.

In certain embodiments, the polypeptide is a neurotrophin, e.g., selected from, without limitation, brain derived neurotrophic factor, nerve growth factor, neurotrophin 3, neurotrophin 4, glial cell derived neurotrophic factor, artemin, neurturin, persephin, ciliary neurotrophic factor, and any combination thereof.

Examples of other polypeptides include, without limitation, catalase, telomerase, superoxide dismutase (SOD), glutathione peroxidase, glutaminase, cytokines, endorphins (e.g., enkephalin), growth factors (e.g., epidermal growth factor (EGF), acidic and basic fibroblast growth factor (aFGF and bFGF), insulin-like growth factor I (IGF-I), brain-derived neurotrophic factor (BDNF), glial-derived neurotrophic factor (GDNF), platelet derived growth factor (PDGF), vascular growth factor (VGF), nerve growth factor (NGF), insulin-like growth factor-II (IGF-II), tumor necrosis factor-B (TGF-B), leukemia inhibitory factor (LIF), various interleukins, and the like), antiapoptotic proteins (BCL-2, PI3 kinase, and the like), amyloid beta binders (e.g., antibodies), modulators of α-, β-, and/or γ-secretases, vasoactive intestinal peptide, leptin, acid alpha-glucosidase (GAA), acid sphingomyelinase, iduronate-2-sultatase (I2S), α-L-iduronidase (IDU), β-Hexosaminidase A (HexA), Acid β-glucocerebrosidase, N-acetylgalactosamine-4-sulfatase, α-galactosidase A, and neurotransmitters.

In one embodiment, the present invention can be used as a treatment modality against acute nerve toxicity from warfare agents based on the brain delivery of butyrylcholinesterase or acetylcholinesterase, cholinesterase reactivators (e.g., oxime compounds), scavengers of organophosphate and carbamate inhibitors. Since butyrylcholinesterase (BChE) also hydrolyzes many ester-containing drugs, such as cocaine and succinylcholine, the BChE within complexes of this invention has therapeutic value against cocaine addiction and toxicity (e.g., Carmona et. al. (1999) Drug Metab. Dispos., 28: 367-371; Carmona (2005) Eur. J. Pharmacol., 517: 186-190).

In one embodiment, the present invention can be used for delivery of consumer health products, such as nutraceuticals, lifestyle agents, or hormones.

The methods of the current invention involve the use of polypeptide complexes containing one or several useful polypeptides, or use of several complexes containing different polypeptides that can be administered alone or with cells, simultaneously or separately from each other. The complexes may be in the same composition or may be in separate compositions.

The polyelectrolyte complexes of the present invention may be in the form of a particle, e.g., a microparticle (diameter less than 1 mm) or a nanoparticle (diameter less than 1 μm). In some embodiments, the size of the complexes is between about 5 nm and about 500 nm, e.g., between about 5 and about 250 nm, e.g., between about 10 and about 150 nm, e.g., between about 10 nm and about 140 nm, e.g., between about 20 and about 100 nm. The complexes do not aggregate and remain within the preferred size range for at least 1 hour after dispersion in the aqueous solution at the physiological pH and ionic strength, for example in phosphate buffered saline, pH 7.4. The sizes may be measured as effective diameters by dynamic light scattering (see, e.g., Batrakova et al., *Bioconjugate Chem.* 18: 1498 (2007)). In some embodiments, after dispersion in aqueous solution, the complexes remain stable, i.e., do not aggregate and/or precipitate for at least 2 hours, e.g., for 12 hours, e.g., for 24 hours.

To prepare a synthetic polymer for use in a polyelectrolyte complex with a polypeptide of interest, block copolymers are synthesized by conjugation of a polyion segment (e.g., poly(glutamic acid) or poly(aspartic acid)) and a nonionic water soluble segment (e.g., poly(ethylene glycol, poly(2-methyl-2-oxazoline), poly(2-ethyl-2-oxazoline) or polysarcosine)). Complexes can be formed by the addition of a solution of the polypeptide of interest (e.g., BDNF (1 mg/ml)) to a solution of a block copolymer (e.g., PEG-PGA (2 mg/ml)) in a buffer (e.g., phosphate buffer saline (pH 7.4)) producing slightly opalescent dispersions.

In a particular embodiment, the particles are administered to a cell of the body in the isotonic solution at physiological pH 7.4. However, the complexes can be prepared before administration at pH below or above pH 7.4. It is recognized that many polypeptides of interest in this invention are polyampholytes, which contain both positive and negative groups. The balance of the positive and negative groups of such polypeptide depend on their chemical structure as well as on the pH of the external solution. At pH below the isoelectric point (pI) the polypeptides may be positively charged. At pH above the pI the polypeptides may be negatively charged. Therefore, the complexes of this invention may be produced by reacting polypeptides below the pH point with polyanion. These complexes may be also prepared by reacting polypeptides above the pI with polycations. Following preparation of the complexes the pH of the solution may be changed to the desired pH, for example, pH 7.4 for further administration. In some cases, the polypeptides may contain sites or domains with multiple positive or negative groups closely positioned to one another. Such polypeptides may form complexes with oppositely charged polyions (e.g., polycations in case of sites with multiple negative groups in polypeptide or polyanions in case of sites with multiple positive groups) both below and above the pH. In certain embodiments, to improve the stability, decrease size and polydispersity the complexes can be prepared by mixing the polypeptide and polyion in a microfluidics mixer. After mixing the polypeptide and polyion, the complex formed may be separated and purified from the excess unreacted components (e.g., polyion) using techniques known in the art such as gel permeation chromatography. In some embodiments the polyion complex contains less than 10% free polyion not incorporated in the complex, e.g., less than 2% free polyion, e.g., the complex is essentially free of the free polyion.

The present invention further provides a composition comprising the polyelectrolyte complex of the invention and a suitable carrier, e.g., a pharmaceutically acceptable carrier.

By “pharmaceutically acceptable” it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The polyelectrolyte complexes of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the polyelectrolyte complex is typically admixed with, inter alia, an acceptable carrier. The carrier can be a solid or a liquid, or both, and is preferably formulated with the polyelectrolyte complex as a unit-dose formulation, for example, a tablet, which can contain from 0.01 or 0.5% to 95% or 99% by weight of the polyelectrolyte complex. One or more polyelectrolyte complexes can be incorporated in the formulations of the invention, which can be prepared by any of the well-known techniques of pharmacy.

A further aspect of the invention is a method of treating subjects in vivo, comprising administering to a subject a pharmaceutical composition comprising a polyelectrolyte complex of the invention in a pharmaceutically acceptable carrier, wherein the pharmaceutical composition is administered in a therapeutically effective amount. Administration of the polyelectrolyte complexes of the present invention to a human subject or an animal in need thereof can be by any means known in the art for administering compounds.

Non-limiting examples of formulations of the invention include those suitable for oral, rectal, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intracranial, intrathecal, and inhalation administration, administration to the liver by intraportal delivery, as well as direct organ injection (e.g., into the liver, into a limb, into the brain or spinal cord for delivery to the central nervous system, into the pancreas, or into a tumor or the tissue surrounding a tumor). The most suitable route in any given case will depend on the nature and severity of the condition being treated and on the nature of the particular compound which is being used. In some embodiments, it may be desirable to deliver the formulation locally to avoid any side effects associated with systemic administration. For example, local administration can be accomplished by direct injection at the desired treatment site, by introduction intravenously at a site near a desired treatment site (e.g., into a vessel that feeds a treatment site). In some embodiments, the formulation can be delivered locally to ischemic tissue. In certain embodiments, the formulation can be a slow release formulation, e.g., in the form of a slow release depot.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6: 273-313; and Raeburn et al., *J. Pharmacol. Toxicol. Meth.* 27: 143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3: 318 (1986)) and typically take the form of an optionally buffered aqueous solution of the compound. Suitable formulations comprise citrate or bis\tris buffer (pH 6) or ethanol/water and contain from 0.1 to 0.2M of the compound.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the compound is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa.). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmol/kg and to 33 µmol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of a CNS disorder. In certain embodiments, the subject is in need of treatment for a CNS disorder, i.e., a subject that has a CNS disorder or is at increased risk for a CNS disorder relative to the general population.

A further aspect of the invention relates to a method of stabilizing a polypeptide for delivery to the central nervous system, comprising incorporating the polypeptide into the polyelectrolyte complex of the invention. The increase in stability afforded by the complex is advantageous for storage as well as delivery of polypeptides to the CNS.

Another aspect of the invention relates to a method of decreasing the efflux of a polypeptide from the central nervous system after administration, comprising incorporating the polypeptide into a polyelectrolyte complex of the invention. The present inventors have unexpectedly found that that efflux of the polypeptide from the brain may be decreased when the polypeptide is delivered in a polyelectrolyte complex as compared to a polypeptide that is not in a complex.

An additional aspect of the invention relates to a method of delivering a polypeptide to the central nervous system of a subject, comprising delivering the polyelectrolyte complex of the invention to the subject, thereby delivering the polypeptide to the central nervous system of the subject.

A further aspect of the invention relates to a method of treating a central nervous system disorder in a subject in need thereof, comprising delivering a therapeutically effective amount of the polyelectrolyte complex of the invention to the subject, thereby treating the central nervous system disorder in the subject. The central nervous system disorder may be, without limitation, any of the disorders described above, e.g., neurodegenerative or neurodevelopmental disorders. In some embodiments, the CNS disorder may be stroke or Rett syndrome.

Rett syndrome (RTT) is a rare neurodevelopmental disorder for which no therapeutic intervention is currently available. RTT affects approximately 1 in 10,000 females and is characterized by a spectrum of dysfunctions including abnormal motor, respiratory and autonomic control, cognitive impairment, autistic-like behaviors and increased risk of seizures. The condition is caused by mutations of the transcriptional regulatory gene encoding methyl-CpG-binding protein 2 (MeCP2). Brain-derived neurotrophic factor (BDNF) is deregulated in RTT and has been established as a potential therapeutic agent for RTT. However, brain delivery of BDNF is tremendously challenging because of the extremely short serum half-life of the native protein, its limited passage across the blood-brain barrier (BBB), and the rapid efflux of the neurotrophin from brain to blood. The polyelectrolyte complexes of the present invention provide increased stability of BDNF, rapid release of active BDNF in the brain, and enhanced delivery to regions of the brain relevant to RTT pathology compared to administration of native BDNF.

Without being bound by theory, it is believed that complexes may bind to and enter inside neuronal cells and/or neuronal peripheral projections and be transported to the brain through the process known as retrograde transport (Zweifel et al. (2005) Nat. Rev. Neurosci., 6: 615-625; U.S. Patent Application Publication 2003/0083299) or a similar process. The unique structure of the complexes of the present invention and, in particular, combination of ionic and non-ionic polymeric chains in the copolymers provides protection to the polypeptides, minimizes damage to cells and tissues, and facilitates free migration of the complexes to the brain.

III. Intranasal-To-Brain Delivery of Polyelectrolyte Complexes

The present invention is based in part on the finding by the inventors that the intranasal-to-brain (INB) route is highly effective for delivery of polyelectrolyte complexes to the CNS. INB delivery may provide increased brain influx and/or decreased brain efflux of the polypeptide in the complex. Further, INB delivery unexpectedly may provide enhanced delivery of the polypeptide to specific regions of the brain, such as the brainstem and hippocampus. These two regions are of particular importance to Rett syndrome, stroke, and other pathologies.

Thus, one aspect of the invention relates to method of delivering an agent, e.g., a polypeptide, to the central nervous system of a subject, comprising delivering a composition comprising a polyelectrolyte complex comprising the agent and a polymer to the subject by intranasal-to-brain delivery, thereby delivering the agent to the central nervous system of the subject.

A further aspect of the invention relates to a method of treating a central nervous system disorder in a subject in need thereof, comprising delivering to the subject a therapeutically effective amount of a composition comprising a polyelectrolyte complex comprising an agent, e.g., a polypeptide, and a polymer by intranasal-to-brain delivery, thereby treating the central nervous system disorder in the subject.

An additional aspect of the invention relates to a method of decreasing the efflux of an agent, e.g., a polypeptide, from the central nervous system after administration, comprising incorporating the agent into a polyelectrolyte complex comprising the agent and a polymer.

In each of these methods, the polyelectrolyte complex can be any polyelectrolyte complex known in the art. One of skill in the art can readily select suitable agents having a positive or negative charge (e.g., cluster charge or net overall charge) and match them with suitable polymers comprising the appropriate ionic block of the opposite charge. In certain embodiments, the polyelectrolyte complex is a complex of the invention described above.

INB delivery may be carried out using techniques known in the art. In particular, the compositions of the invention may be delivered into the upper nasal turbinate area close to the olfactory bulb (e.g., at the cribriform plate). Suitable carriers and formulations for intranasal delivery are known in the art and are described above.

Having described the present invention, the same will be explained in greater detail in the following examples, which are included herein for illustration purposes only, and which are not intended to be limiting to the invention.

Example 1

Charge Ratios in Polyelectrolyte Complexes 0.1 mg/ml BDNF solution in 10 mM phosphate buffer (pH 7.4) was mixed with PEG-block-poly(L-glutamic acid sodium salt) (PEG-PGA) block polymer solution in the same buffer at the charge ratio Z=10. The molecular mass of the PEG block was 5.0 kDa (the degree of polymerization about 113) and of PGA 7.5 kDa (the degree of polymerization about 50), which corresponds to the abbreviation $PEG_{113}$-$PGA_{50}$. The hydrodynamic size of each sample was measured by dynamic light scattering. Formulating BDNF into nano-BDNF significantly prevented BDNF aggregation and resulted in a narrowly distributed nanoparticle with size of about 100 nm, PDI=0.165 (FIG. 1). From the figure it can be seen that PEG-PGA has formed a complex with BDNF protein.

Formation of nano BDNF was confirmed by transmission electron microscopy. Native and nano BDNF were deposited on a carbon film and positively stained with 2% uranyl acetate solution. While native BDNF appeared to be randomly dispersing, nano-BDNF appeared as spherical clusters with a core-shell structure (FIG. 2). The micrograph depicts the spherical morphology of nano-BDNF at the nanoscale size.

Native and nano BDNF (Z=100) were formed in water and loaded on a 0.5% agarose gel (Lane 1: PEG-PGA; Lane 2: BDNF; Lane 3: nano-BDNF). Horizontal electrophoresis was performed in native gel running buffer under 80V for 1 hour. The results are shown in FIG. 3. In lane 1, Coomassie Blue dye selectively binds positively charged residues on the protein, so it doesn't stain the PEG-PGA polymer at all, which makes it a perfect staining reagent to observe the movement of BDNF alone. In lane 2, BDNF binds strongly to polysaccharide structures like agarose (Kanato, Kitajima et al. 2008), and would stick to the edge of the wells on this gel. Small amount of BDNF migrates to the cathode, possibly due to interaction with soluble agarose oligomers. In, lane 3, PEG-PGA was able to compete with agarose and carry BDNF to the cathode direction. 0.5% agarose has very big pore sizes (~500 nm), so nano-BDNF was able to migrate in it.

Figure 4:
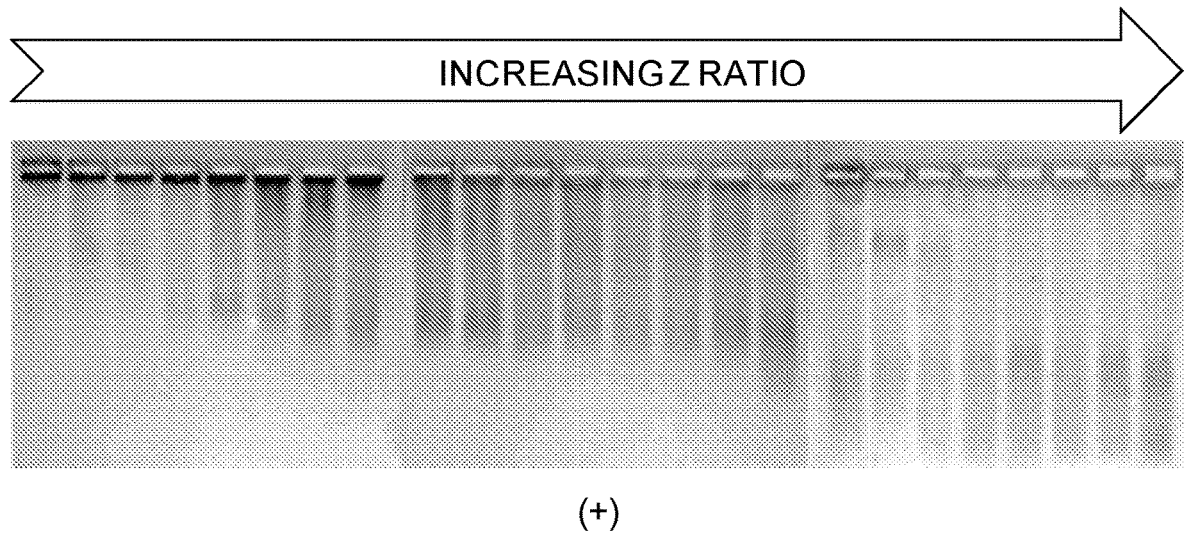
FIG. 4 shows charge saturation analysis by horizontal agarose electrophoresis.
Figure 4:
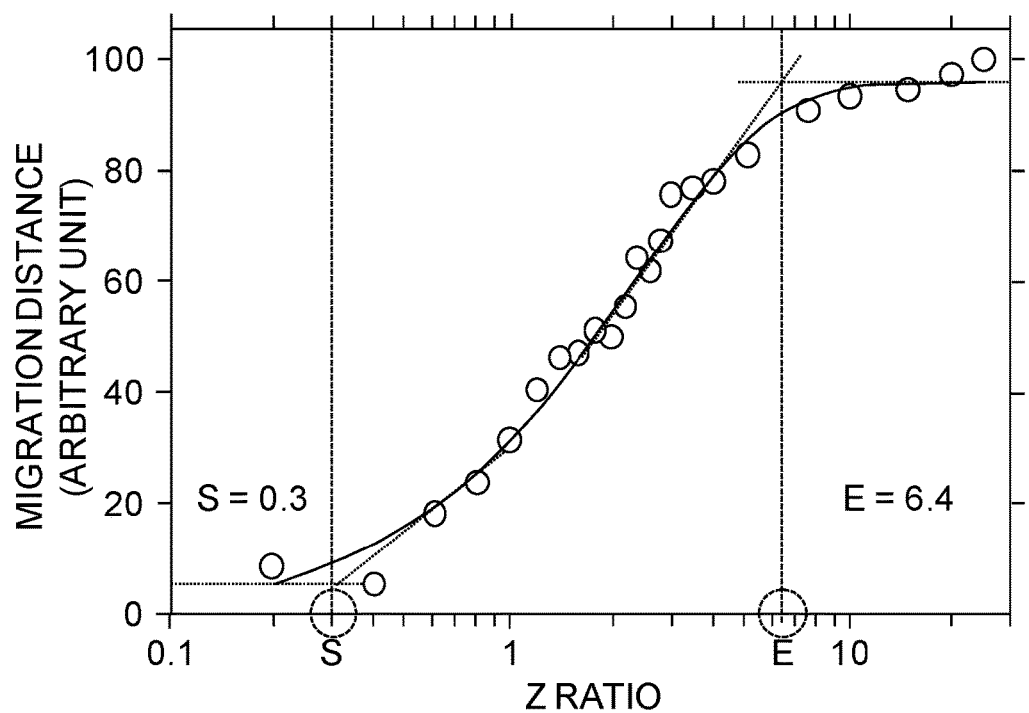

Horizontal electrophoresis was carried out to assess charge saturation. Horizontal electrophoresis indicates charge conversion of BDNF as a result of complex formation with PEG-PGA. BDNF in the native state stayed in the vicinity of where it was loaded and did not migrate much on the gel. As the fraction of PEG-PGA in the formulation increased, more and more BDNF migrated towards the cathode (FIG. 4). The saturation point of Z ratio appears to be about 6 rather than the 1:1 charge ratio that might be expected. Therefore, not all charges on the polymer or polypeptide have participated in the complex formation, suggesting the possibility that this system also works with same-net-charge polyion pairs, as long as the net charges involved in the binding reaction are opposite.

Figure 5:
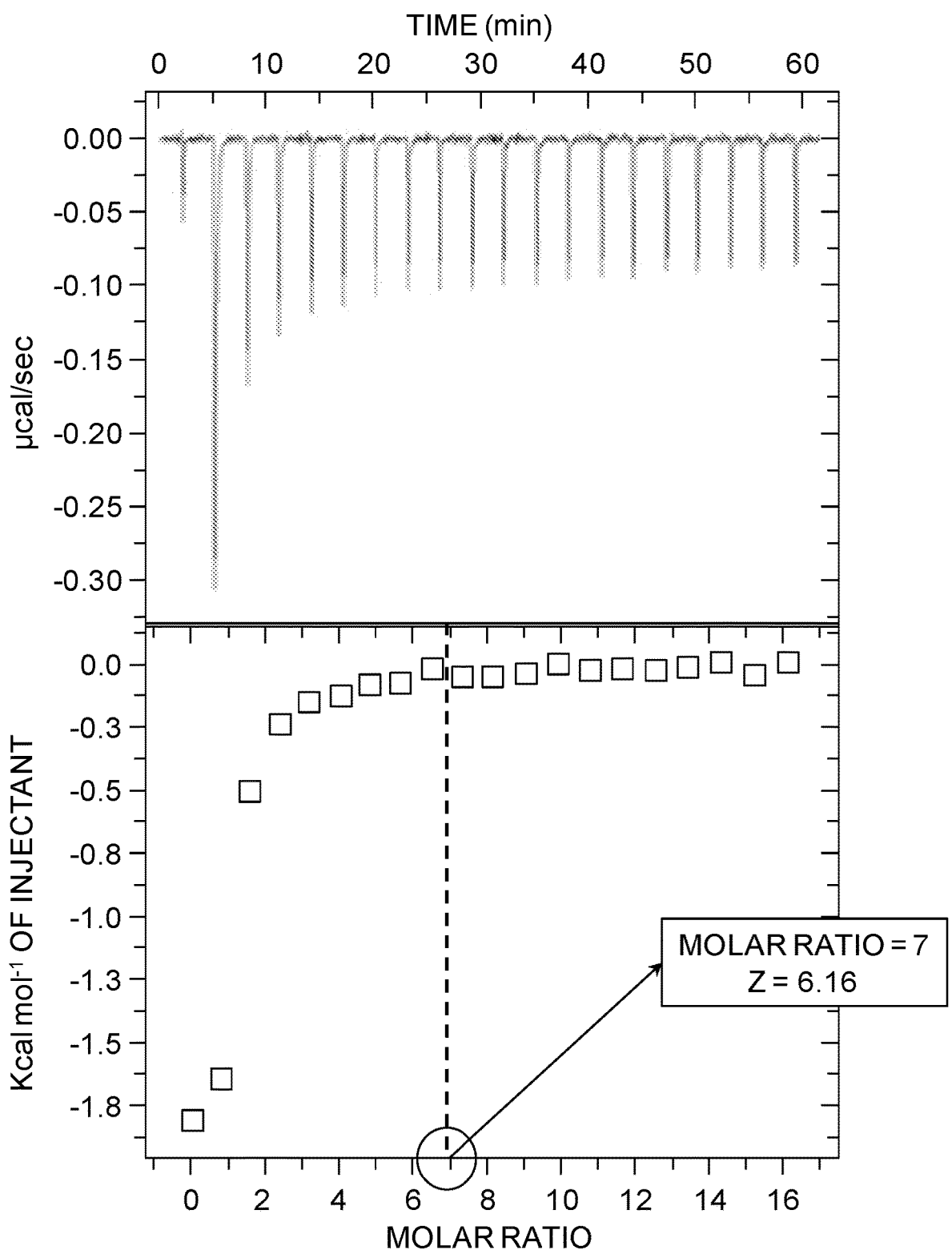
FIG. 5 shows charge saturation analysis by isothermal titration calorimetry.

The saturation Z ratio was confirmed by isothermal titration calorimetry. PEG-PGA was slowly titrated into a solution of BDNF at room temperature, and the reaction heat related to the binding between the two species was recorded and shown in FIG. 5. The results show that when PEG-PGA is gradually titrated into a solution of BDNF, the system stopped releasing heat at about Z ratio 6. This result further confirmed the saturation Z ratio measured in FIG. 4 (agarose gel electrophoresis experiment).

Figure 6:
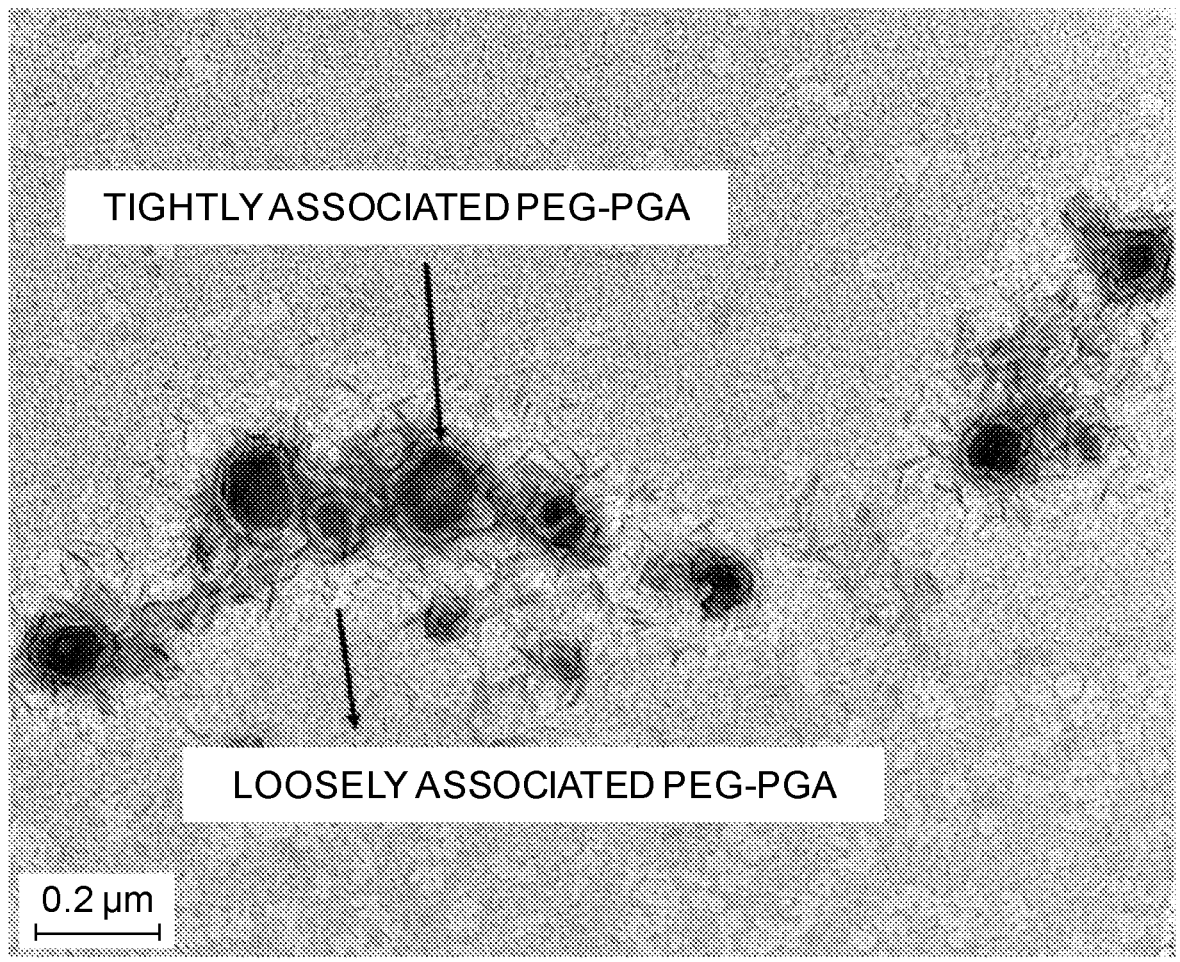
FIG. 6 shows dissociation of excess polymer from nano-BDNF upon dehydration on TEM carbon film.

Analysis of the TEM image (FIG. 2) provides further evidence to support the excess of PEG-PGA in the polymer (Z ratio more than 1:1). When nano-BDNF is deposited on a carbon membrane for the TEM experiment, it actually goes through a dehydration process. When this happens, some of the loosely associated PEG-PGA polymer are dissociated from the complex (FIG. 6). They are loosely associated because they do not bind to BDNF with their full charge.

Example 2

Release of BDNF from Polyelectrolyte Complexes

Figure 7B:
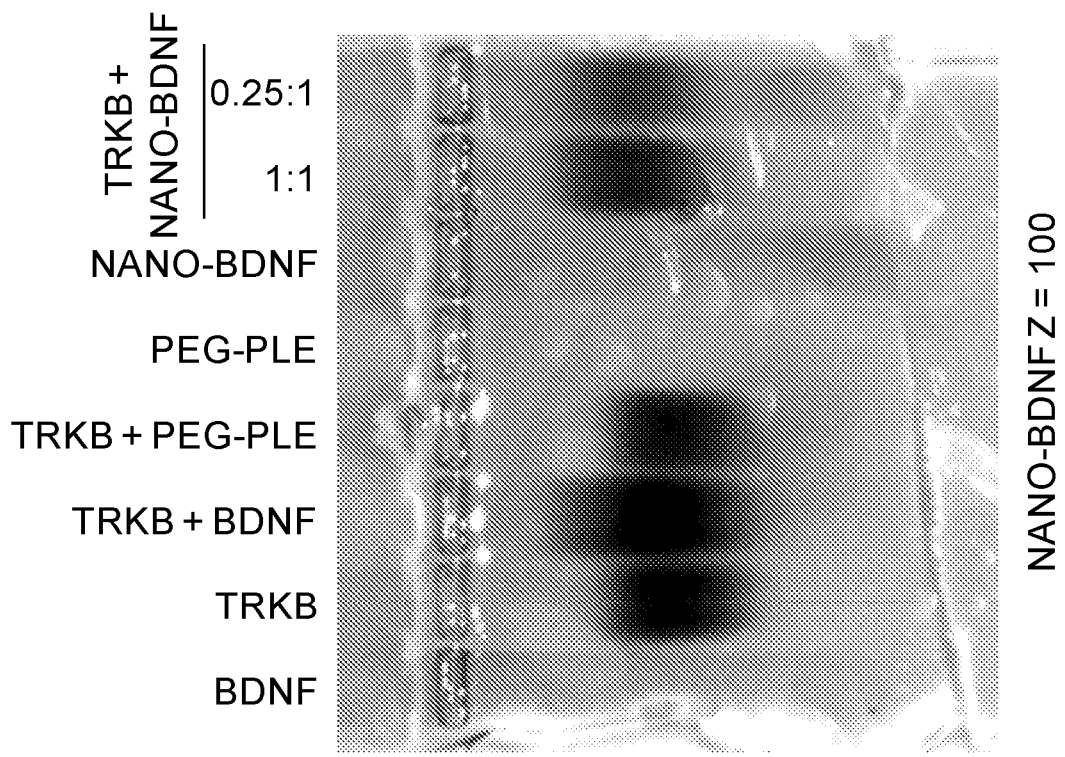
FIGS. 7A-7B show that BDNF is released from the complex upon TrkB binding.
Figure 7A:
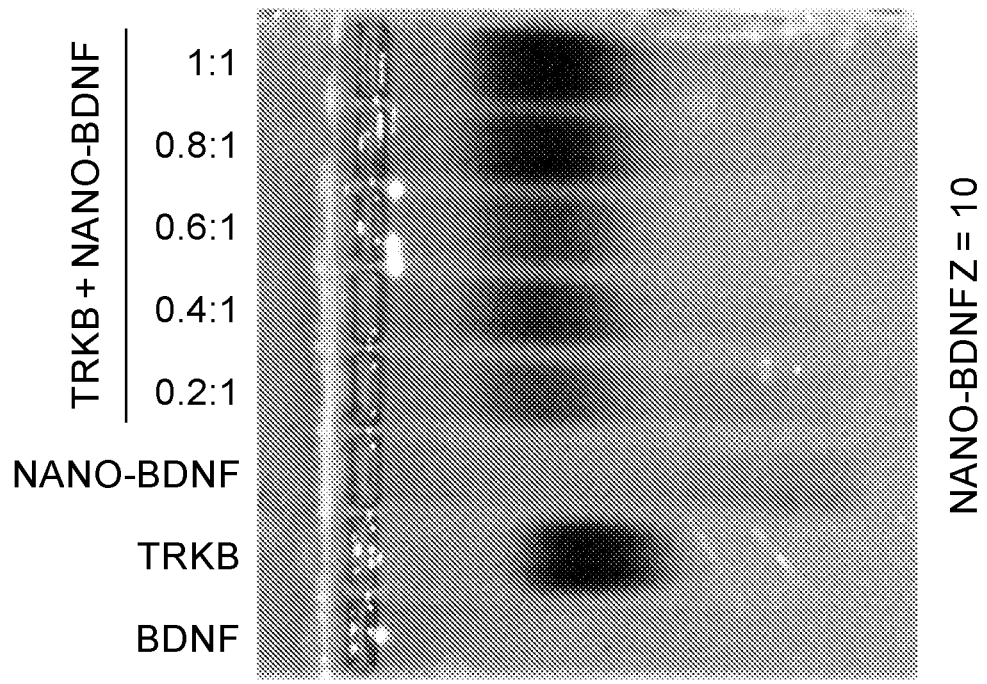

Native BDNF and nano-BDNF were run on an agarose gel in the presence of different amounts of TrkB, the receptor for BDNF (FIG. 7A). The smear of nano-BDNF (Z=10) gradually disappeared as increasing amounts of TrkB were added, indicating that BDNF is released from the complex upon TrkB binding. Complexes made at Z=100 behaved in a similar manner (FIG. 7B). The data show that TrkB appeared at a certain distance from the loading well. After mixing with either native BDNF or nano-BDNF, the migration distance of TrkB turned shorter, indicating increased positive charge, or size, or both, which can be explained by binding with BDNF. The smear of nano-BDNF became less intense as TrkB was gradually added into the mixture, indicating disruption of the complex. This disruption was observed in both Z=10 and Z=100 complexes.

Figure 8C:
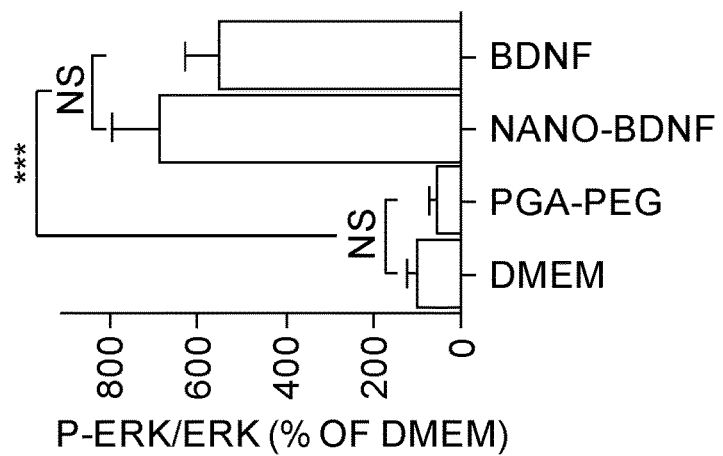
FIGS. 8A-8C show nano-BDNF retains BDNF ability to activate BDNF receptor, TrkB in vitro.
Figure 8B:
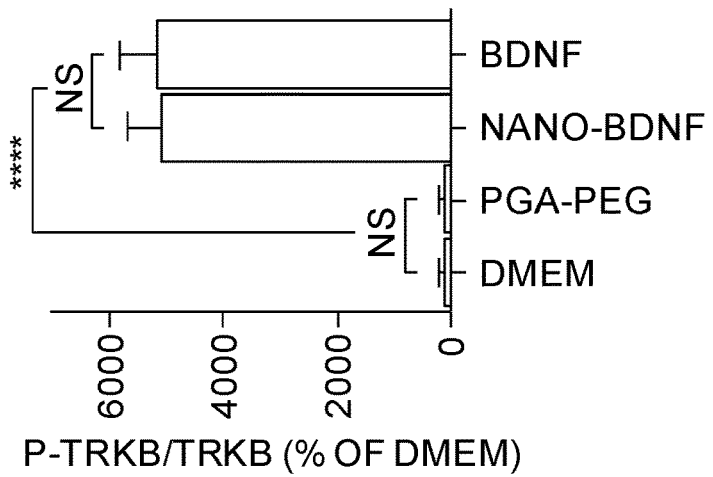
Figure 8A:
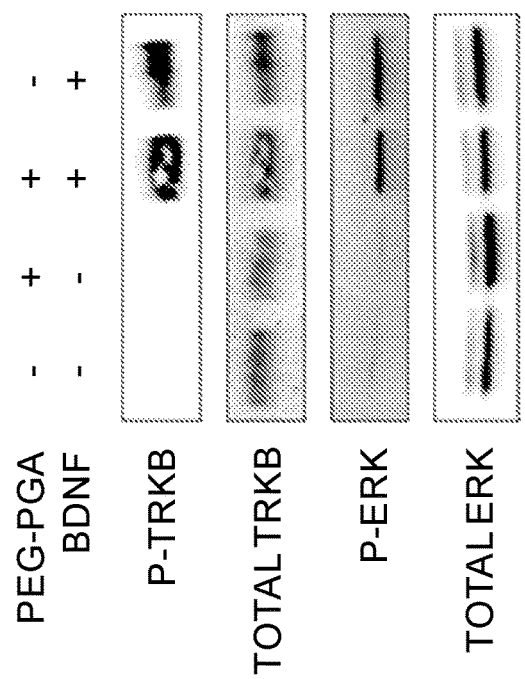

The activity of BDNF in nano-BDNF was tested. NIH3T3 cells stably expressing TrkB were treated with plain medium, PEG-PGA, BDNF or nano-BDNF for 5 min. before being lysed on ice. Lysates were subjected to western blot analysis to determine levels of phosphorylated TrkB (p-TrkB) or ERK (p-ERK) (FIG. 8A). The optical density ratio of p-TrkB over total TrkB was calculated and normalized to the level of DMEM group (FIG. 8B). The activation of ERK pathway, which is downstream of TrkB, was also quantified and normalized to the level the DMEM group (FIG. 8C) (*$p<0.001$, **$p<0.0001$, ns not significant).

Figure 9A:
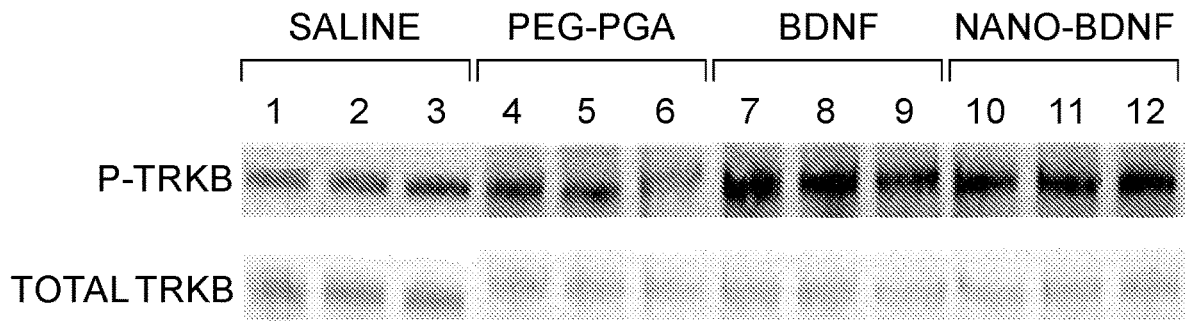
FIGS. 9A-9B show nano-BDNF retains BDNF ability to activate TrkB receptor in the brain.
Figure 9B:
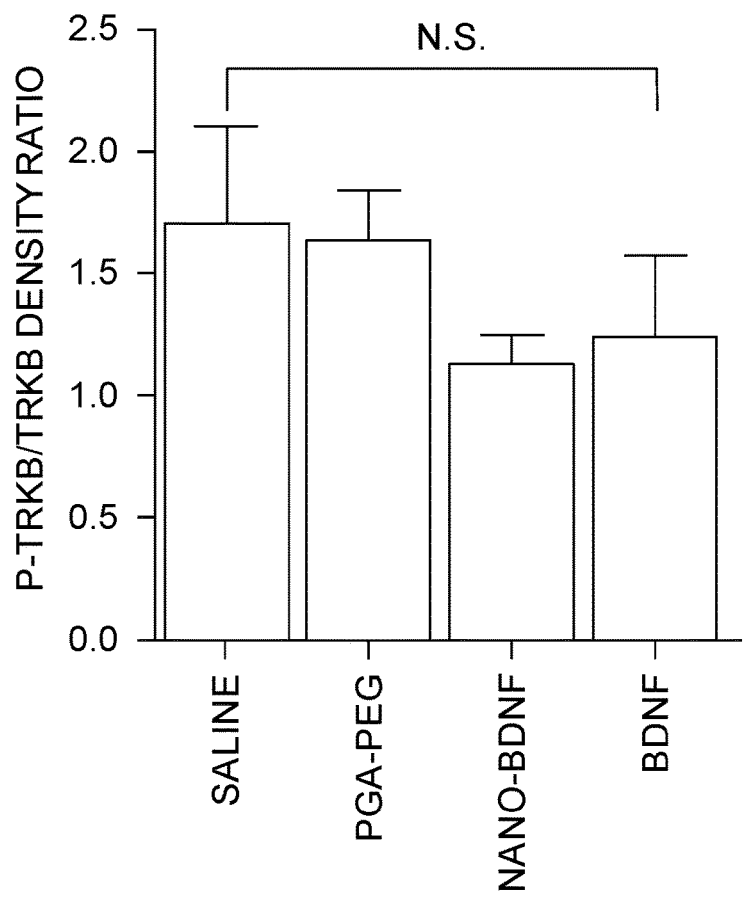

In a further experiment, saline, PEG-PGA, BDNF or Nano-BDNF were ICV injected into CD1 mice. Mice were sacrificed 30 min. later and mice brains were homogenized, immunoprecipitated with anti-TrkB antibody, and subjected to western blot analysis (FIG. 9A). The optical density ratio of p-TrkB over total TrkB was calculated and normalized to the level in the saline group (FIG. 9B). The saline and vehicle p-TrkB levels are due to presence of endogenous BDNF in healthy mice.

It has been important to evaluate whether delivery of BDNF in a "nano-container" form to the brain (even if improved in terms of amount in the brain compared to free BDNF) might be offset by slow release of active BDNF from the carrier. While the Nano-BDNF is designed to improve stability of the protein in blood, importantly, it is completely released upon interaction with the TrkB receptor in the brain. As a result, as can be seen in FIGS. 8 and 9, the activity of nano-BDNF with respect to the receptor is the same as that of the native BDNF. In this regard, the Nano-BDNF technology is unique compared to other carrier-based approaches for delivery of polypeptides that do not exhibit triggered release of neurotrophins upon interaction with the receptor.

Example 3

Stabilization of BDNF in Polyelectrolyte Complexes

Figure 10A:
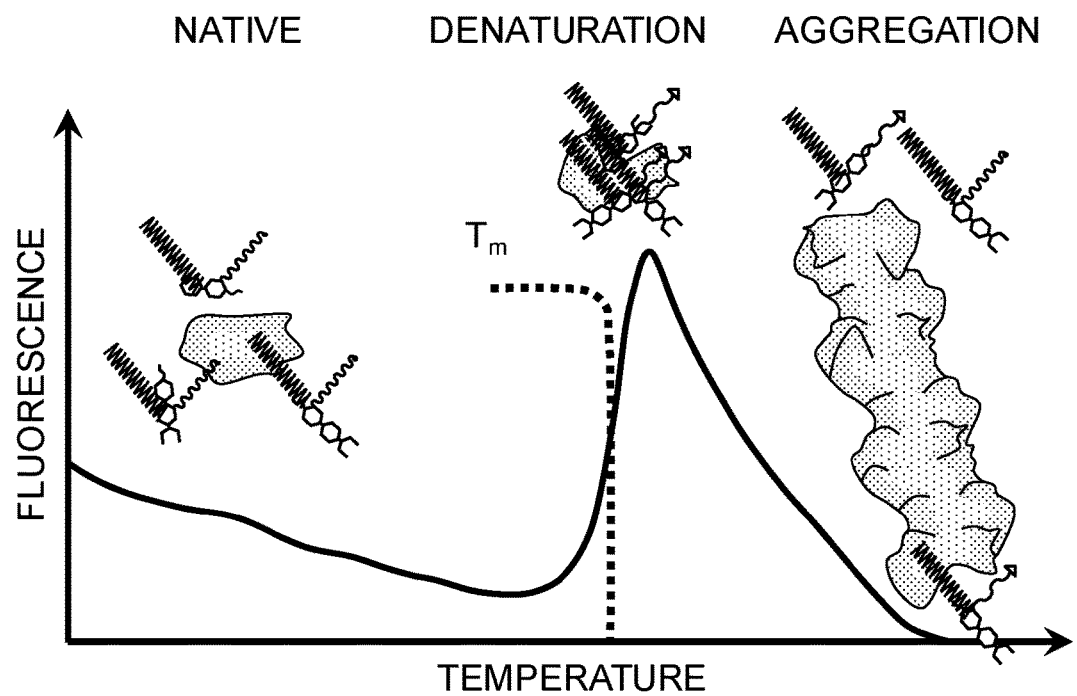
FIGS. 10A-10B show that PEG-PGA increased the intrinsic stability of BDNF.
Figure 10B:
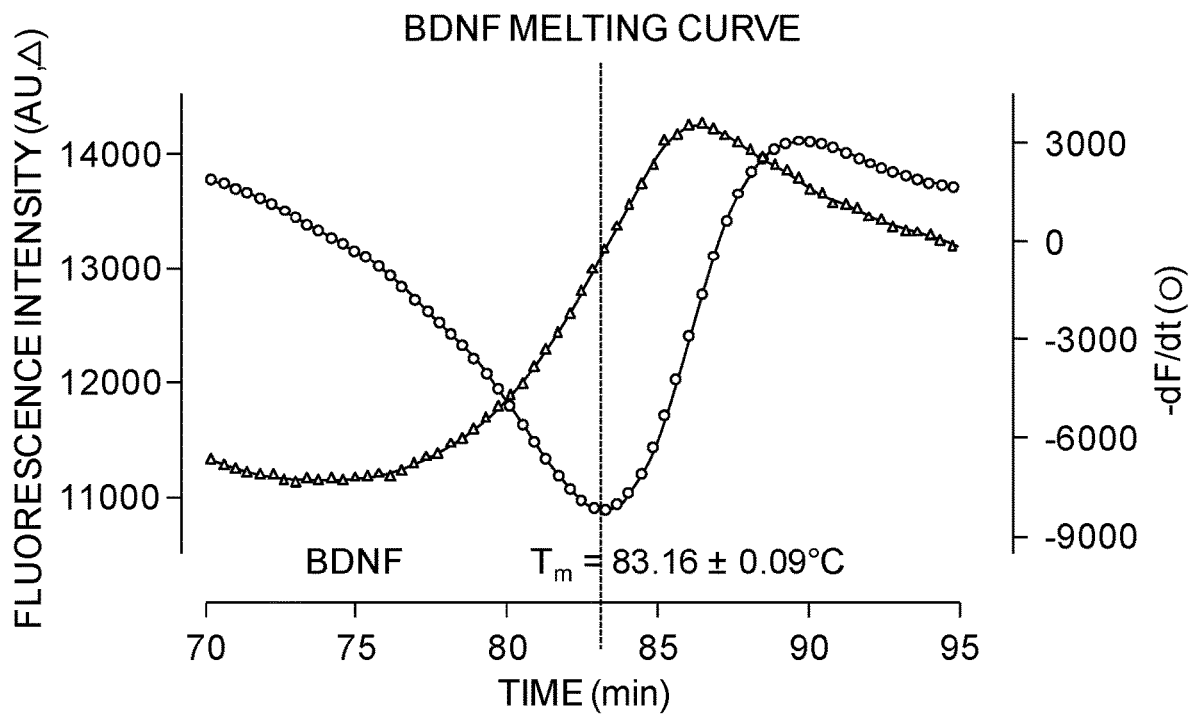

To determine the stability of BDNF in a polyelectrolyte complex, the melting temperature (temperature at which the protein starts to unfold and denature) of native BDNF was measured in a protein thermal shift assay kit (Invitrogen) according to the manufacturer's protocol. BDNF has a melting temperature of about 83° C. (FIGS. 10A-10B). This temperature is reflective of its intrinsic stability.

Figure 11A:
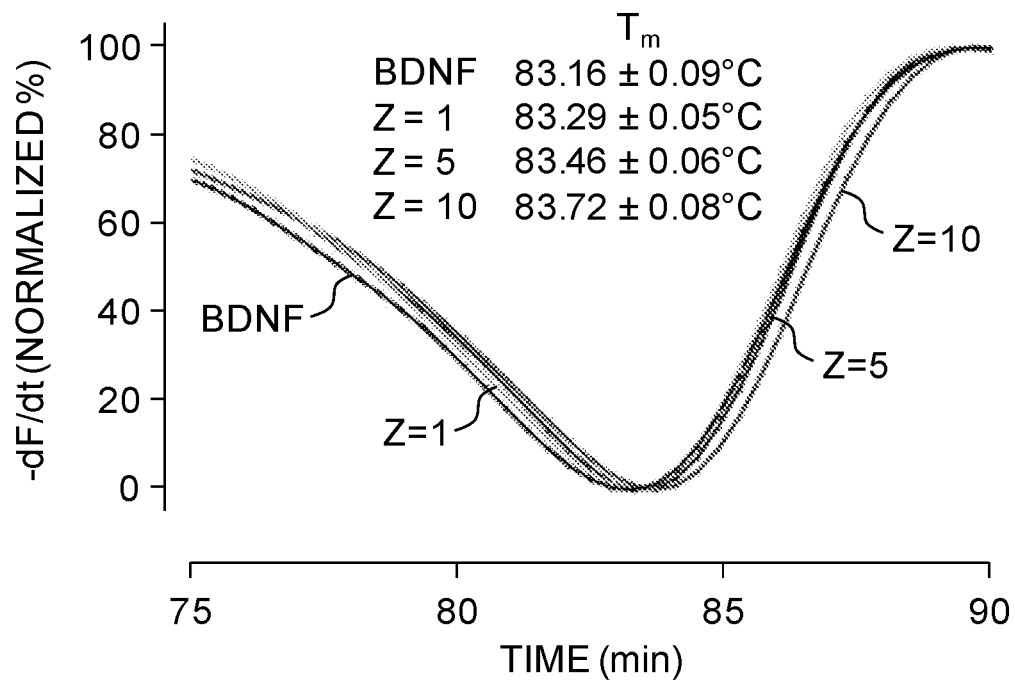
FIGS. 11A-11B show the intrinsic stability of BDNF with increasing Z ratio.
Figure 11B:
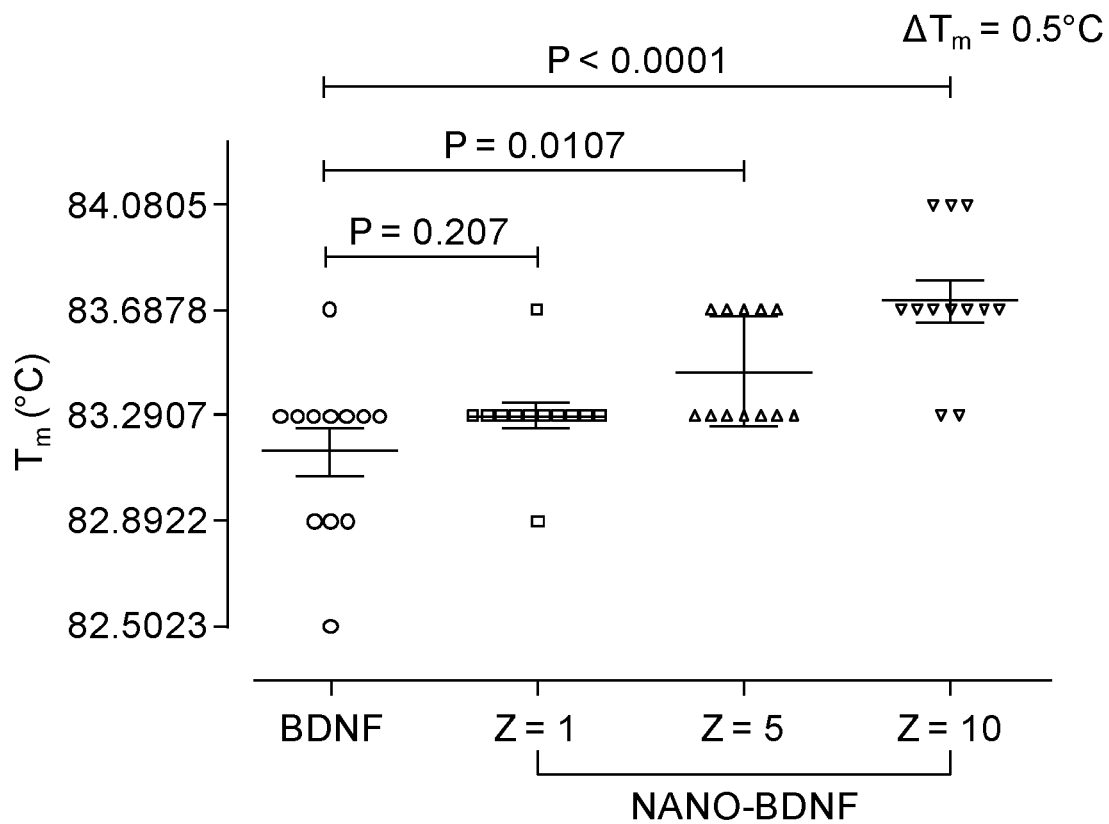

Next, the melting temperature of nano-BDNF at different Z ratios (1, 5, and 10) was measured and compared with that of native BDNF (FIGS. 11A-11B). As the Z ratio increased in nano-BDNF complex, we observe increased intrinsic stability of BDNF. In the Z=10 group where the complex is believed to reach a saturated state, we observed an increase of 0.5° C. in the unfolding temperature of BDNF.

Figure 12:
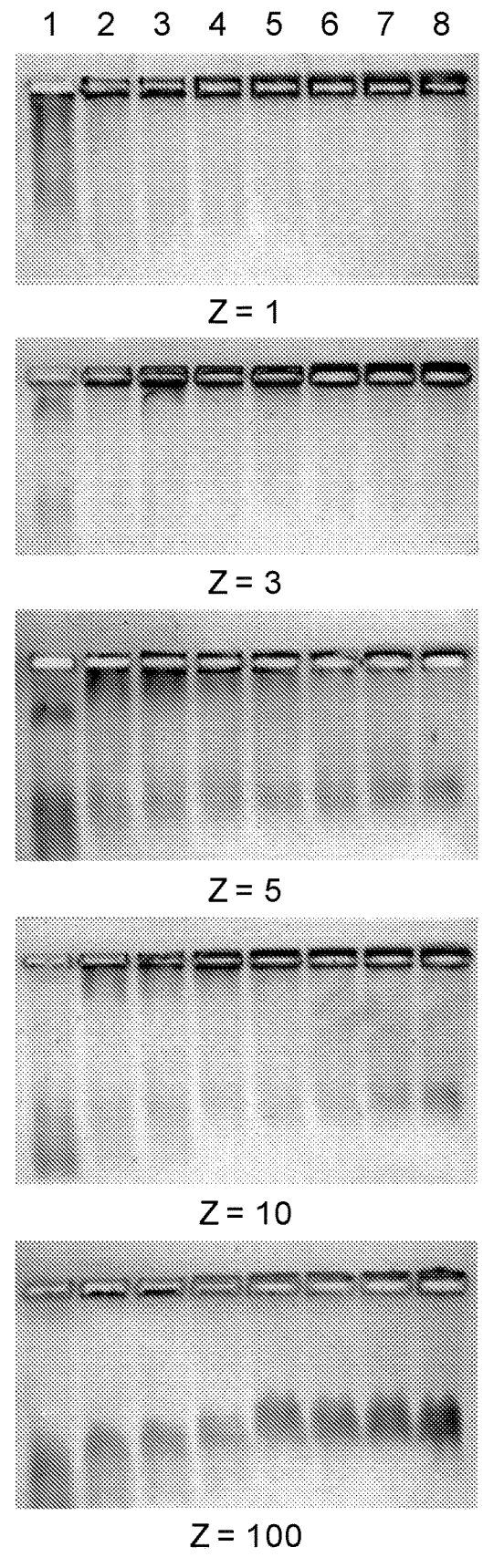
FIG. 12 shows a NaCl challenge on nano-BDNF at different Z ratios.

The colloidal stability of nano-BDNF was tested. nano-BDNF prepared at Z ratios of 1, 3, 5, 10, and 100 were subjected to NaCl challenge at a series of NaCl concentrations (Lane 1-8: 0, 0.15, 0.30, 0.45, 0.60, 0.75, 0.90, 1.05M, respectively) before running on an agarose gel (FIG. 12). From the results, one can tell that the colloidal stability of nano-BDNF is related to the Z ratio of the complex. At Z ratio 1, the complex is completely destroyed and native BDNF starts to bind to the edge of the wells again. At Z=3 we start to see two different species, the slower migrating species apparently bears less charge, and could be the intermediate species between BDNF and nano-BDNF, which migrates faster. Both of the two species are not resistant to salt challenge. Nano-BDNF made at Z ratio 10 looks similar to Z ratio 5, except that the slowly migrating species disappeared. When it comes to Z ratio 100, we see a much more prominent slowly migrating species. It seems that in addition to the excess Z ratio, the unbound PEG-PGA polymer in the solution does provide some additional protection on BDNF in terms of preventing its interaction with the surrounding (in this case agarose gel).

Example 4

Intranasal Delivery of Nano-BDNF

Figure 13:
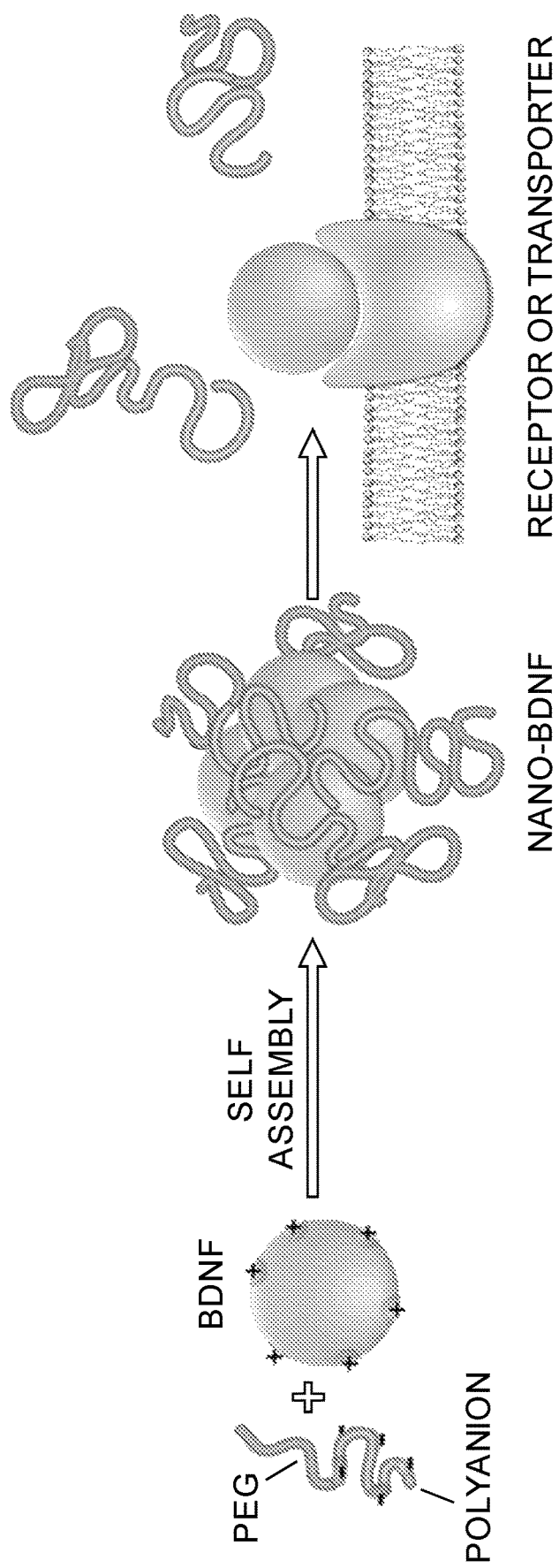
FIG. 13 shows that nano-BDNF spontaneously forms in water upon simple mixing of the native BDNF and PEG-PGA copolymer.

This example describes the development of a BDNF formulation ("nano-BDNF") that, after intranasal administration, displays increased brain uptake and region specific distribution as compared to native protein. Indeed, this novel formulation exhibits greatly increased uptake into the brainstem and hippocampus—two regions of particular importance to Rett syndrome (RTT) pathology (Li et al., *Proc. Natl. Acad. Sci. USA* 109:17087 (2012)). By entrapping the BDNF protein molecule in a nanoscale size (under 100 nm) polyion complex we created the nano-BDNF formulation (FIG. 13). Nano-BDNF spontaneously forms in water upon simple mixing of the native BDNF and PEG-PGA copolymer. BDNF electrostatically couples with the oppositely charged PGA chain and entraps into a particle core surrounded by a shell of uncharged water-soluble PEG. Active BDNF is released upon interaction with cell receptor.

By forming the nano-BDNF formulation we are able to: 1) increase the stability of BDNF within nasal mucosa, 2) minimize BDNF serum exposure and peripheral distribution, 3) increase BDNF delivery to the brain regions affected by the disease, and 4) release active BDNF in these regions allowing its interaction with target receptors. This invention is innovative in several aspects. Firstly, approaches using polymer-based nano-formulations to improve intranasal-to-brain (INB) delivery of polypeptides and especially directing nasal biotherapeutics to certain brain regions relevant to their biological function are a largely unexplored area of drug development. Such "targeted" approaches may be of particular importance for nasal delivery of neurotrophins such as BDNF since it may decrease the off-target effects (Nagahara et al., Nat. Rev. Drug Discov. 10:209 (2011)). Second, in contrast to other drug delivery approaches involving incorporation of polypeptides in nanoparticles, a hallmark of our approach is the simplicity of nano-BDNF preparation using mild, non-denaturing aqueous conditions; thereby avoiding the use of organic solvents and other potentially toxic reagents commonly used in nanotechnology-based formulations. Significantly, the block copolymer chemistry employed in the nano-BDNF formulation contains two biocompatible materials, PEG and PGA, both of which have been approved by the FDA (PEG as an inactive ingredient in pharmaceutical preparations and PGA as a GRAS food additive). In addition, small molecule drugs that contain PGA as a conjugate are in clinical trials. However, neither the polymers and the anionic block copolymers, nor the polyion complexes on the base of these copolymers were employed thus far in efforts to improve INB delivery of proteins to the brain (Yi et al., J. Controlled Release 190:637 (2014)). The simple and original design of nano-BDNF is readily scalable for producing amount required for clinical testing. The INB delivery of nano-BDNF could substantially simplify treatment of RTT compared to direct but more invasive methods of BDNF delivery (e.g., intrathecal) to the CNS. This novel approach to delivering proteins to the brain should serve as a platform for design of therapeutics to treat other neurological disorders.

Figures 14A, 14B, 14C:
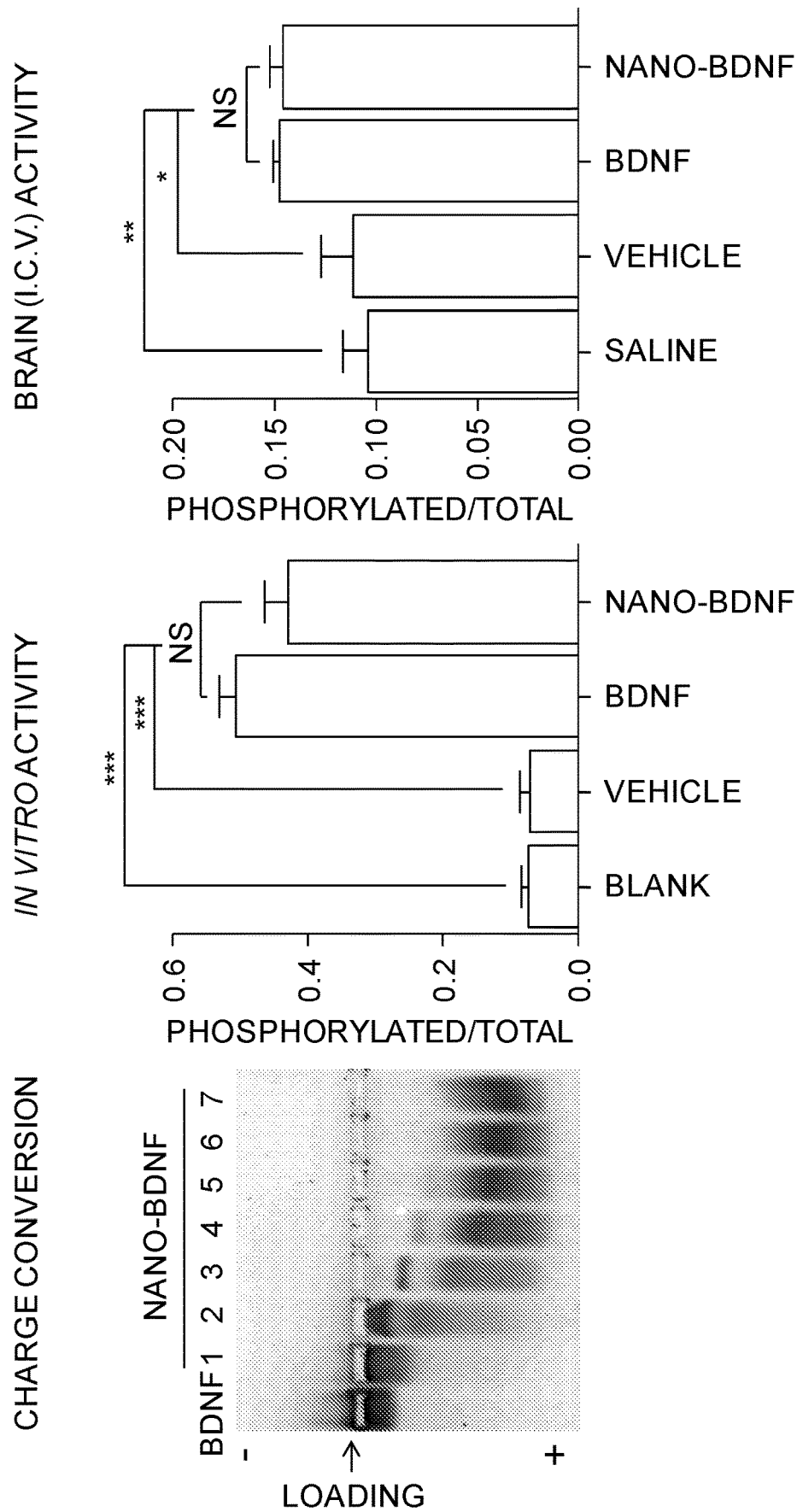
FIGS. 14A-14C show formation of nano-BDNF and comparison of activity with native protein.

BDNF exists mainly as a dimer (28 kDa) having a net positive charge at physiological pH. We prepared the nano-BDNF formulation by mixing anionic $PEG_{113}$-$PGA_{50}$ (13 kDa) with rhBDNF in aqueous media at different charge ratios. Polyion coupling resulted in the conversion of the charge as seen by PAGE (FIG. 14A). Charge conversion is displayed in lanes 3-7 by complex migration towards the anode in a horizontal agarose gel; lanes 1-7 were loaded with nano-BDNF at $Z_{BDNF/PGA}$ ratios 0.5, 1, 2, 5, 10, 20, and 100. Dynamic light scattering (DLS) revealed a particle size of 95 nm with a small polydispersity index (PDI) of 0.165 (0.1 mg/mL BDNF in de-ionized water); the particles remained stable in aqueous dispersion for days. The biological activity of nano-BDNF was nearly the same as that of the equivalent dose of native rhBDNF as determined, in vitro, by the phosphorylation of TrkB in NIH-3T3-TrkB cells and, in vivo, after intracerebroventricular (ICV) injection (FIGS. 14B and 14C). Nano-BDNF is nearly as active as native rhBDNF in inducing phosphorylation of TrkB in NIH-3T3-TrkB cells (FIG. 14B) and in vivo after i.c.v. injection of 1 µg per CD1 mouse (FIG. 14C) (by Western blots). Data were analyzed with unpaired students' t-test, *: $P<0.05$; : $P<0.01$; *: $P<0.001$; NS—not significant.

Figure 15:
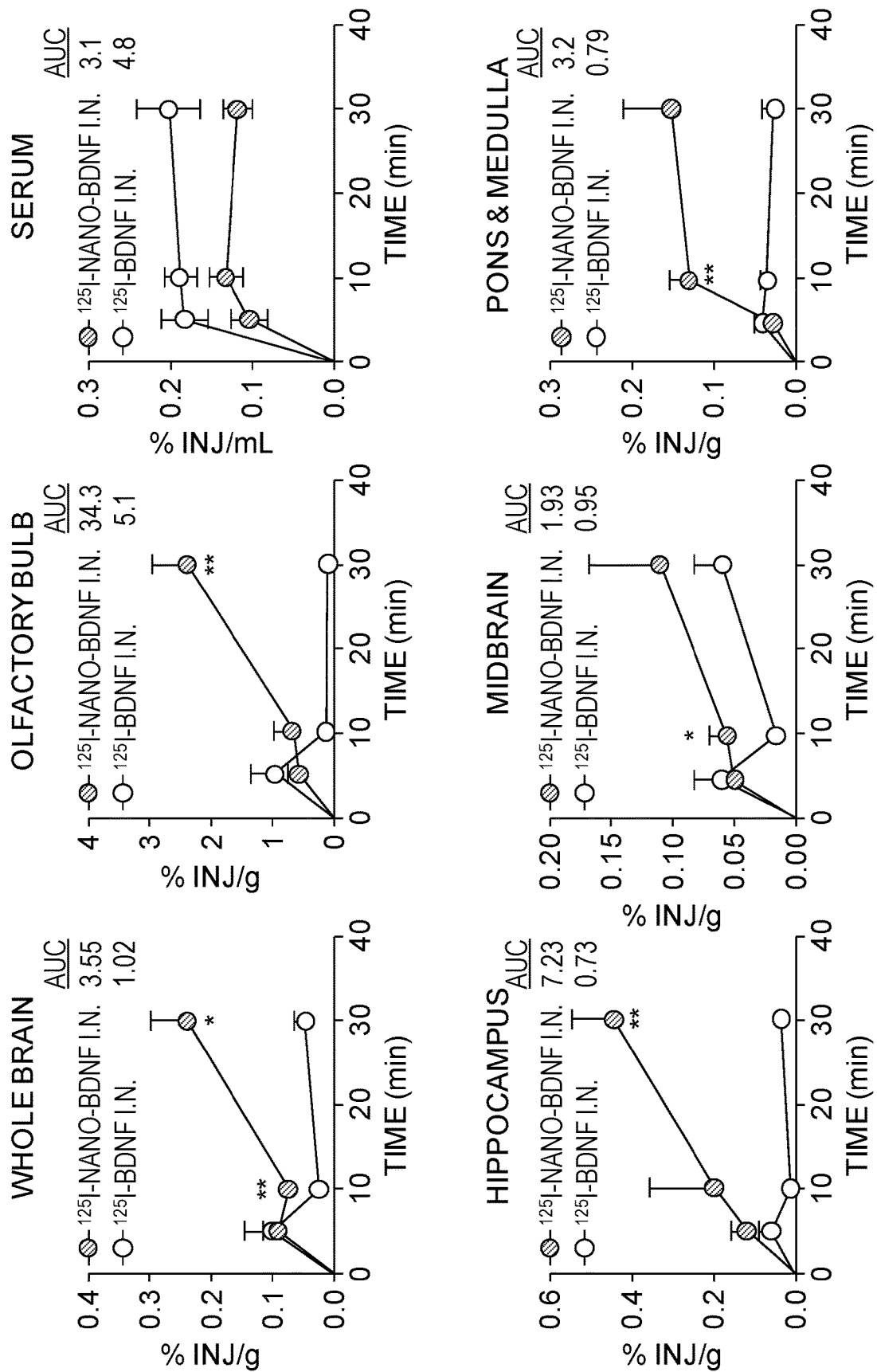
FIG. 15 shows uptake of $^{125}$I-BDNF and $^{125}$I-nano-BDNF in brain regions, whole brain and serum over 30 min after INB delivery.
Figure 16:
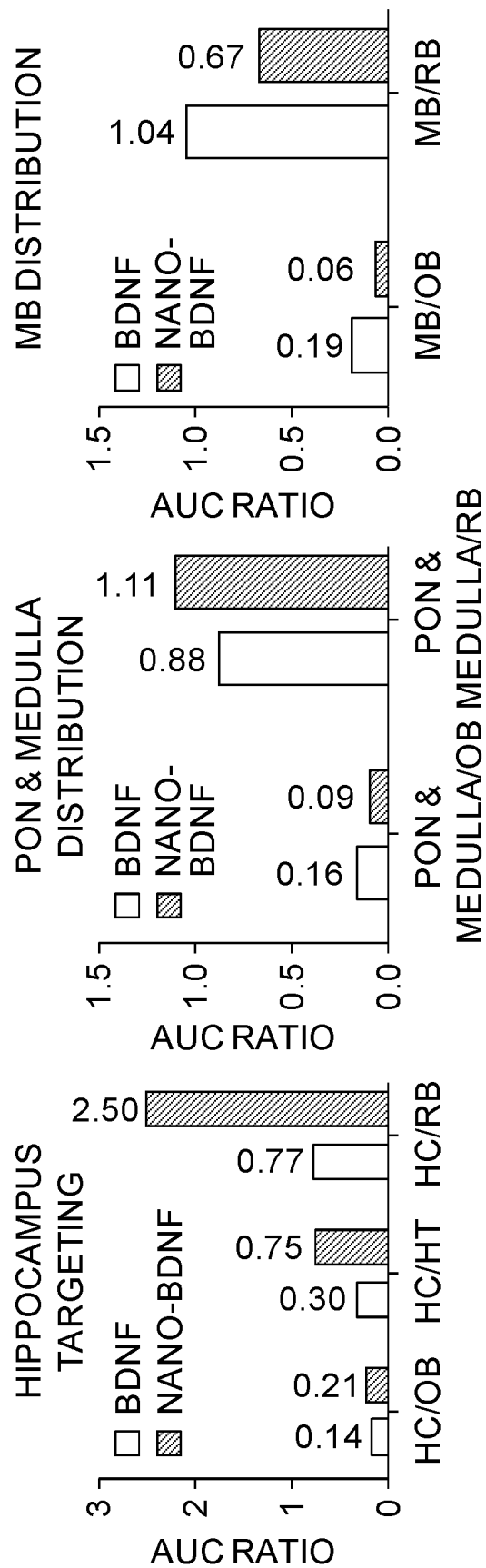
FIG. 16 shows nano-BDNF distribution in brain regions after INB delivery compared to rhBDNF.

Following intranasal administration, nano-BDNF shows increased brain uptake and hippocampus targeting relative to native BDNF. The rhBDNF was labeled by $^{125}I$ and then formulated with $PEG_{113}$-$POA_{50}$ to form $^{125}I$-nano-BDNF. A trace amount ($10^6$ cpm/mouse) of $^{125}I$-labelled nano-BDNF or native rhBDNF was administered INB into CD-1 mice. Radioactivity levels in the blood, brain, and brain regions were measured up to 30 min after the administration. In FIG. 15 it is demonstrated that $^{125}I$-nano-BDNF uptake in the whole brain, olfactory bulb, hippocampus, and brainstem (midbrain, pons and medulla) was dramatically increased compared to that of $^{125}I$-rhBDNF. Significant differences was observed between BDNF and nano-BDNF *, $p<0.05$; **, $p<0.01$. By dividing the areas under the curve (AUC) for different brain regions we further concluded that relative to native rhBDNF, the brain regional distribution pattern of nano-BDNF was very different. Specifically, there was an increase of nano-BDNF distribution to hippocampus vs. olfactory bulb, hypothalamus and the rest of the brain (FIG. 16). In contrast, the distribution to pons and medulla was only slightly increased vs. the rest of the brain, while the relative distribution to the midbrain was decreased vs. both olfactory bulb and the rest of the brain. The data presents AUC ratios for the hippocampus (HC), pons (PON) and medulla, and midbrain (MB) vs. olfactory bulb (OB), hypothalamus (HT), and "rest of the brain" (RB) defined as all brain regions excluding HC and brainstem.

Figure 17:
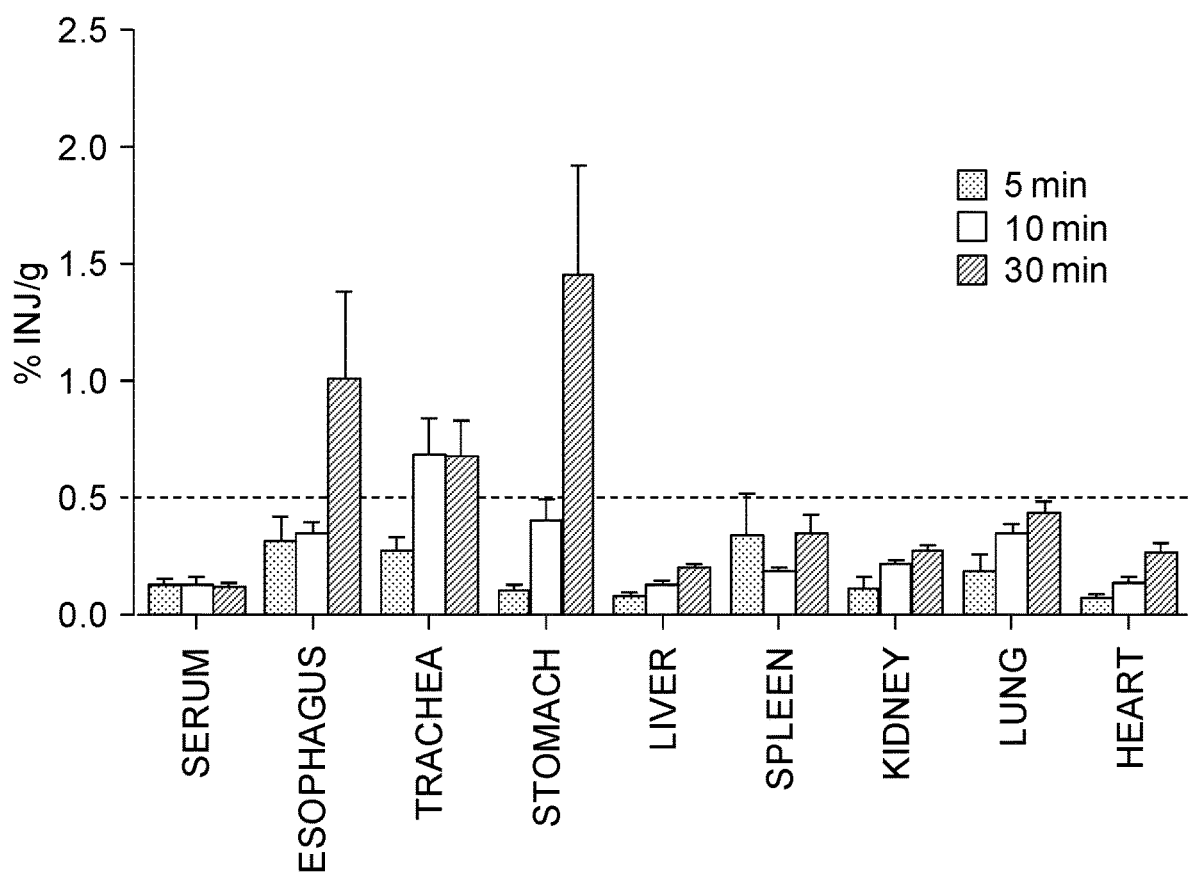
FIG. 17 shows nasal nano-BDNF peripheral organ distribution.
Figure 18:
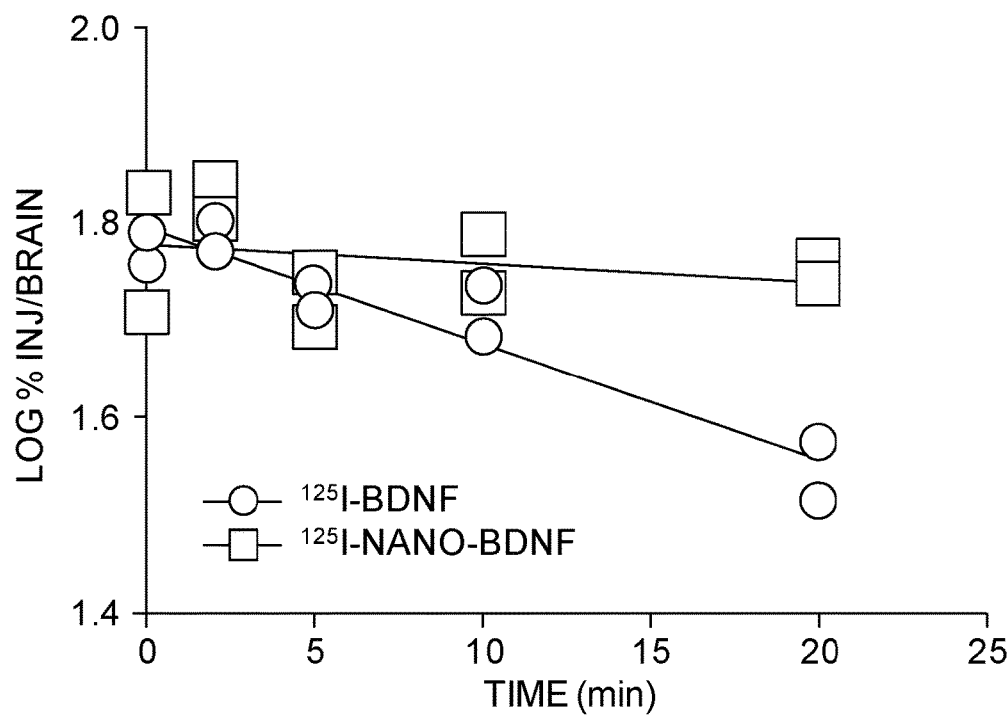
FIG. 18 shows brain efflux of $^{125}$I-BDNF or $^{125}$I-Nano-BDNF after ICV injection.

Following intranasal administration, distribution of nano-BDNF into the serum and uptake by peripheral organs is limited. In FIG. 15 it is also demonstrated that the amount of nano-BDNF distributed in the serum after intranasal administration was lower than native rhBDNF. Analysis of the peripheral distribution of nano-BDNF suggests that within 30 min following INB delivery, nano-BDNF was detected in liver, spleen, kidney, lung and heart—albeit at levels less than 0.5% inj/g. Marginally higher amounts of the INB delivered nano-BDNF were found in the esophagus, trachea, and stomach but these amounts still were in the range of 1-2% inj/g tissue (FIG. 17) and were likely due to limitations of our INB procedure in a mouse ("post nasal drip"). In addition, literature (Pan et al., Neuropharmacology 37:1553 (1998)) as well as our own studies suggest that there is a brain-to-blood efflux mechanism for native BDNF (FIG. 18). However, we observed much less efflux of nano-BDNF from brain to blood when it was directly injected to cerebral ventricle relative to native BDNF (FIG. 18). The efflux rates displayed by the slopes of the lines were $-0.012\pm0.0014$ ($r^2=0.89$, n=26) for BDNF and $-0.0018\pm0.0023$ ($r^2=0.07$, n=30) for nano-BDNF. Both slopes are significantly 1) non-zero and 2) different from each other. This observation may help to explain why despite the increased accumulation of nano-BDNF in the brain, its release into the serum was not increased to the same extent. Overall, our data suggest that nano-BDNF delivered by the INB route has improved delivery to regions of the brain (the brainstem and hippocampus) that are important targets for RTT therapeutics. Moreover, the relatively low distribution to the blood and peripheral organs should decrease the risk of side effects associated with systemic exposure to nano-BDNF. Taken together our data represent a compelling rationale for advancing the development of nano-BDNF as a treatment for RTT and other CNS disorders.

Example 5

Pharmacokinetics of Nano-BDNF

Figures 19A, 19B, 19C:
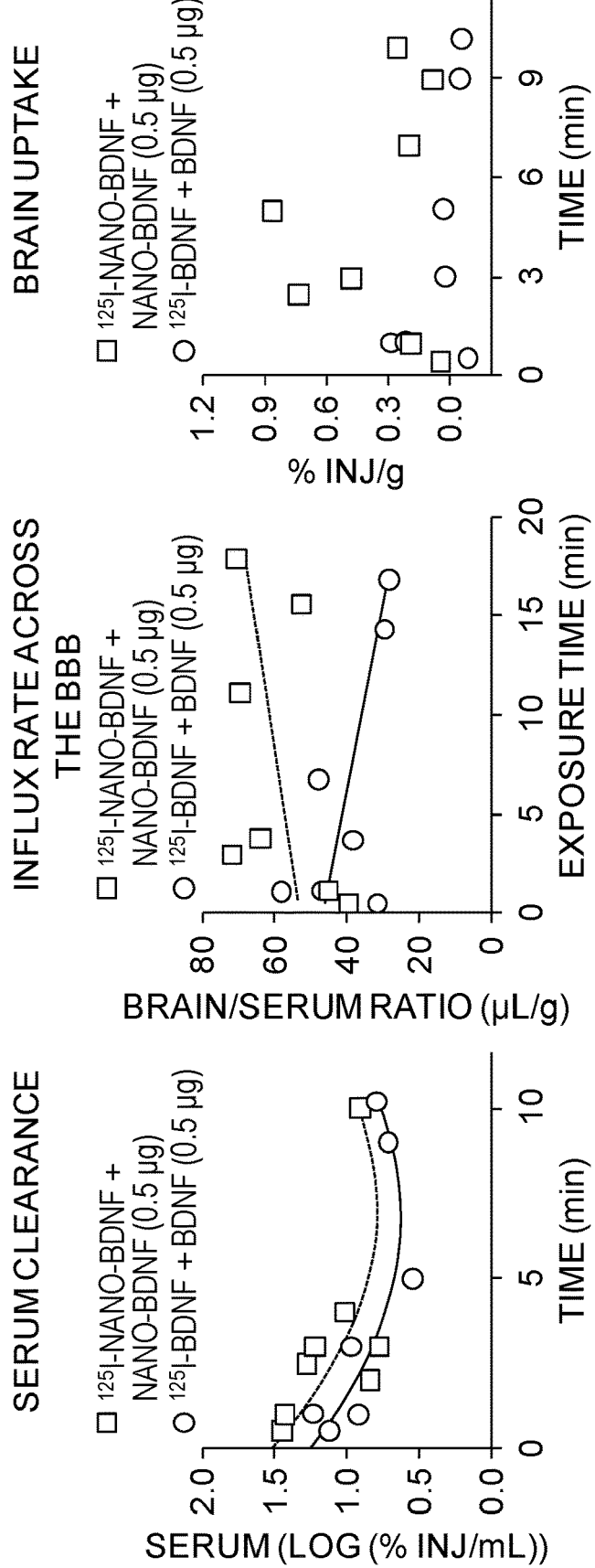
FIGS. 19A-19C depict a brain pharmacokinetics study showing that (A) nano-BDNF clears from the circulation similarly to native BDNF; (B) nano-BDNF displays net influx (Ki=0.84 uL/g·min) into the brain, whereas native BDNF displays a net efflux from brain to the blood; (C) consequently nano-BDNF displays higher brain uptake than native BDNF, as shown by AUC of 2.96 for nano-BDNF vs 0.54 for native BDNF. The native BDNF or nano-BDNF were injected IV at a single dose of 25 μg/kg. In Plot B, the slope and Y-intercept of the brain/serum ratio determine the Ki (influx rate) and Vi (initial volume of distribution) of the drug, respectively. The negative slope for the native BDNF (negative influx rate) means that there is efflux of native BDNF from the brain. In the case of nano-BDNF, the slope is positive suggesting that there is net influx. Since this is a single bolus injection experiment the ratio changes over time.

The pharmacokinetics of nano-BDNF after IV administration is shown in FIGS. 19A-19C. The brain/serum ratio (µl/g) over time after IV administration of BDNF and nano-BDNF is presented in FIG. 19B. Since this is a single bolus injection experiment the ratio changes over time. From the data provided in FIG. 19C, the exact difference in the total brain AUC after IV administration of the nano-BDNF vs. BDNF in this experiment is 5.48 times. This is computed based on the whole brain uptake of BDNF.

The results of the brain PK study show that (A) nano-BDNF clears from the circulation similarly to native BDNF; (B) nano-BDNF displays net influx (Ki=0.84 µL/g·min) into the brain, whereas native BDNF displays a net efflux from brain to the blood; (C) consequently nano-BDNF displays higher brain uptake than native BDNF, as shown by an AUC of 2.96 for nano-BDNF vs. 0.54 for native BDNF. The native BDNF or nano-BDNF were injected IV at a single dose of 0.5 µg/mouse.

In FIG. 19B, the slope and Y-intercept of the brain/serum ratio determine the $K_i$ (influx rate) and Vi (initial volume of distribution) of the drug, respectively. The negative slope for the native BDNF (negative influx rate) means that there is efflux of native BDNF from the brain. In the case of nano-BDNF, the slope is positive suggesting that there is net influx. In a separate study after intracerebroventricular (ICV) administration of the corresponding formulations of BDNF in mice, we demonstrated the efflux of native BDNF that was greatly diminished for nano-BDNF (FIG. 18)), which is consistent with the data in FIG. 19B. We believe that the decreased efflux of nano-BDNF from the brain contributes to its increased accumulation compared to native BDNF after both IV and INB administration.

Data on INB administration for whole brain uptake was also generated. The ratio of AUC for nano-BDNF and BDNF in this case is 3.48. In this study, we carried out a detailed analysis of distribution of nano-BDNF and BDNF in different brain regions and serum. The complete data set is presented in FIG. 15. Overall, these data suggest that nano-BDNF delivered by the INB route has improved delivery to regions of the brain (the brainstem and hippocampus) that are important targets for RTT therapeutics. For example, the ratios of AUCs for nano-BDNF and native BDNF in pons and medulla and hippocampus are 4.0 and 9.9, respectively.

In the cortex of the healthy mouse, the BDNF concentrations vary from ~5 to ~10 ng/mg (Zuccato et al. Systematic Assessment of BDNF and Its Receptor Levels in Human Cortices Affected by Huntington's Disease. Brain Pathology. 2008, 18, 225-38). In the Mecp2-deficient mouse, the BDNF levels in the nodose ganglia (NG) and cortex are lower by ~40% to ~50% compared to the healthy mouse levels (Wang et al. Dysregulation of brain-derived neurotrophic factor expression and neurosecretory function in Mecp2 null mice. The Journal of Neuroscience. 2006, 26, 10911-15). These changes are age dependent—as the behavioral impairments start to manifest around 5-6 weeks, BDNF levels are lower in caudal parts of the brain, such as the brainstem and cerebellum, without detectable changes in the cerebral cortex. By 7 weeks, BDNF levels are lower in male Mecp2-knockout mice throughout the entire brain (Li & Pozzo-Miller, BDNF deregulation in Rett syndrome, Neuropharmacology 2014, 76 737-46). Based on our PK data with a single IV injection of nano-BDNF the concentration delivered to the total brain of normal mice is in the range of ~1 to 4 ng/mg.

The BDNF concentrations measured in post mortem human cortex range from ~3.4 to ~14.3 pg/mg (Zuccato et al. Systematic Assessment of BDNF and Its Receptor Levels in Human Cortices Affected by Huntington's Disease. Brain Pathology 2008, 18 225-38). However, post mortem values may be significantly lower than the values in live humans due to long time of processing of post mortem tissues.

Example 6

Stroke Model of Nano-BDNF

Stroke is the fifth leading cause of death in the United States and is a leading cause of adult disability (Mozaffarian et al., *Circulation* 133(4):e38 (2016)). The long lasting impairments seen after stroke diminish independence and reduce quality of life in stroke survivors (Synhaeve et al., *Neurology* 85(9): 776 (2015)). In addition to physical disability and cognitive impairments, post stroke depression (PSD) is also a frequent and important neuropsychiatric consequence of stroke (Lokk et al., *Neuropsychiatr. Dis. Treat.* 6: 539 (2010)). About 40% of stroke survivors suffer from PSD (Lenzi et al., *Revue Neurologique* 164(10): 837 (2008)). PSD develops soon after stroke, and can persist for years and impair neurological recovery after stroke (Zavoreo et al., *Acta Clin. Croat.* 48(3): 329 (2009)).

Given that stroke significantly impairs quality of life, it is imperative to find treatments that improve functional recovery after stroke onset. Brain derived neurotrophic factor (BDNF) induces neuronal plasticity and plays an important role in post stroke rehabilitation and recovery (Mang et al., *Physical Therapy* 93(12): 1707 (2013)). Moreover, exogenous supplementation or overexpression of BDNF can reduce infarct volume, improve neurological outcome, enhance sensorimotor function and mediates both oligodendrogenesis and remyelination after white matter injury in experimental stroke models (Lee et al., *J. Neurosci. Res.* 88(15): 3282 (2010); Yasuhara et al., *Rejuvenation Res.* 11(1): 201 (2008); Schabitz et al., *Stroke; a journal of cerebral circulation* 38(7): 2165 (2007); Ramos-Cejudo et al., *Stroke; a journal of cerebral circulation* 46(1): 221 (2015)).

Several laboratories, including ours, have shown that neuronal expression of BDNF increases acutely after stroke as a pro-survival response and that BDNF levels correlate with the degree of functional survival (Bejot et al., *PloS one* 6(12): e29405 (2011); O'Keefe et al., *Behav. Brain Res.* 260: 162 (2014)). Decreased or low BDNF levels have been associated with depression and cognitive impairment (Zhang et al., *Biol. Trace Elem. Res.* 148(1): 38 (2012)). Given the fact that BDNF has both neuroprotective and antidepressant/neuro-restorative effects (Allen et al., *J. Affect. Disord.* 186: 306 (2015)), BDNF may be a useful treatment strategy for acute stroke and post-stroke functional deficits. Despite the known benefits of BDNF, its usefulness in treating stroke, depression, and other neurological disorders is limited due to its poor blood brain barrier (BBB) permeability and short serum half-life (Molina-Holgado et al., *CNS Neurol. Disord. Drug Targets* 7(1): 110 (2008)). Although stroke disrupts the BBB and increases vascular permeability, this does not occur until several hours after stroke onset (Fluri et al., *Drug Des. Devel. Ther.* 9: 3445 (2015); Hong et al., *Exp. Transl. Stroke Med.* 7(1): 3 (2015)). Furthermore, the BBB leakages that occur with stroke are often not of such a magnitude to allow large proteins, such as BDNF, to achieve substantial pharmacological levels within the brain (Sullivan et al., *J. Neurotrauma* 28(2): 311 (2011)).

In order to have therapeutic value, these obstacles must be overcome either by conjugating BDNF to a BBB drug delivery system or by optimizing the pharmacokinetics of BDNF to increase plasma half-life. In this study, we utilized a polymeric nano-formulation of BDNF in which BDNF molecules were incorporated into polyion complexes with block copolymers composed of safe and biocompatible diblock copolymers of (poly(ethylene glycol) (PEG) and poly(L-glutamate) (PGA) to increase CNS delivery. We have previously validated similar technology for the CNS delivery of an active antioxidant enzyme (Jiang et al., *J. Controlled Release* 213: 36 (2015)). The PEG-PGA block copolymers used in this nanoparticle formulation has been used in preclinical and clinical trials to treat cancer, among other diseases (Danson et al., *Br. J. Cancer* 90(11): 2085 (2004); Sahay et al., *J. Controlled Release* 145(3): 182 (2010); Valle et al., *Investigational New Drugs* 29(5): 1029 (2011)). This delivery system is therefore very clinically relevant and could be used in stroke patients to improve functional recovery. In this work, the effectiveness of this novel nano-formulation of BDNF was examined. Both neuroprotective and neuro-restorative potential (an improvement in behavioral outcome without a change in infarct size) were examined after experimental stroke in mice.

Methods

All animal protocols were approved by the Institutional Animal Care and Use Committee at the University of Connecticut Health Center and were performed in accordance with National Institutes of Health guidelines. C57B1/6 male mice (8-10 weeks; 20-25 g) were purchased from Jackson Laboratories (Bar Harbor, Me.). After arrival, mice were acclimatized in the animal care facility for at least 2 weeks and were maintained in an ambient temperature and humidity controlled vivarium with free access to food and water ad libitum. After gross behavioral examination all mice underwent 60 minutes of MCAo and were randomly assigned to one of three treatment conditions and one of three treatment time groups. Mice in Group A (early treatment) were treated twice with BDNF nano-particles (nano-BDNF) (250 µg/kg i.v; n=6/group) or saline at 3 and 24 hours after MCAo using lateral tail vein. Mice in Groups B (intermediate treatment) and C (delayed treatment) were treated with saline, nano-BDNF, or native-BDNF (250 µg/kg i.v., n=4-8/group) at 6 and 24 hours or 12 and 24 hours after MCAo, respectively. The amount of 250 µg/kg in the dose refers to the pure BDNF protein in the nano-formulation.

Figure 20:
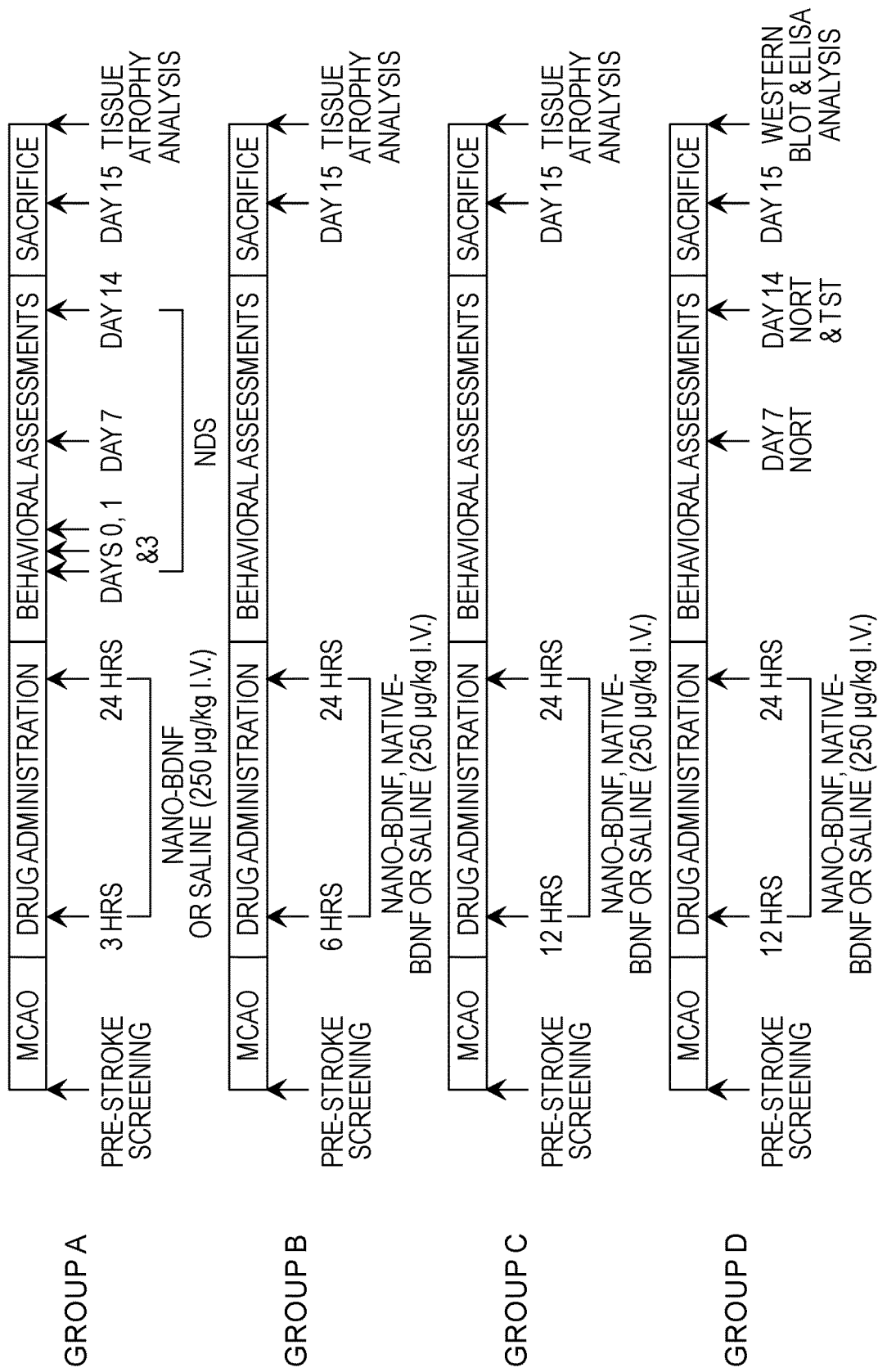
FIG. 20 shows the experimental design. Middle cerebral artery occlusion (MCAo) was performed on day 0 and either nano-BDNF, native-BDNF, or saline was injected intravenously at the respective time points. Brain tissue samples were collected from all mice on day 15 and were analyzed for tissue atrophy (in Groups A, B, and C) and for western blot analysis (in Group D). Tissue loss was calculated by subtracting the ischemic hemisphere (damaged) volume, including ipsilateral ventricle, from non-ischemic volume, including contralateral ventricle. A) Early treatment group: Neurological deficit scores were collected on days 0, 1, 3, 7 and 14. B) Intermediate treatment group. C) Delayed treatment group. D) Additional delayed treatment sub-cohort: Due to the lack of any difference in tissue atrophy outcome in our 12 hour group (Group C), we performed additional behavioral tests, and western blot and ELISA analysis in an additional 12 hour cohort (Group D).

Additionally, a sub-cohort of mice in the delayed treatment group (Group D) underwent two additional behavioral tests, a memory test (Novel Objection Recognition Test) on days 7 and 14 and a depression assessment (Tail Suspension Test) on day 14. All mice were sacrificed on day 15. Brains were used for cresyl violet staining, western blot analysis, or ELISA. Neurological deficit scores were recorded on days 0, 1, 3, 7, and 14. Serum samples were also collected at sacrifice and used for ELISA (See FIG. 20). STAIR and RIGOR guidelines were followed in this study (Lapchak et al., *Translational Stroke Res.* 4(3): 279 (2013)).

Stroke model: Focal transient cerebral ischemia was induced by a 60-minute right middle cerebral artery occlusion (MCAo) under Isoflurane anesthesia followed by reperfusion and 15 day survival as described previously (Verma et al., *Behav. Brain Res.* 269: 155 (2014)). Briefly, a midline ventral neck incision was made and unilateral right MCAo was performed by advancing a 6.0 silicone rubber-coated monofilament (Doccol Corporation, California) 10-11 mm from the internal carotid artery bifurcation via an external carotid artery stump. Rectal temperatures were monitored with a temperature control system (Fine science tools, Canada) and were maintained at ~37° C. during surgery with an automatic heating pad. Laser Doppler Flowmetry (DRT 4/Moor Instruments Ltd, Devon, UK) was used to measure cerebral blood flow, and to confirm occlusion (reduction to 15% of baseline cerebral blood flow) and reperfusion. All animals were fed with wet mash for 1 week after surgery to ensure adequate nutrition for chronic endpoints, as animals have rearing deficits after stroke. Additionally, a daily subcutaneous injection of normal saline (volume=1% v/w) was given to all animals for 1 week.

Cresyl violet staining for Tissue Atrophy: Animals in groups A, B, and C were sacrificed 15 days after stroke surgery with an overdose of Avertin (250 mg/kg i.p). After blood collection by cardiac puncture, mice underwent transcardiac perfusion using cold PBS followed by 4% paraformaldehyde. Brains were then fixed overnight and placed in cyroprotectant (30% sucrose in PBS) for 72 hours before processing. Brains were then cut into 30-µm free-floating sections using a freezing microtome and every eighth slice was mounted and stained with cresyl violet. These 30-µm sections were then used for tissue atrophy calculation. Loss of brain tissue was determined by measuring the amount of tissue atrophy in the ipsilateral hemisphere. Tissue atrophy was calculated using the following formula: % tissue atrophy=(Total ipsilateral tissue/total contralateral tissue)×100 (Verma et al., *Behav. Brain Res.* 269: 155 (2014)). Data analysis was performed by an investigator blinded to the experimental cohort.

Western blot Analysis: Animals in group D were sacrificed 15 days after stroke surgery with an overdose of Avertin (250 mg/kg i.p) and blood was collected from the right ventricle. Mice underwent cervical dislocation followed by the rapid removal of the brain. The frontal cortical region of the right (ischemic) hemisphere was separated and homogenized as described previously (Valle et al., *Investigational New Drugs* 29(5): 1029 (2011)). Protein concentration was determined using a BCA Protein Assay Kit (Thermo Fisher Scientific Inc., Rockford, Ill.) and subjected to Western Blotting as previously described (Valle et al., *Investigational New Drugs* 29(5): 1029 (2011)). A total of 20 µg of protein was loaded into each well. Protein samples were resolved on 4% to 15% SDS electrophoresis gels and transferred to a PVDF (polyvinylidene difluoride membrane). We examined the differences in expression patterns of myelin basic protein (MBP) (1:1000 Abcam), TrkB (1:1000 Santa Cruz) and actin (1:500, Sigma) in mice treated with nano-BDNF, native-BDNF, and saline. Densitometry of Western blotting images (n=5/group) was performed with computer software (Image J).

ELISA: Blood samples (Group D—see collection method above) were spun at 10,000 g for 10 minutes at 4° C.; serum supernatant was collected. Both serum (no dilution factor; n=3-6/group) and homogenized brain tissue (dilution factor: 1:2; n=3/group) were analyzed for BDNF levels using a BDNF (Mouse) ELISA Kit (Abnova).

Neurological deficit: The neurological deficit score (NDS) is a crude assessment of post-stroke behavioural recovery. ND scores, ranging from 0 to 4, were recorded on days 0, 1, 3, 7, and 14 post-MCAo (Liu et al., *J. Exp. Stroke Transl. Med.* 2(2): 2 (2009)). Our standard scoring system was as follows: 0, no deficit; 1, forelimb weakness and torso turning to the ipsilateral side when held by tail; 2, circling to affected side; 3, unable to bear weight on affected side; and 4, no spontaneous locomotor activity or barrel rolling (Venna et al., *Transl. Psychiatry* 4: e351 (2014)).

Novel Object Recognition Task (NORT): The NORT is used to evaluate cognition, particularly recognition memory, in rodent models of CNS disorders (Antunes et al., *Cognitive Processing* 13(2): 93 (2012)). This test is based on the tendency of mice to spend more time exploring a novel object than a familiar one. This preference is used to assess intact recognition memory. Mice were placed in the behavioral room for an hour prior to testing to allow acclimatization. During habituation animals were allowed to explore an empty arena for at least 10 minutes. Twenty-four hours after habituation, animals were exposed to the familiar arena with 2 identical objects placed at an equal distance for 10 minutes (trial phase). If the total time of exploration of these objects was greater than 20 seconds, these mice qualified for the experimental test (Leger et al., *Expert Rev. Clin. Pharmacol.* 6(4): 423 (2013)) which was conducted 2 hours after the trial. One of the objects from the trial was replaced with a novel object. Mice were then allowed to explore the test arena for 10 minutes. The experiment was recorded using a digital video camera (JVC Everio, Victor Company, Japan) by a trained observer. A discrimination index (DI) was calculated by using the formula $DI=(T_N-T_F)/(T_N+T_F)$, where $T_N$=time spent exploring the novel object and $T_F$=time spent in exploring of familiar objects. The NORT was performed on days 7 and 14 after stroke and analyzed by an experimenter blinded to treatment. Different novel objects were used each week; the arena was cleaned between tests to remove olfactory cues.

Tail Suspension test (TST): The tail suspension test (TST) was performed as described previously (Chatterjee et al., *ISRN Psychiatry* 2012: 595141 (2012)) with minor modifications. Mice were placed in the behavioral room for an hour prior to testing to allow acclimatization. Briefly, the mice were individually suspended from the tail suspension apparatus, 60 cm above the surface of the table. The experiment was recorded for six minutes using a digital video camera (JVC Everio, Victor Company, Japan). A trained observer who was blinded to the treatment conditions then recorded the duration of immobility. The mouse was considered immobile in the absence of initiated movement. In general, an immobile mouse will appear to hang passively unless it has retained momentum from a movement immediately prior to the current bout of immobility. The testing apparatus was cleaned between trials to remove olfactory cues. Due to the potential stress induced by the TST, this was only performed once, on day 14, the day prior to sacrifice.

Statistics: All data were analyzed and expressed as means ±S. E. M. The non-parametric NDS in the 3-hour cohort was analyzed via Mann-Whitney U test. Tissue atrophy in the 3-hour cohort was analyzed by a T test. Tissue atrophy for the 6 and 12-hour cohort, as well as NORT, TST, western blot, and ELISA data, were analyzed by a one-way ANOVA with a Newman-Keuls post hoc test to correct for multiple comparisons. A probability value of p<0.05 was considered to be statistically significant.

Figure 21:
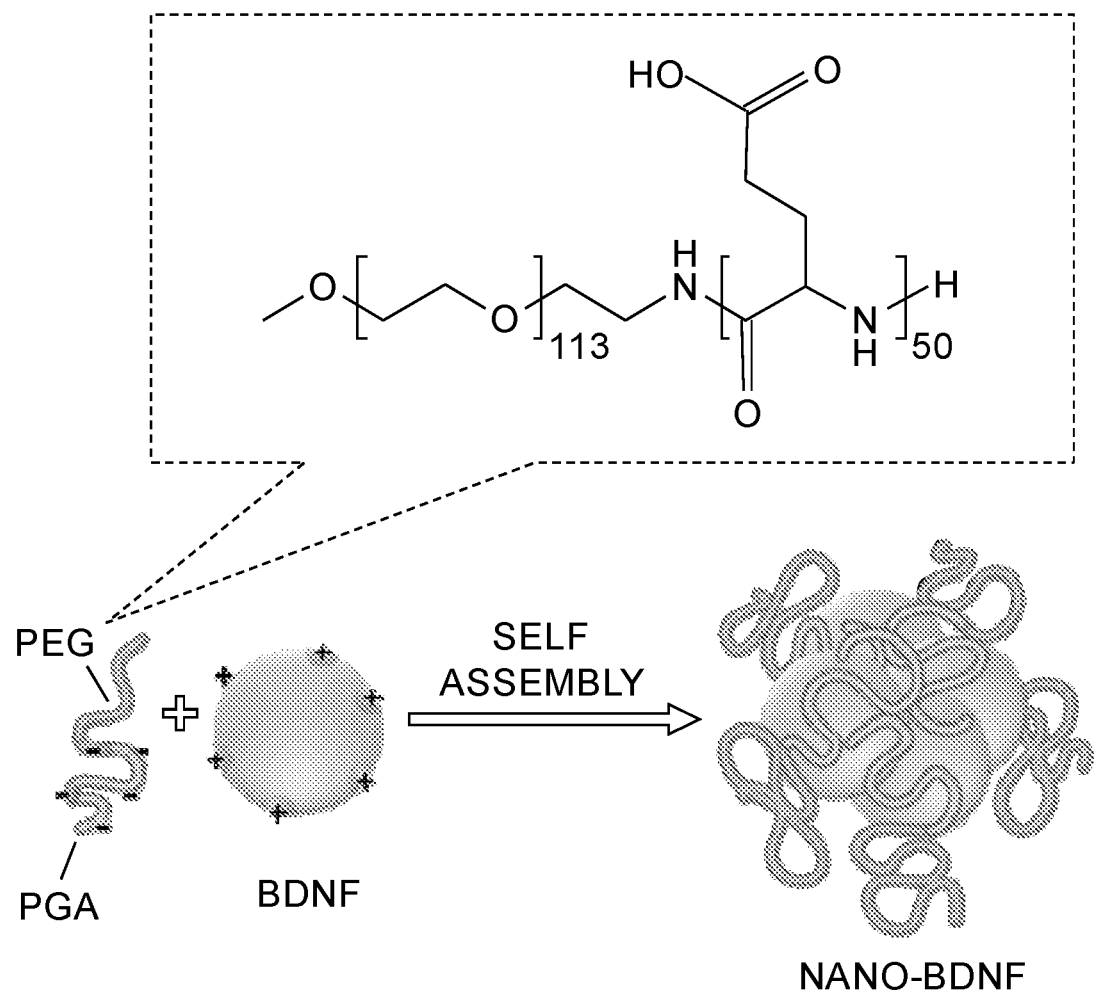
FIG. 21 is a schematic illustration showing the spontaneous formation of BDNF nano particle in water upon simple mixing of the native BDNF and PEG-PGA block copolymer. BDNF electrostatically couples with the oppositely charged PGA chain and entraps into a particle core surrounded by a shell of uncharged water-soluble PEG.

Nano-BDNF: We prepared the nano-BDNF formulation by polyion complexation of human recombinant BDNF (Peprotech, Rocky Hill, N.J.) with PEG(5 kDa)-PGA(9 kDa) diblock copolymer (Alamanda Polymers, Huntsville, Ala.) in aqueous solution in phosphate buffered saline, pH 7.4 (FIG. 21). Dynamic light scattering (DLS) revealed that the complex particle size is 95 nm with a relatively small polydispersity index (PDI) of 0.165 (measured at 0.1 mg/mL BDNF in de-ionized water). This reaction between charged proteins with doubly hydrophilic block copolymers with ionic and nonionic blocks has been well characterized (Harada et al., *Macromolecules* 31(2): 288 (1998); Harada et al., *Langmuir* 15(12): 4208 (1999)) and applied as protein delivery tools (Jiang et al., *J. Controlled Release* 213: 36 (2015); Jiang et al., *J. Controlled Release* 231: 38 (2016); Manickam et al., *J. Controlled Release* 162(3): 636 (2012)). The formulation was stored in the solution form at 4° C. before injection. The particle size did not change over the observation period of several weeks.

Radioactive Labeling of BDNF: BDNF and bovine serum albumin (BSA) were labeled with iodine by chloramine-T method (Yi et al., *J. Controlled Release* 191: 34 (2014)). Briefly, BDNF was mixed with 1 mCi of Na$^{125}$I or Na$^{131}$I (Perkin Elmer) and 10 µg of chloramine-T in phosphate buffer (0.25 M, pH 7.5) for 60 s. Labeled protein was purified by Illustra Nap-5 columns (Life technologies) and collected in tubes pretreated with 1% BSA in PBS to prevent nonspecific adsorption. The iodine association (iodine in labeled sample/total iodine) was determined by trichloroacetic acid precipitation method (Yi et al., *J. Controlled Release* 191: 34 (2014)). Briefly, 1 µl of purified samples was mixed with 0.5 ml of 1% BSA in PBS and 0.5 ml of 30% trichloroacetic acid, and then centrifuged at 5400 g for 10 min. The resulted pellet and supernatant were counted on r-counter (PerkinElmer). The iodine association was calculated as the percentage of pellet radioactivity to total radioactivity. The iodine association for BSA/BDNF was higher than 85% and 98%, respectively. The $^{125}$I-labeled BDNF was used for preparation of polyion complexes with PEG-PGA ($^{125}$I-labeled nano-BDNF). In this case the tubes for preparation of the complexes were pre-coated with PEG-PGA avoid the tracer adsorption on the walls.

Pharmacokinetics studies. The studies of pharmacokinetics of BDNF and nano-BDNF were carried out in CD-1 male mice (8 to 10 weeks of age) (Charles River Laboratories, Wilmington, Mass.) as described previously (Yi et al., *J. Controlled Release* 191: 34 (2014)). Briefly, mice were be anesthetized with urethane and then given an injection into the tail vein of $^{125}$I-BDNF or $^{125}$I-nano-BDNF ($3\times10^5$ cpm/mouse) in 0.2 ml of saline; the injection also contained $^{131}$I-labeled BSA ($3\times10^5$ cpm/mouse) that served to measure the brain's vascular space. The blood and whole brain were collected at different time points and measured in a gamma counter (3 mice per time point). As $^{131}$I and $^{125}$I are distinguishable in our gamma counter, we can measure cytokine and albumin uptake in the same animal. The volume of distribution (Vd), the serum half-life ($t_{1/2}$), the brain/serum ratio (µL/g), the % of the injected dose in a ml of serum (% Inj/ml) and taken up per g of brain (% Inj/g), the Area Under the Curve (AUC) in serum and brain, and the unidirectional influx rate (Ki, [µl/g-min]) were determined by multiple-time regression analysis (Blasberg et al., *J. Cerebral Blood Flow Metab.* 3(1): 8 (1983); Patlak et al., *J. Cerebral Blood Flow Metab.* 3(1): 1 (12983)).

Results

Figure 22A:
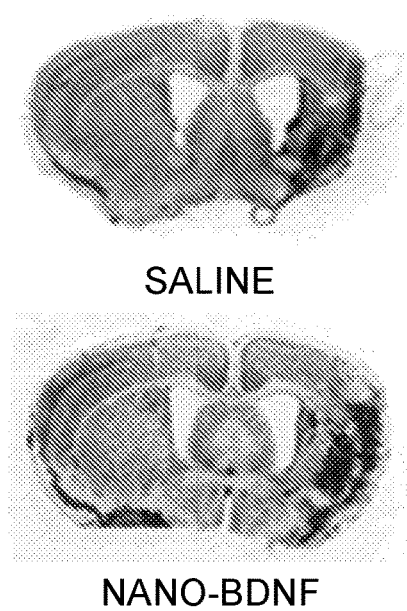
FIGS. 22A-22D show A) Representative images of cresyl violet stained coronal brain sections. B) Group A: Quantification of tissue atrophy. Mice treated with nano-BDNF formulation (3 and 24 hours post MCAO) had significantly reduced tissue loss compared to saline treated mice on day 7 of survival (p=0.0062; n=5/group). (C) Line graph showing the recovery trajectory of nano-BDNF and saline treated mice; on day 3 mice treated with nano-BDNF formulation (3 and 24 hours post MCAO) had significantly improved neurological deficit scores compared to saline on day 3 after MCAO. (D) Day 3 NDS. Bar graph.
Figure 22C:
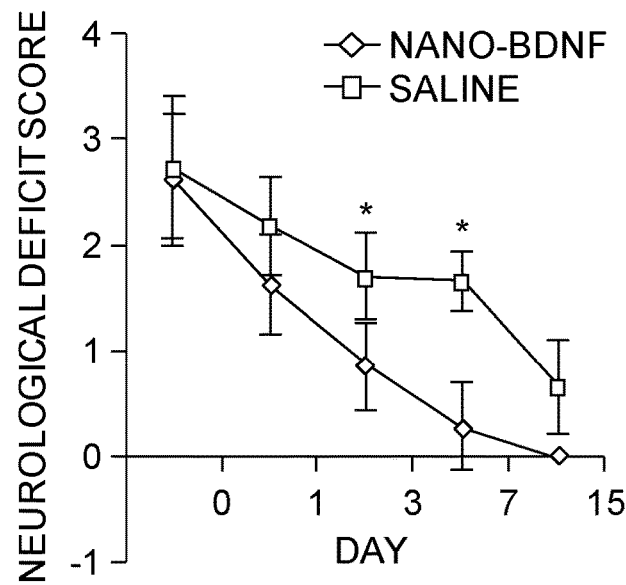
Figure 22B:
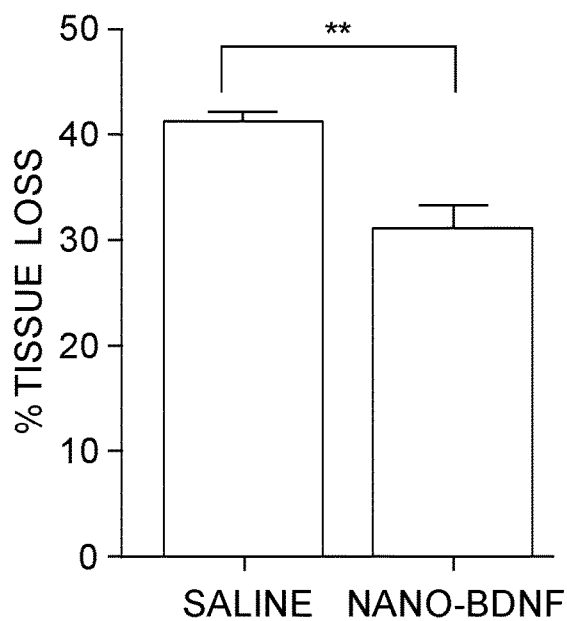
Figure 22D:
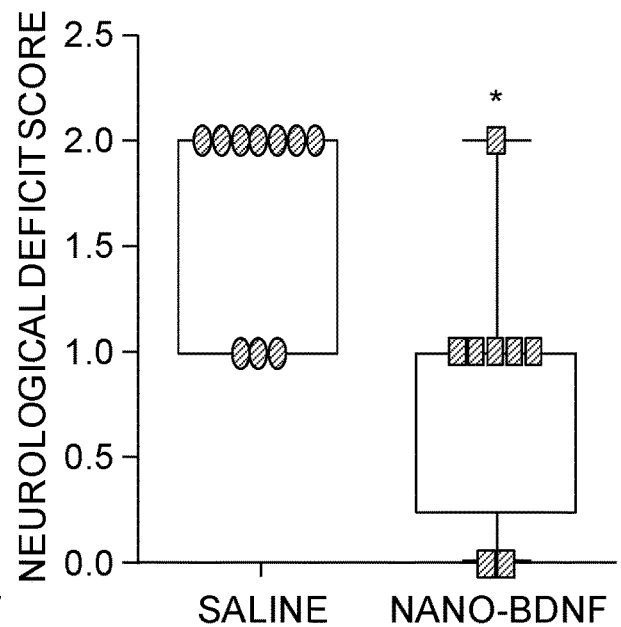

BDNF Nano-Particles Reduce Tissue Atrophy and Improve Neurological Deficit Scores:

In our first experiment, we examined the neuroprotective potential of nano-BDNF. Mice were treated with nano-BDNF or saline at 3 and 24 hours after MCAo (Group A). We found a significant reduction in the amount of tissue lost (31.02±4.89% vs. 41.33±2.26%; p=0.0062) after nano-BDNF treatment (FIG. 22B). Moreover, nano-BDNF treated mice also showed earlier recovery of their neurological deficits on day 3 (FIGS. 22C and 22D).

Figure 23A:
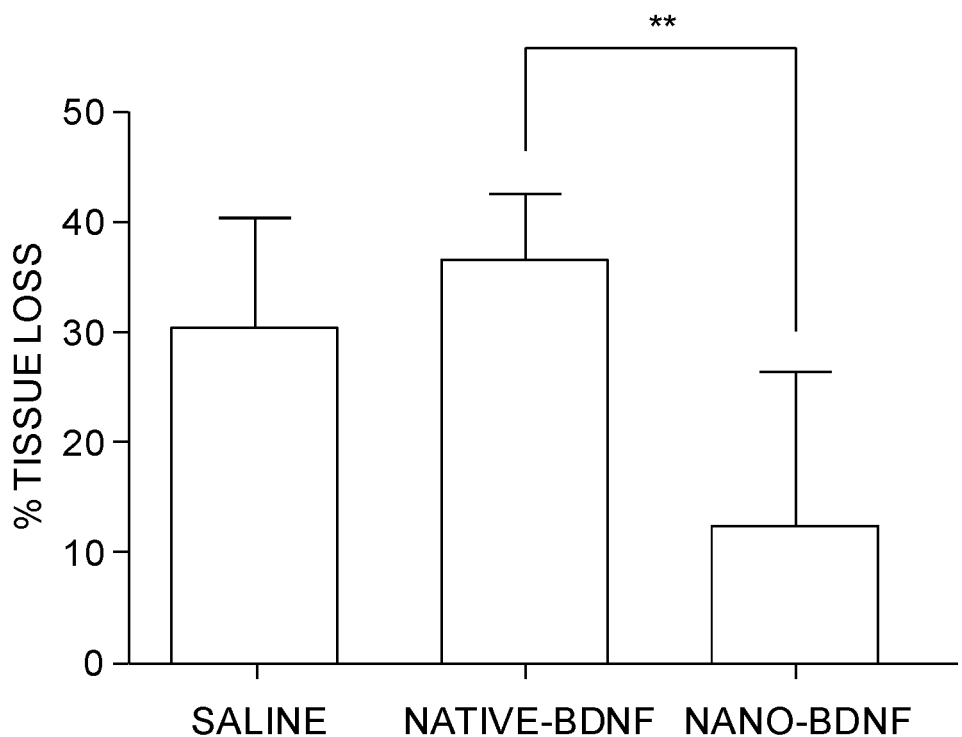
FIGS. 23A-23B show Groups B and C: Quantification of tissue atrophy. A) Mice treated with nano-BDNF 6 and 24 hours post MCAo had significantly reduced tissue loss compared to saline treated mice after 15 days of survival ([F (2, 12)=8.256, p=0.00432; n=5/group). B) Delayed treatment with nano-BDNF (12 and 24 hours post MCAO) did not significantly reduce tissue loss compared to native-BDNF or saline treatment.
Figure 23B:
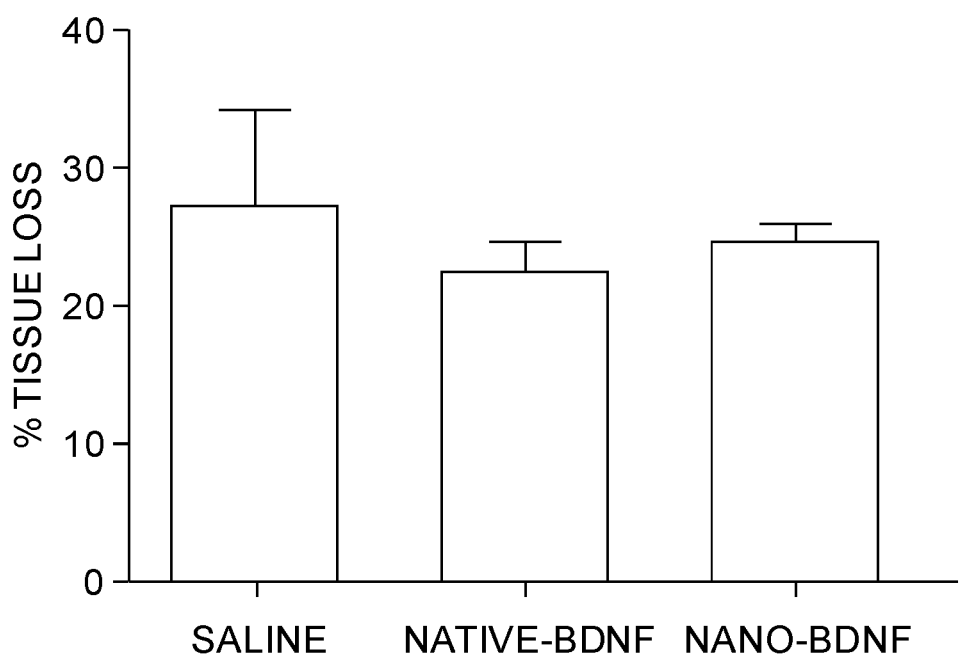

Next, the therapeutic window of nano-BDNF was assessed. We also performed a direct comparison between nano-BDNF and native-BDNF formulations. The first treatment dose (nano-BDNF, native-BDNF, or saline) was delayed until 6 hours after ischemic onset (Group B). Nano-BDNF significantly reduced tissue loss after MCAo compared to native-BDNF treatment (11.89±12.82% vs. 36.40±5.97%) [F (2, 12)=8.256, p=0.00432]; no difference in tissue loss was seen between saline and native-BDNF treatment (FIG. 23A). Similar to 3 hour treatment, 6 hour treatment with nano-BDNF showed a positive trend in NDS. However, results were not significant (P=0.13, 0.17 and 0.2302 at Day 3, 7 and 14 respectively between saline and nano BDNF cohort B). In a third cohort (Group C and D), the first dose of nano-BDNF was further delayed until 12 hours after ischemic onset. In third cohort, however, no significant differences in tissue atrophy (FIG. 4B) or NDS was found (Day 7: 1.43±0.23 vs 1.16±0.3 vs 0.85±0.41 and day 14: 1.21±0.25 vs 1±0.32 vs 0.8±0.43 respectively in saline vs native vs nano-BDNF).

Figure 24:
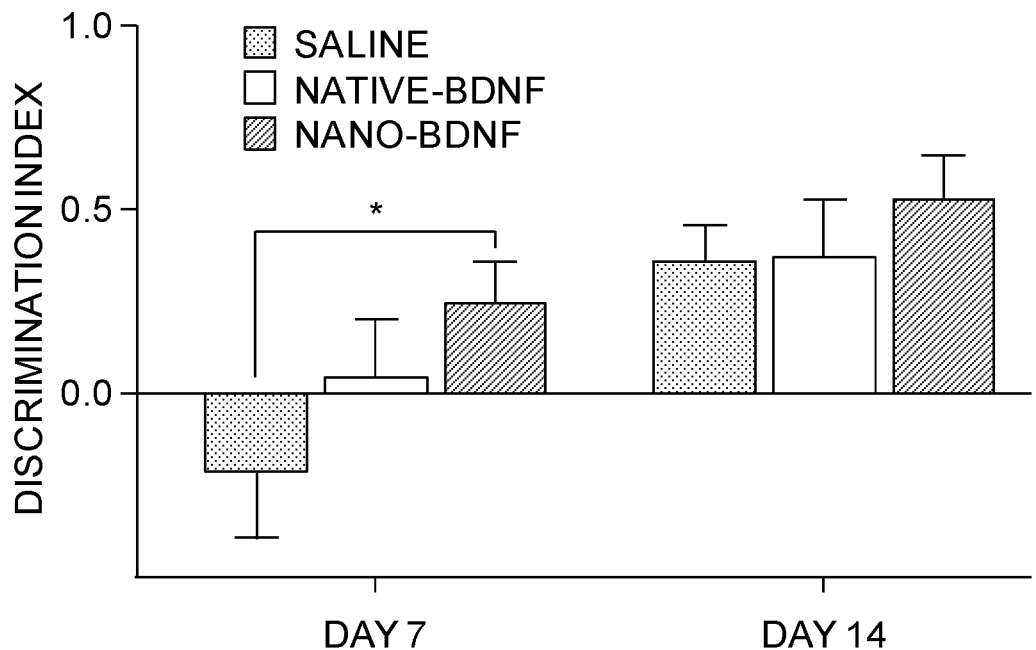
FIG. 24 shows Group C: Novel Object Recognition Test. Despite the lack of significant histological changes in infarct volume, nano-BDNF treated mice (12 and 24 hours post MCAO) had improved learning and memory on day 7, as shown by a significantly higher discrimination Index (DI), when compared to saline and native-BDNF treated mice ([F (2, 12)=4.224, p=0.0468] (n=5 group). BDNF treated mice also had a higher DI at day 14, but this was not significant.
Figure 25:
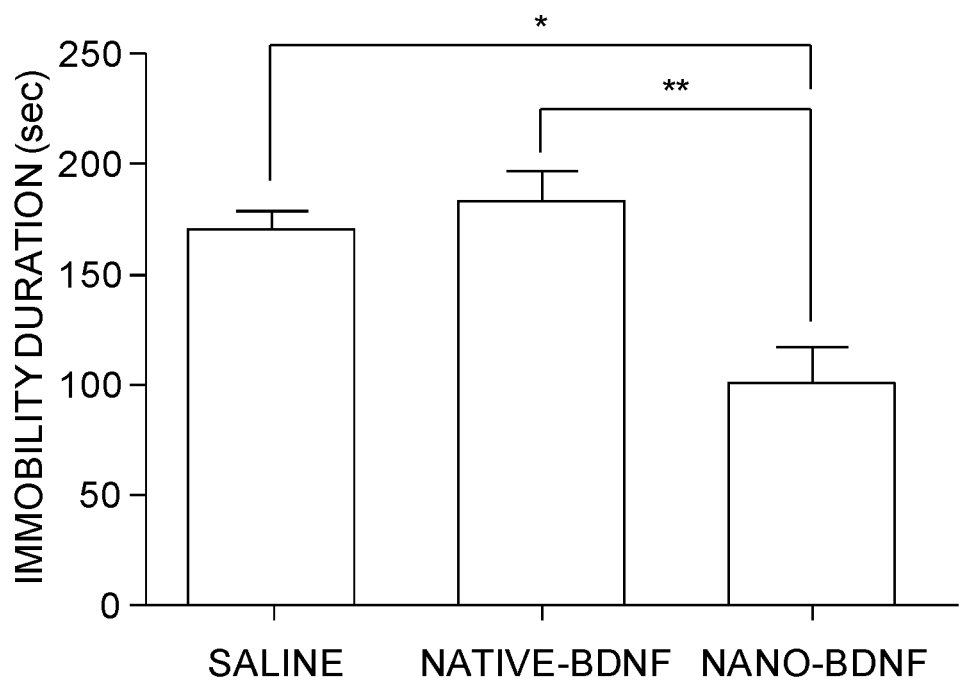
FIG. 25 shows Group C: Tail Suspension Test. Despite the absence of changes in infarct volume, nano-BDNF treated mice (12 and 24 hours post MCAO) had significantly reduced immobility compared to saline (p<0.05) and native (p<0.01) treated mice [F (2, 12)=9.953, p=0.0034] (n=5/group), signifying a reduced depressive phenotype.

Delayed Treatment with Nano-BDNF Formulation Improves Memory and Depressive Behavior:

BDNF treatment has been found to improve memory after stroke and have general anti-depressant effects (Zhang et al., *Biol. Trace Elem. Res.* 148(1): 38 (2012); Schmidt et al., *Neuropsychopharmacology* 36(12): 2375 (2011); Sirianni et al., Brain Res. 1321: 40 (2010)). Given that we found no neuroprotective effects of nano-BDNF 12 hours after ischemia, we decided to evaluate an additional cohort of animals (Group D) for chronic behavioral changes after delayed BDNF treatment (treated at 12 and 24 hours post MCAo). This paradigm allows us to separate neuroprotective from neuro-restoration as infarct damage was equivalent in the treatment groups. Nano-BDNF treatment led to improved learning and memory at day 7 after MCAo compared to saline treated mice ($p<0.05$), as shown by a significantly higher discrimination Index (DI) [F (2, 12)=4.224, $p=0.0468$], while native-BDNF treatment led to intermediate effects (FIG. 24). It should be noted that nano-BDNF treated mice also had a higher DI at day 14, but this was not statistically significant, perhaps due to the repeated testing. In addition to an improvement in memory, delayed nano-BDNF treatment led to a reduction in depressive-like behavior as shown by significantly reduced immobility in the tail suspension test when compared to saline ($p<0.05$) and native-BDNF treated mice ($p<0.01$) [F (2, 12)=9.953, $p=0.0034$] (FIG. 25). These behavioral improvements were seen despite the lack of gross histological change.

Figure 26A:
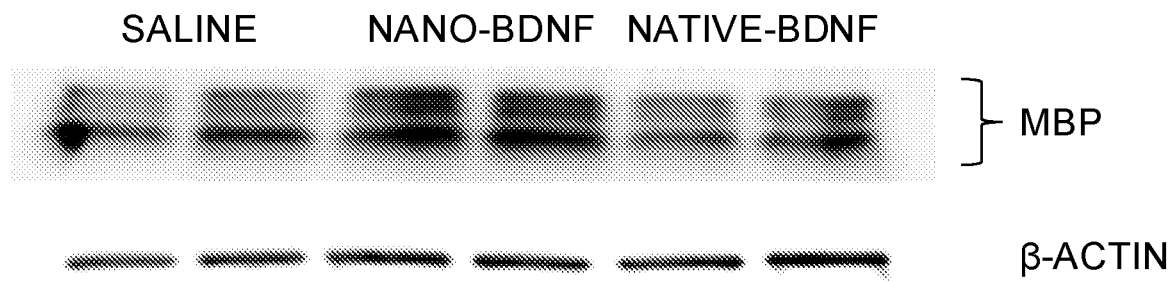
FIGS. 26A-26B show Group C: Western Blot analysis. A) Representative image. B) Nano treatment (12 and 24 hours post MCAO) led to a more significant increase in MBP levels (p<0.01) compared to saline than did native-BDNF treated mice [F (2, 12)=41.52, p=0.0065] (n=5/group). Two MBP specific bands were present between 17-22 kDa.
Figure 26B:
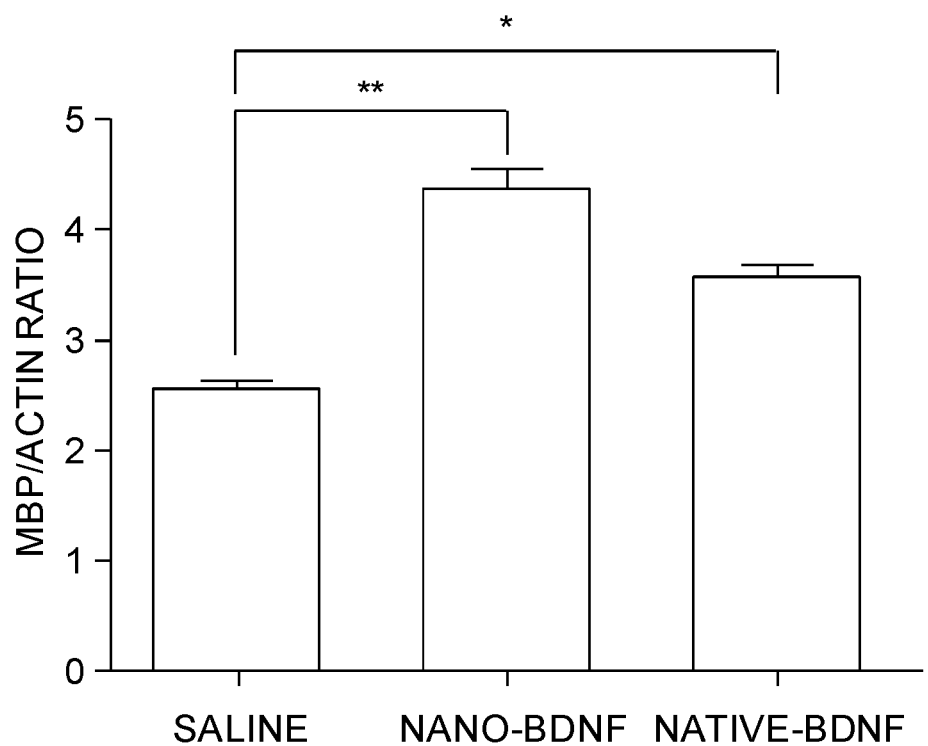
Figure 27A:
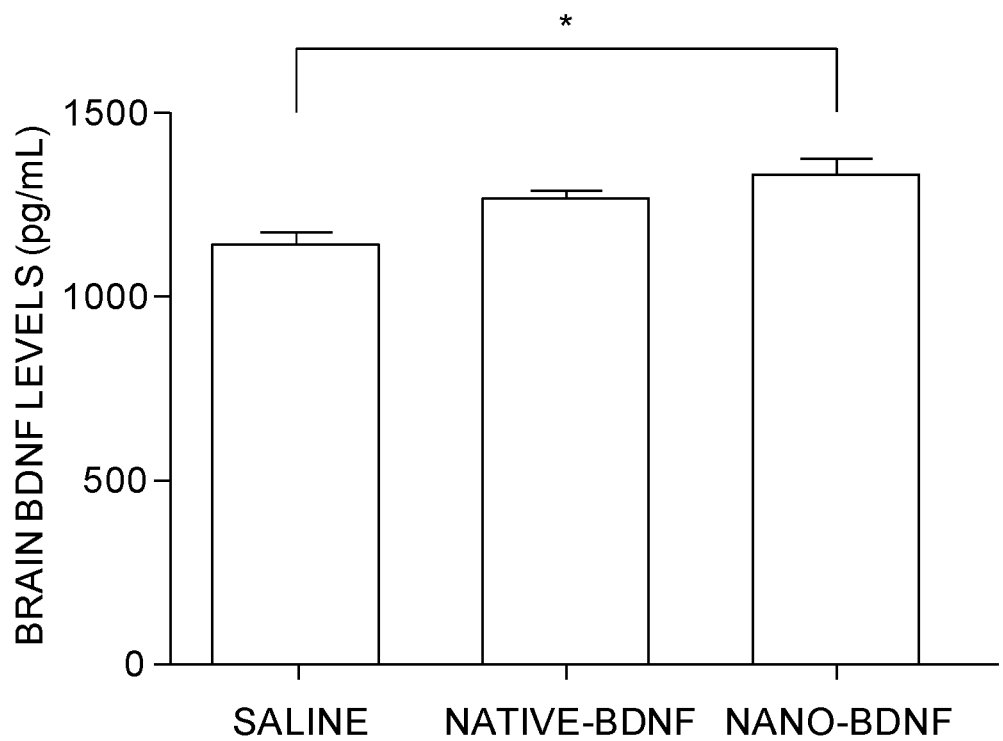
FIGS. 27A-27B show brain and serum BDNF ELISA. A) Despite the lack of significant histological changes in infarct volume, nano-BDNF treated mice (12 and 24 hours post MCAO) had significantly higher brain BDNF levels than saline treated mice 15 days following MCAO ([F (2, 9)=8.165, p=0.0148] (n=4/group); however, there were no significant differences between nano and native-BDNF treated mice or between saline and native-BDNF treated mice. B) There were no significant differences between groups in serum BDNF levels (n=3-6/group).
Figure 27B:
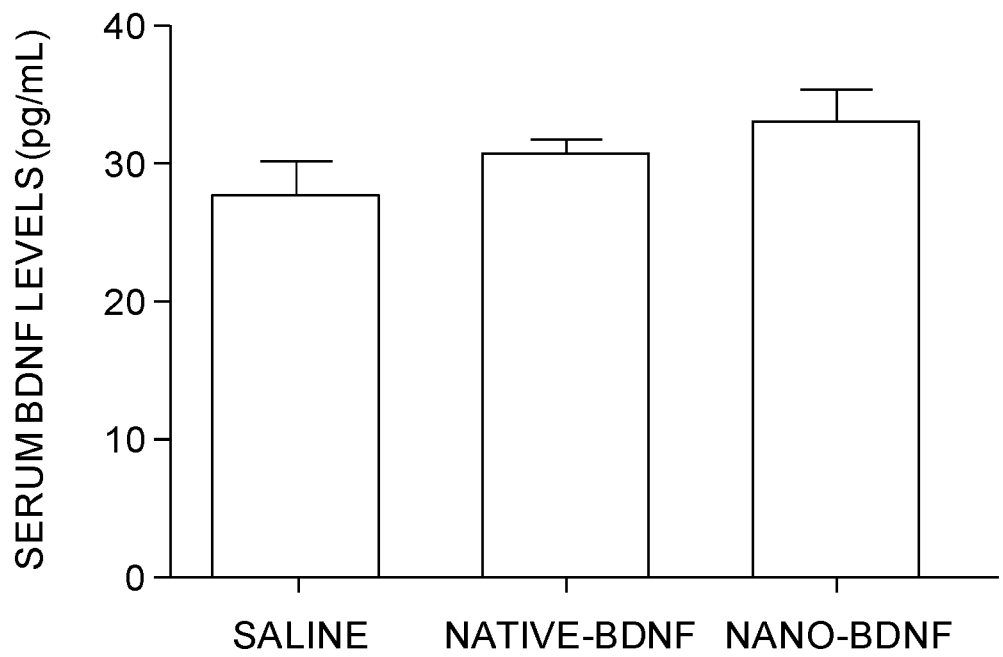

Nano BDNF Treatment Increases MBP Expression and Brain BDNF Levels:

The effect of nano-BDNF treatment on MBP and Trk-B expression in the frontal cortical region of right (ipsilateral) hemisphere was assessed in mice from the delayed treatment cohort (Group D). We found no significant difference in TrkB expression between groups. We did, however, find that nano-BDNF treatment led to significantly increased expression of MBP compared to saline treatment (4.36±0.20 vs. 2.56±0.08; $p<0.01$); native-BDNF treatment led to a less significant increase in MBP levels when compared to saline treated animals (3.58±0.11 vs. 2.56±0.08); [F (2, 12)=41.52, $p=0.0065$] (FIG. 26B). Mice treated with nano-BDNF had significantly higher brain BDNF levels than saline treated mice (1339.79±40.39 vs. 1145.08±35.52) [F (2, 9)=8.165, $p=0.0148$] (FIG. 27A), however, BDNF levels were not significantly different between native-BDNF and saline treated mice. We found no differences in serum BDNF levels between groups (FIG. 27B).

To assess whether our nanoformulation increases the entry of the BDNF protein to the brain we characterized the pharmacokinetics of the free BDNF and nano-BDNF after IV administration. In this study, BDNF was labeled by $1^{125}$ and then formulated with PEG-PGA. These BDNF forms were administered IV into CD-1 mice and the radioactivity levels in the blood and brain were measured at different time points (FIGS. 19A-19C). The nano-BDNF shows similar serum clearance as BDNF ($t_{1/2}$ 15.6 min vs. 15.1 min). Importantly, the brain pharmacokinetics profile of nano-BDNF was drastically improved as demonstrated by: 1) increased influx rate across the blood brain barrier, measured by Ki at 0.84 µL/g·min (the slope); whereas BDNF was rapidly effluxed from brain to blood; 2) increased uptake compared to that of BDNF by over 6 times, calculated by AUC (2.96 (% inj/g)×(min) for nano-BDNF vs 0.54 for BDNF) over 10 min following IV injection; and 3) crossing the BBB and accumulation in brain parenchyma.

Discussion:

This study examined the neuroprotective and neuro-restorative efficacy of a novel nano-BDNF formulation. Despite the fact that BDNF administration after stroke can reduce infarct size, limit post-stroke depressive behavior, enhances post-stroke sensorimotor recovery, cognition and neurogenesis in animal models, its limited brain bioavailability and short serum half-life have limited its usefulness in a clinical setting. In this study, we examined the efficacy of "nano-BDNF" in which BDNF molecules are incorporated into polyion complexes with block copolymers composed of safe and biocompatible polymers, poly (ethylene glycol) (PEG) and poly(L-glutamate) (PGA). We have previously validated the polyion complex technology in the delivery of an active antioxidant enzyme to the brain in an animal model of cerebral ischemia (Jiang et al., *J Controlled Release* 213: 36 (2015)). In this study, we evaluated nano-BDNF as a potential therapeutic agent for the treatment of brain injury in an animal model of stroke.

Although previous studies have shown the efficacy of BDNF in improving post-stroke recovery in animal models (Clarkson et al., *J. Cerebral Blood Flow Metab.* 35(8): 1272 (2015); Yu et al., *PloS One* 8(12): e81750 (2013)), BDNF was given quite quickly after stroke onset, a therapeutic time-window that is often not practical in clinical situations. In this study, extended therapeutic windows were evaluated, with treatment delayed for over 12 hours after stroke onset. We first showed the efficacy of early nano-BDNF treatment in reducing tissue loss. We next examined the efficacy of nano-BDNF at a later first dose time point, 6 hours. At this time point we also added a native-BDNF-treatment as an additional control to rule out any contribution of the peripheral effects of BDNF treatment and to allow us to directly compare native BDNF with the novel nano-BDNF formulation. We found that nano-BDNF treatment led to significantly reduced tissue damage when compared to native-BDNF, confirming the improved efficacy of the novel nanoparticle formulation.

We also examined the efficacy of nano-BDNF treatment at an even more delayed first dose time point, 12 hours after stroke onset. Delayed nano-BDNF treatment even as late as 12 hours following stroke increased MBP expression and BDNF levels in the brain 15 days after drug administration. As the increased brain accumulation of BDNF after IV administration of nano-BDNF appears to be short-lived (minutes), we assume that any differences in brain BDNF levels at 15 days were due to differences in endogenous activation of BDNF, and not due to residual BDNF from the initial tail vein injection.

Moreover, 12 hour nano-BDNF also reduced post-stroke depressive phenotypes, and improved cognitive deficits. Many previous studies have found post-stroke behavioral improvement even in the absence of histological changes especially at chronic endpoints (Johansson, *Acta Neurochirurgica Supplement* 66: 63 (1996); Johansson et al., *Exp. Neurol.* 139(2): 322 (1996); Yamamoto et al., *Stroke; a journal of cerebral circulation* 20(8): 1089 (1989)), which was seen in this study. Gain or loss of BDNF has been shown to lead to an increase or decrease in MBP expression, respectively (Djalali et al., *J Neurochem.* 92(3): 616 (2005)). The upregulation of MBP and brain BDNF levels after nano-BDNF treatment supports the hypothesis that the behavioral recovery that we observed was due to nano-BDNF and this formulation is superior to that of native-BDNF. Taken together, these results suggest that delayed treatment of nano-BDNF beyond 6 hours is not neuroprotective, as infarct size was equivalent, however nano-BDNF continues to have important neuro-restorative effects that are seen weeks after drug administration. Targeting the recovery phase of stroke may lead to enhancement of functional outcomes that are independent of infarct size.

The benefits of BDNF treatment have been linked to enhancements in neurogenesis, brain repair, neuronal activity, cell survival as well as remyelination after white matter injury in subcortical stroke models (Hermann et al., *Lancet Neurol.* 11(4): 369 (2012); Murphy et al., *Nat. Rev. Neurosci.* 10(12): 861 (2009)). However, the exact mechanism by which BDNF is restorative is not well understood. Our observation that nano-BDNF treatment increases the expression of MBP even after delayed treatment is consistent with previous findings (Ramos-Cejudo et al., *Stroke; a journal of cerebral circulation* 46(1): 221 (2015)). As enhancing MBP can have positive effects on both cognitive and motor skills (Lu et al., *Brain Cognition* 81(1): 131 (2013); McKenzie et al., *Science.* 346(6207): 318 (2014)), the increase in MBP expression may be partially responsible for the behavioral improvements seen in the cohorts of mice treated with nano-BDNF.

Example 7

Intranasal Delivery of Superoxide Dismutase

Figure 28:
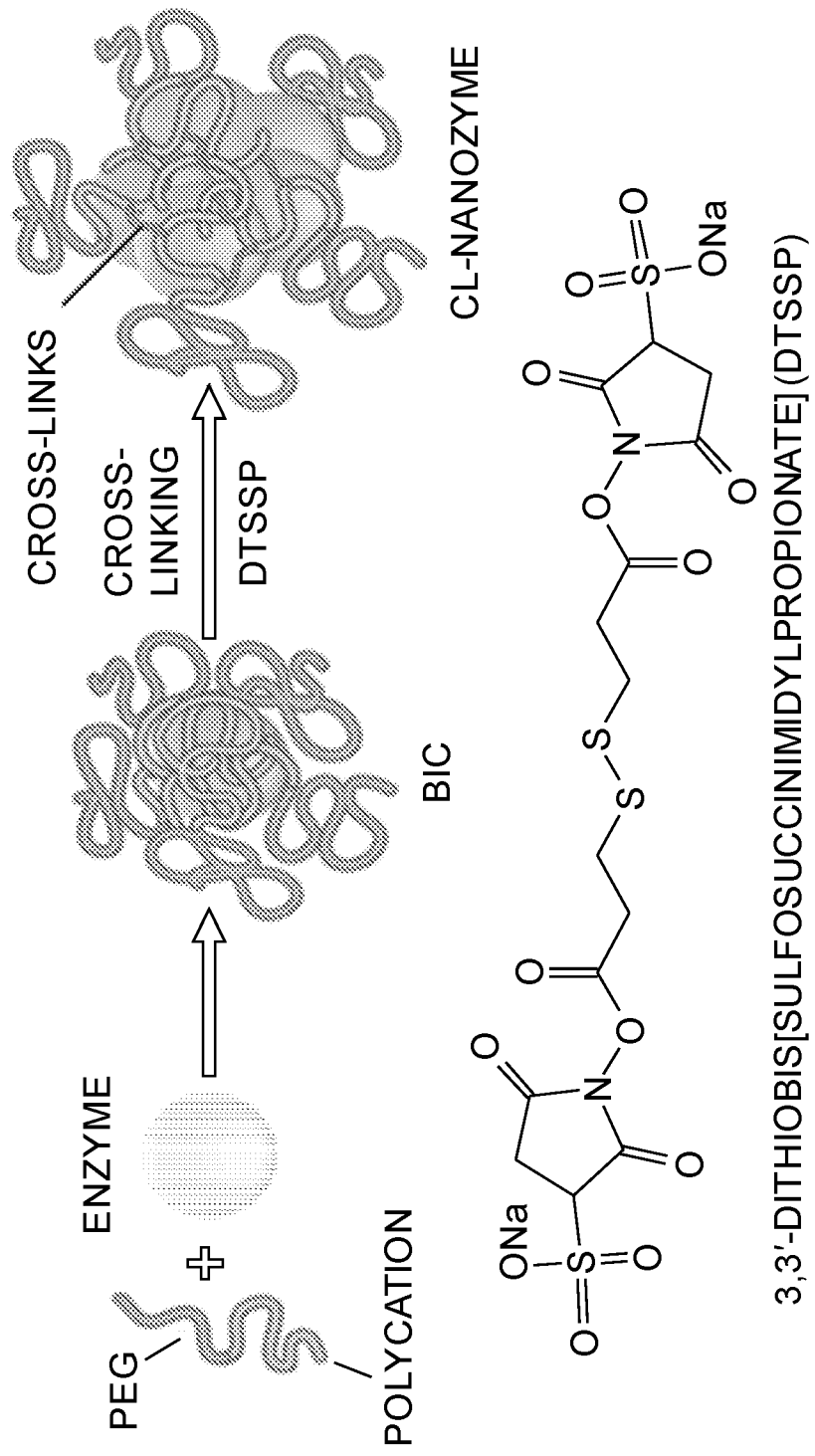
FIG. 28 shows a schematic representation of crosslinked nano-SOD1 synthesis. Block ionomer complexes form due to spontaneous self-assembly resulting from electrostatic binding of negatively-charged SOD1 with cationic block copolymer PEG-PLL to which DTSSP is added to covalently stabilize the BIC by cross-linking primary amine groups.

Crosslinked nano-SOD1 was synthesized with native SOD1 and poly(ethylene glycol)-b-poly(L-lysine) (PEG-PLL) at the polycation to SOD1 charge ratio $Z_{+/-}2$ using DTSSP as a cross-linker (FIG. 28). After synthesis and desalting (to remove unreacted DTSSP), crosslinked nano-SOD1 was purified to separate the cross-linked from the non-cross linked species. For the purification, crosslinked nano-SOD1 in 10 mM HEPES buffer containing 0.3 M NaCl (pH=7.4) was loaded onto Macrosep centrifugal device (Pall Corporation, MI) and concentrated twice to about 10% of its initial volume by centrifugation at 4,500 rpm at 4° C. The concentrate was collected and desalted using NAP™ columns to remove excess NaCl. The eluent was then collected in 10 mM HEPES buffer containing 0.15 M NaCl (pH=7.4). SOD1 enzyme activity was determined using a microplate version of pyrogallol assay, and normalized to protein content determined by Inductively Coupled Plasma Mass Spectrometry (ICP-MS) using copper and zinc as standards. Particle effective diameter (z-average hydrodynamic diameter) and polydispersity index (PDI) were measured using a Malvern Zetasizer Nano (Malvern Instruments Ltd., MA). The purified crosslinked nano-SOD1 had a particle diameter of 39.2±0.8 nm (PDI<0.1), and retained 58.6±9.5% enzyme activity relative to native SOD1.

Figure 29:
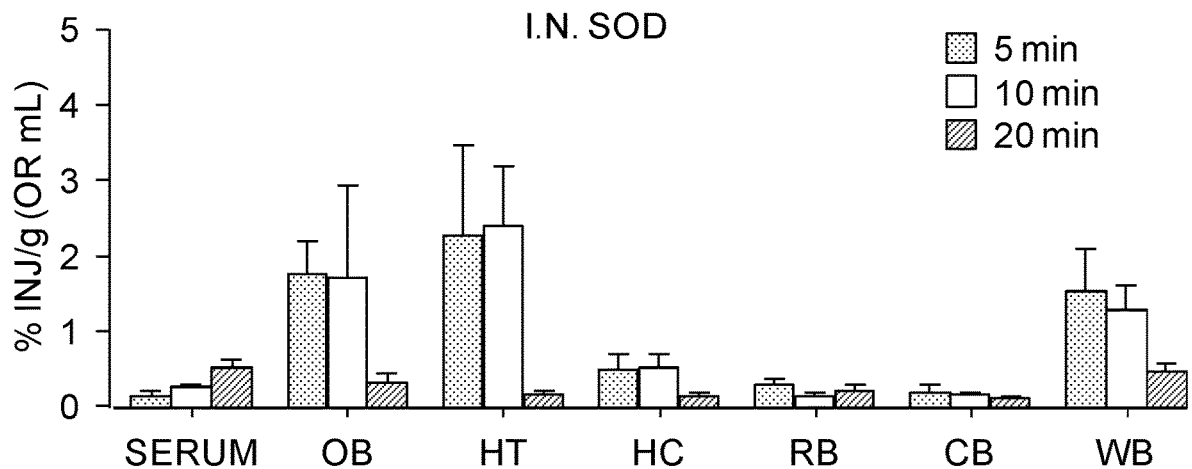
FIG. 29 shows brain region distribution of radiolabeled SOD1, crosslinked nano-SOD 1 and non-cross linked nano-SOD1 following nasal administration.
Figure 29:
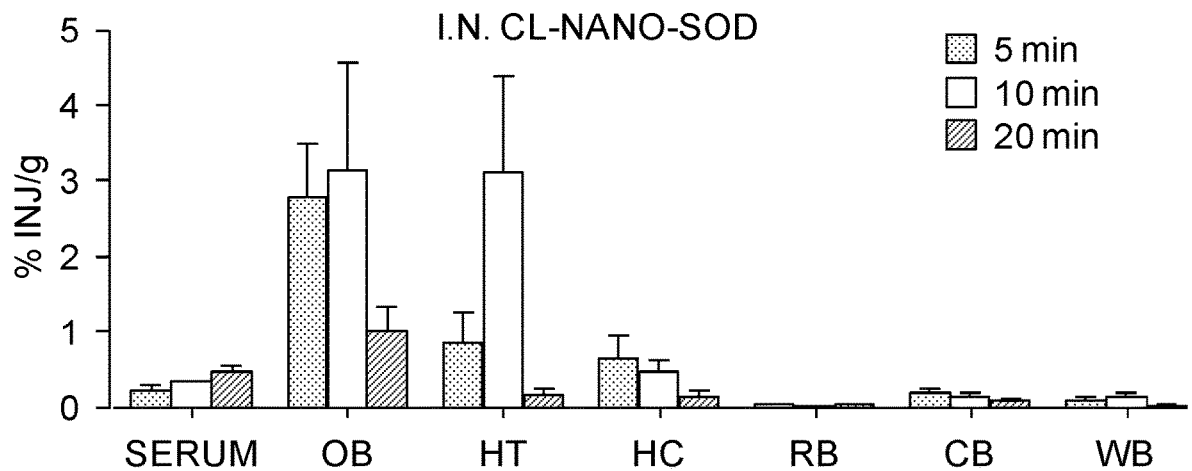
Figure 29:
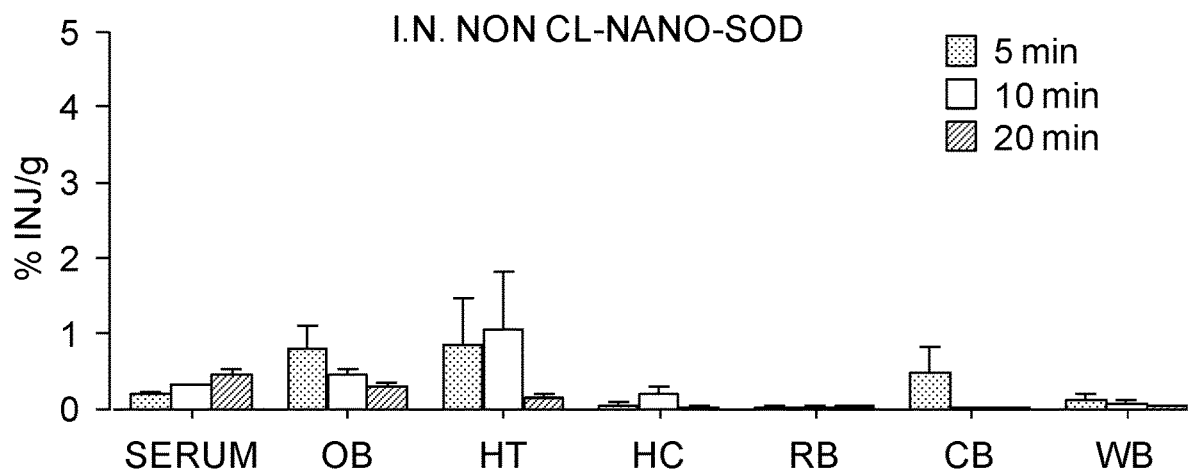

Following intranasal administration, native SOD1, crosslinked nano-SOD1 and non-crosslinked nano-SOD1 showed most abundant distribution in the olfactory bulb (OB) and hypothalamus (HT) relative to other brain regions at all time points examined. The crosslinked nano-SOD1 was prepared before $^{125}$I labeling. A trace amount ($10^6$ cpm/mouse) of $^{125}$I-labelled native SOD1, crosslinked nano-SOD1 or non-crosslinked nano-SOD1 was administered INB into CD-1 mice. Radioactivity levels in the serum, brain, and brain regions were measured up to 20 min after the administration. In FIG. 29 it is demonstrated that all three species of $^{125}$I-SOD1 was distributed to the serum to similar degrees. In the brain, most uptake appeared in the olfactory bulb and hypothalamus compared to other brain compartments. Interestingly, the $^{125}$I-non-crosslinked nano-SOD1 showed less uptake than $^{125}$I-native-SOD1 and $^{125}$I-crosslinked nano-SOD1 in all the brain regions examined.

Figure 30:
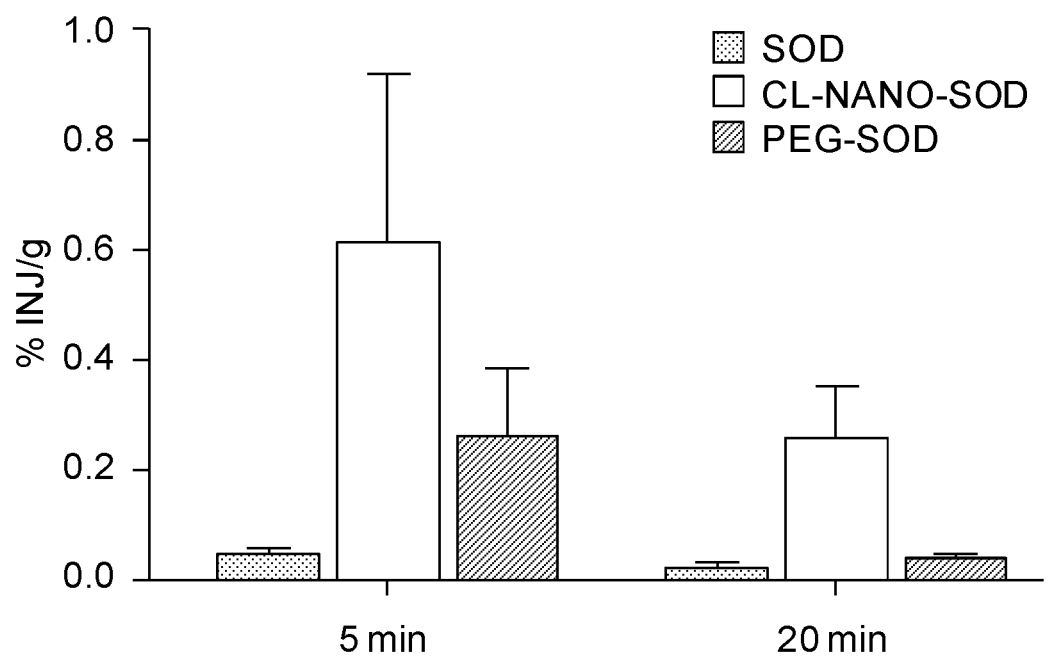
FIG. 30 shows crosslinked nano-SOD1 showing higher brain uptake than that of native SOD1 and PEGylated SOD1 (sigma product) at 5 and 20 min following intranasal administration.
Figure 31:
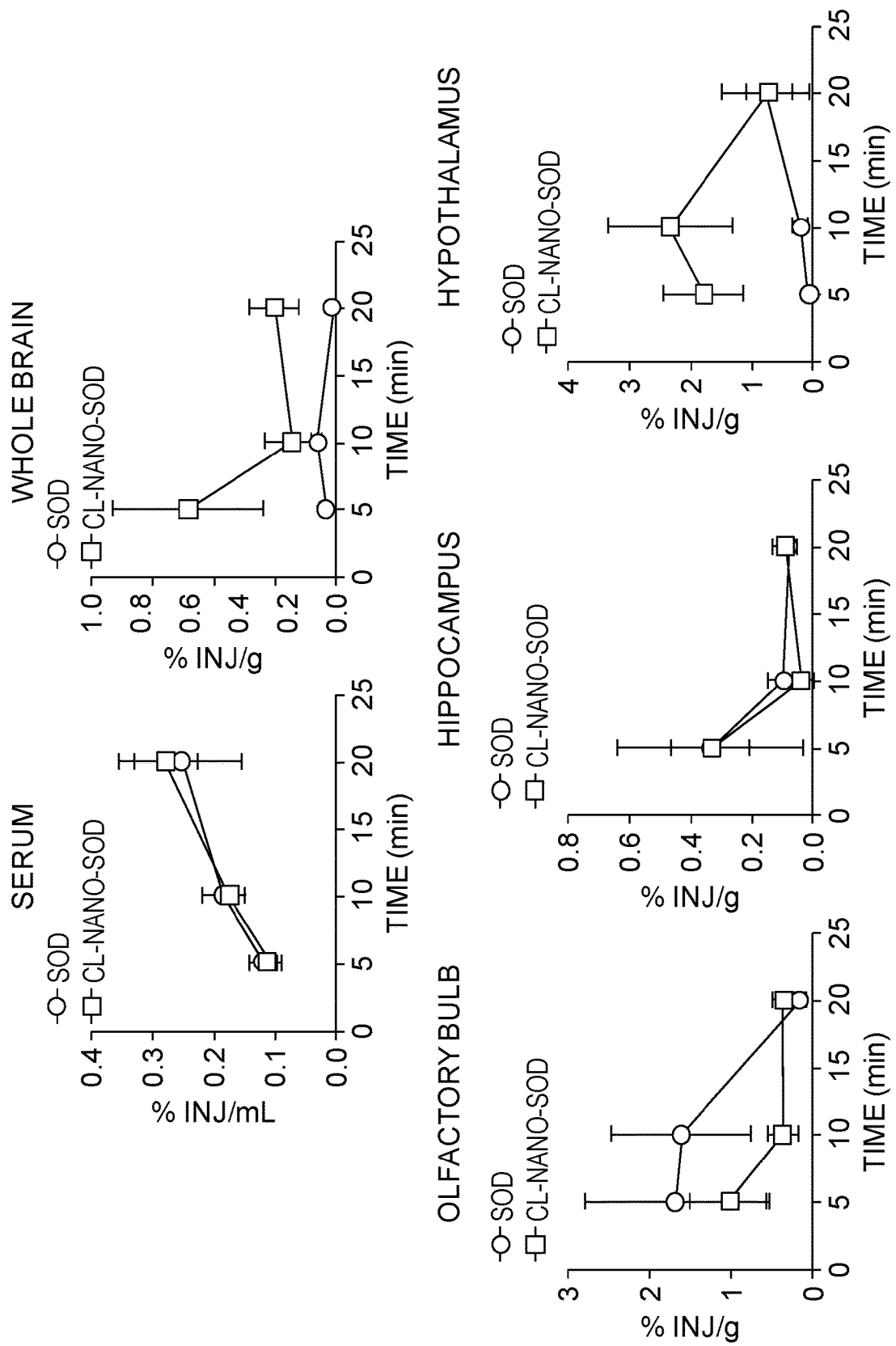
FIG. 31 shows crosslinked nano-SOD1 showing higher uptake in whole brain, olfactory bulb and hypothalamus but no difference in serum and hippocampus comparing to native SOD1 after intranasal administration.

Following intranasal administration, crosslinked nano-SOD1 shows increased brain uptake and hypothalamus targeting relative to native SOD1. In FIG. 30 it is demonstrated that $^{125}$I-crosslinked-nano-SOD1 uptake in the whole brain was dramatically increased compared to that of $^{125}$I-native-SOD1 and $^{125}$I-PEGylated-SOD1 at both 5 minutes and 20 minutes after administration. Analysis of the distribution of crosslinked nano-SOD1 in FIG. 31 suggests that within 20 min following INB delivery, significantly higher amount of crosslinked nano-SOD1 were delivered to the olfactory bulb and hypothalamus. Overall, our data suggest that crosslinked nano-SOD1 delivered by the INB route has improved delivery to the whole brain as well as to certain regions of the brain (olfactory bulb and hypothalamus) that are important targets for diseases involving elevated reactive oxygen species in these brain areas. Taken together our data represent a compelling rationale for advancing the development of crosslinked nano-SOD1 as a treatment for stroke and other CNS disorders.

Example 8

Complexes of Neurotrophin with Poly(Sarcosine)-Block-Poly(L-Glutamic Acid) and Block Copolymers A solution of 0.1 mg/ml BDNF in 10 mM phosphate buffer (pH=7.4) was mixed with a solution of poly(sarcosine)-block-poly(L-glutamic acid sodium salt) (PSar-PGA) or poly(2-methyl-2-oxazoline)-block-poly(L-glutamic acid sodium salt) (PMeOx-PGA) block copolymers in the same buffer at the charge ratio Z=7. In the PSar-PGA block copolymers the molecular mass of PSar block was 2.3 kDa (the degree of polymerization about 32) and 10.6 kDa (the degree of polymerization about 150) and of PGA 1.5 kDa (the degree of polymerization about 10), which corresponds to the abbreviations $PSar_{32}$-$PGA_{10}$, $PSar_{150}$-$PGA_{10}$, $PSar_{32}$-$PGA_{50}$, and $PSar_{150}$-$PGA_{50}$. In the PMeOx-PGA block copolymers the molecular mass of PMeOx block was 3.4 kDa (the degree of polymerization about 40) and 10.2 kDa (the degree of polymerization about 120) and of PGA 1.5 kDa (the degree of polymerization about 10) and 7.5 (the degree of polymerization about 50), which corresponds to the abbreviation $PMeOx_{40}$-$PGA_{10}$, $PMeOx_{120}$-$PGA_{10}$, $PMeOx_{40}$-$PGA_{50}$, and $PMeOx_{120}$-$PGA_{50}$. The hydrodynamic size of each sample was measured by dynamic light scattering. Formation of nanoparticles containing BDNF was confirmed by transmission electron microscopy.

The foregoing is illustrative of the present invention, and is not to be construed as limiting thereof. The invention is defined by the following claims, with equivalents of the claims to be included therein.

We claim:

1. A composition for delivery of a neurotrophin polypeptide to the central nervous system of a subject, the composition comprising a polyelectrolyte complex comprising a neurotrophin polypeptide and a synthetic block or graft copolymer comprising polyanion blocks and non-ionic blocks, wherein the charge ratio Z of the polypeptide to the polymer is at least 4.

2. The composition of claim 1, wherein the charge ratio Z is at least about 10 or 100.

3. The composition of claim 1, wherein the charge ratio Z is about 6 to about 7.

4. The composition of claim 1, Wherein the polypeptide and the synthetic polymer have opposite net charges.

5. The composition of claim 1, wherein the polypeptide and the synthetic polymer have the same net charge.

6. The composition of claim 1, wherein the polypeptide comprises at least one charge cluster, wherein charges within the cluster are separated by less than about 20, 15, or 7 Å.

7. The composition of claim 6, wherein the at least one charge cluster has an opposite net charge to the net charge of the synthetic polymer.

8. The composition of claim 7, wherein the at least one charge cluster comprises positively charge amino acids.

9. The composition of claim 1, wherein the block copolymer comprises poly(glutamic acid), poly(aspartic acid), or a copolymer of poly(glutamic acid) and/or poly(aspartic acid) with other amino acids that contain a majority of negatively charged amino groups.

10. The composition of claim 9, wherein the amino acids in the copolymer are L isomers, D isomers, or L/D isomers.

11. The composition of claim 1, wherein the block or graft copolymer comprises polyacrylic acid, polymethacrylic acid, polymaleic acid, and/or heparin.

12. The composition of claim 1, wherein the non-ionic blocks comprise poly(ethylene glycol), poly(2-methyl-2-oxazoline), poly(2-ethyl-2-oxazoline), poly-sarcosine, and/or elastin-like polypeptides.

13. The composition of claim 1, wherein the block or graft copolymer comprises poly(glutamic acid) and poly(ethylene glycol).

14. The composition of claim 13, wherein the block or graft copolymer comprises poly(ethylene glycol)$_{10-1000}$.

15. The composition of claim 13, wherein the block or graft copolymer comprises poly(glutamic acid)$_{8-150}$.

16. The composition of claim 13, wherein the block or graft copolymer is poly(ethylene glycol)$_{113}$-poly(L-glutamate)$_{50}$.

17. The composition of claim 1, wherein the neurotrophin polypeptide is selected from the group consisting of brain derived neurotrophic factor, nerve growth factor, neurotrophin 3, neurotrophin 4, glial cell derived neurotrophic factor, artemin, neurturin, persephin, ciliary neurotrophic factor, and any combination thereof.

18. The composition of claim 1, wherein the polyelectrolyte complex is in the form of nanoparticles.

19. The composition of claim 1, further comprising a pharmaceutically acceptable carrier.

20. A method of delivering a neurotrophin polypeptide to the central nervous system of a subject, comprising delivering the composition of claim 1 to the subject, thereby delivering the polypeptide to the central nervous system of the subject.

21. A method of treating a central nervous system disorder in a subject in need thereof, comprising delivering a therapeutically effective amount of the composition of claim 1 to the subject, thereby treating the central nervous system disorder in the subject.

22. The method of claim 21, wherein the disorder is Rett syndrome or stroke.

23. The composition of claim 13, wherein the block or graft copolymer comprises poly(ethylene glycol)$_{20-500}$.

24. The composition of claim 13, wherein the block or graft copolymer comprises poly(ethylene glycol)$_{40-250}$.

25. The composition of claim 13, wherein the block or graft copolymer comprises poly(ethylene glycol)$_{100-130}$.

26. The composition of claim 13, wherein the block or graft copolymer comprises poly(glutamic acid)$_{20-100}$.

27. The composition of claim 13, wherein the block or graft copolymer comprises poly(glutamic acid)$_{40-60}$.

* * * * *

UNITED STATES PATENT AND TRADEMARK OFFICE
CERTIFICATE OF CORRECTION

PATENT NO. : 11,484,574 B2
APPLICATION NO. : 16/073584
DATED : November 1, 2022
INVENTOR(S) : Kabanov et al.

Page 1 of 1

It is certified that error appears in the above-identified patent and that said Letters Patent is hereby corrected as shown below:

In the Specification

Column 13, Line 60: Please correct "glycop$_{10-1000}$," to read --glycol)$_{10-1000}$, e.g.,--

Column 25, Line 61: Please correct "PEG$_{113}$-POA$_{50}$" to read --PEG$_{113}$-PGA$_{50}$--

Column 35, Line 29: Please correct "Z$_{+/-}$2" to read --Z$_{+/-}$=2--

In the Claims

Column 36, Line 66, Claim 4: Please correct "Wherein" to read --wherein--

Signed and Sealed this
Twenty-eighth Day of February, 2023

Katherine Kelly Vidal
*Director of the United States Patent and Trademark Office*